US007893253B2

(12) United States Patent
Lohse et al.

(10) Patent No.: US 7,893,253 B2
(45) Date of Patent: Feb. 22, 2011

(54) SOLID-PHASE OLIGOSACCHARIDE TAGGING: A TECHNIQUE FOR MANIPULATION OF IMMOBILIZED CARBOHYDRATES

(75) Inventors: Anders Lohse, Copenhagen (DK); Malene Ryborg Jørgensen, Copenhagen (DK); Rita Martins, Lund (SE); Ole Hindsgaul, Valby (DK)

(73) Assignee: Merck Patent GmbH, Darmstadt (DE)

( * ) Notice: Subject to any disclaimer, the term of this patent is extended or adjusted under 35 U.S.C. 154(b) by 434 days.

(21) Appl. No.: 11/816,049

(22) PCT Filed: Feb. 8, 2006

(86) PCT No.: PCT/DK2006/000066

§ 371 (c)(1),
(2), (4) Date: May 7, 2008

(87) PCT Pub. No.: WO2006/084461

PCT Pub. Date: Aug. 17, 2006

(65) Prior Publication Data

US 2008/0227092 A1    Sep. 18, 2008

Related U.S. Application Data

(60) Provisional application No. 60/652,247, filed on Feb. 11, 2005.

(30) Foreign Application Priority Data

Feb. 11, 2005    (DK) ............................... 2005 00209

(51) Int. Cl.
C07H 3/00    (2006.01)
C12Q 1/68    (2006.01)
C12Q 1/70    (2006.01)
G01N 33/53    (2006.01)

(52) U.S. Cl. .............................. 536/124; 435/5; 435/6; 435/7.1; 435/7.2

(58) Field of Classification Search .................. 435/5, 435/6, 7.1, 7.2; 536/124
See application file for complete search history.

(56) References Cited

PUBLICATIONS

Nadkarni Varsha D. et al., Directional Immobilization of Herparin Onto the Nonporous Surface of Poolystyrene Microplates, Biotechniques, 1997, pp. 382-385, vol. 23, No. 3.

*Primary Examiner*—Jezia Riley
(74) *Attorney, Agent, or Firm*—Millen, White, Zelano, Branigan, P.C.

(57) ABSTRACT

The invention relates to methods of manipulating immobilised carbohydrates by derivatisation. Depending on the nature of the derivatisation, the carbohydrate may thereby be more easily detected and/or identified or handled. In particular, the invention relates to methods of preparing a reactive sugar comprising the steps of: i) providing a sample comprising a reducing sugar; ii) providing a solid support covalently attached to a linker comprising a capture group comprising an —NH2 group, wherein said linker optionally is attached to said solid support via a spacer; iii) reacting said reducing sugar with said —NH2 group, thereby obtaining an immobilised sugar; iv) reacting free —NH2 groups with a capping agent, wherein the capping agent comprises a reactive group capable of reacting with an —NH2 group; and v) reducing C═N bonds with a reducing agent, thereby obtaining an reactive sugar of the structure SugarCHn-NH— linked to a solid support via a linker and optionally a spacer, wherein n is 1 or 2.

46 Claims, 25 Drawing Sheets

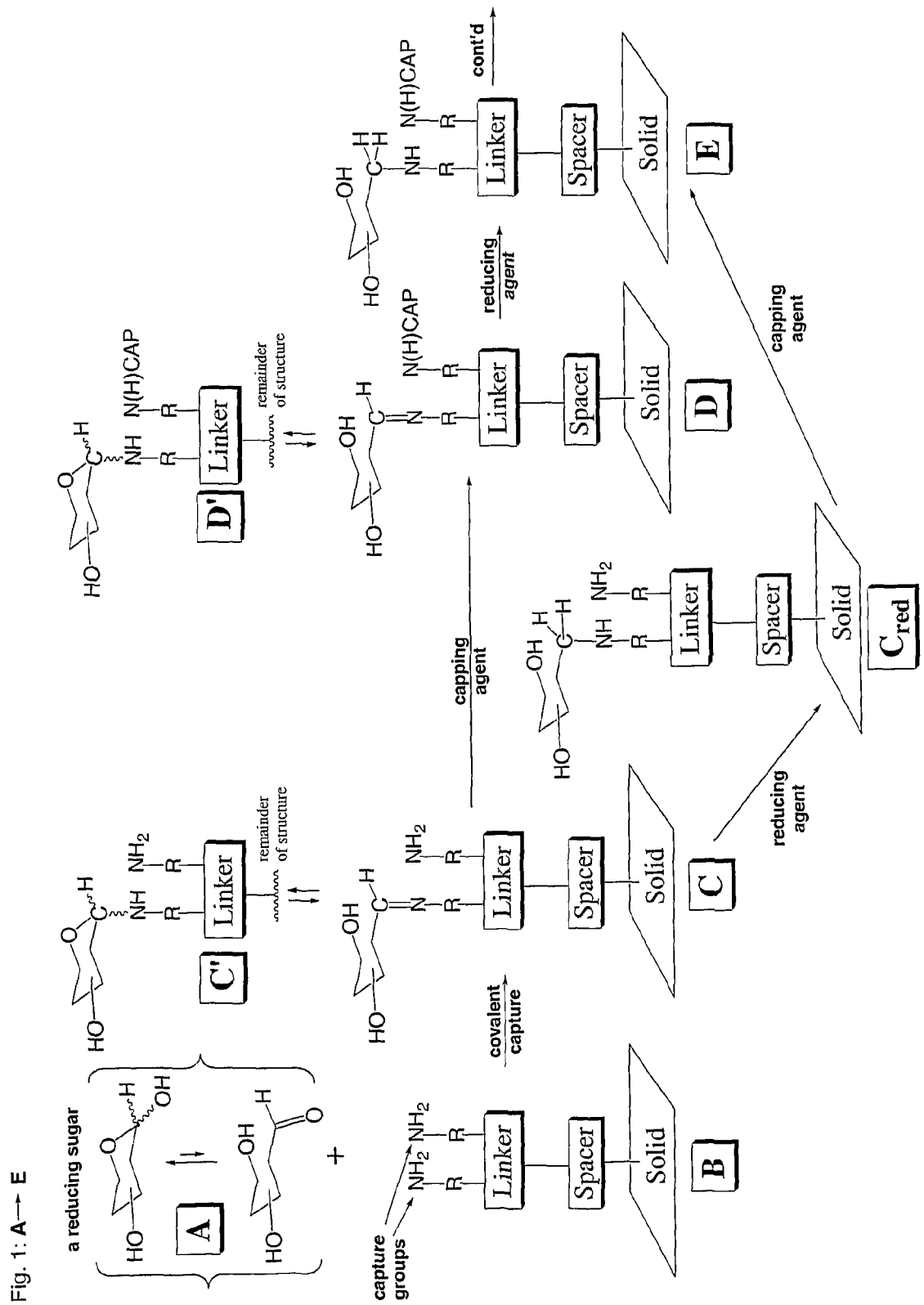
Fig. 1: A → E

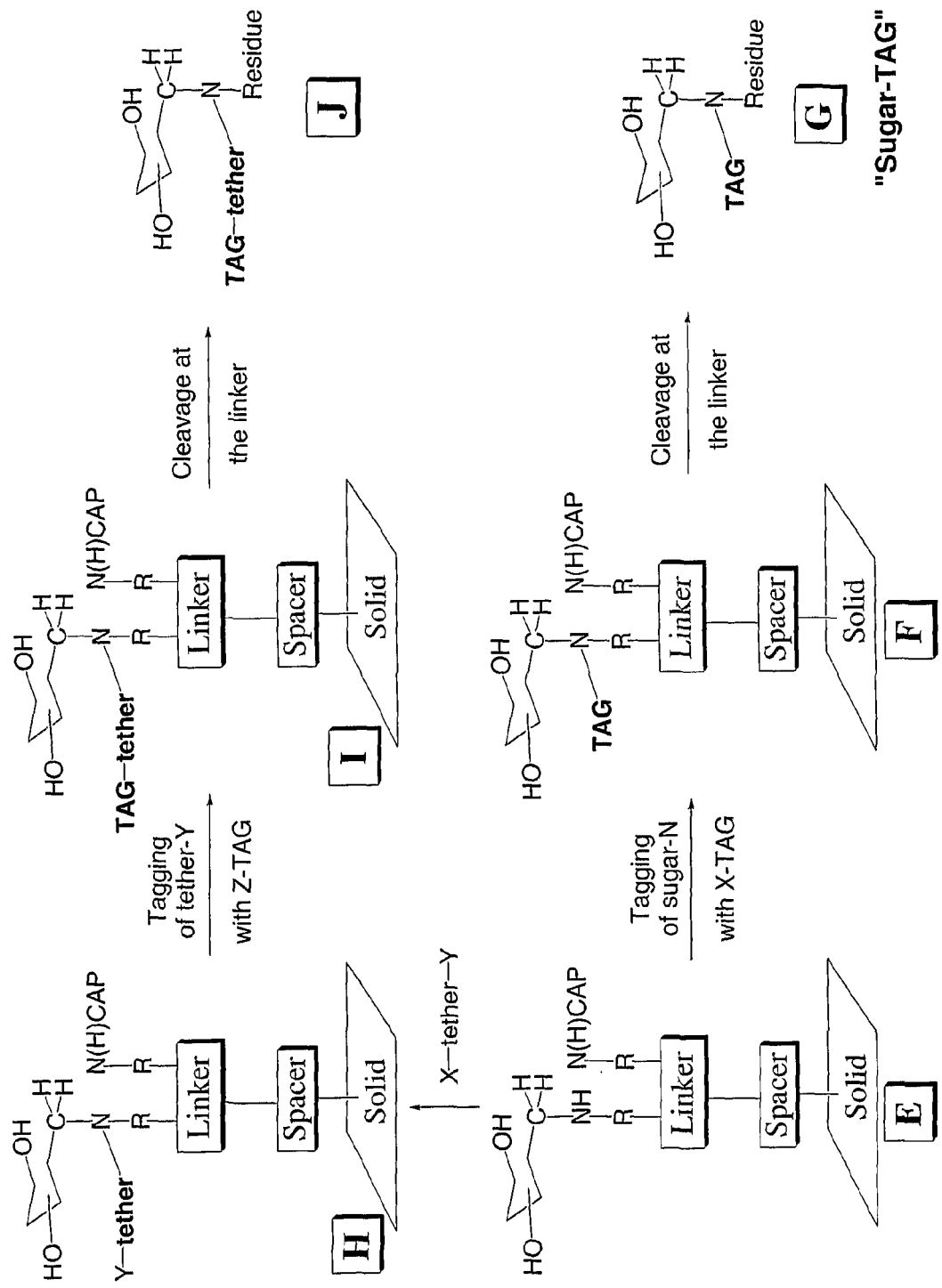
Fig. 1: E → G and J

Fig. 5
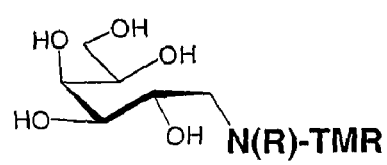
21: GalCH$_2$-N(R)-TMR
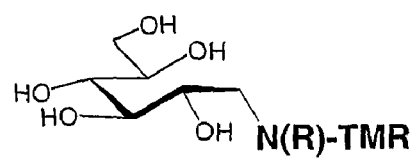
22: GlcCH$_2$-N(R)-TMR
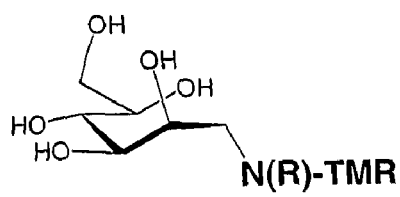
23: ManCH$_2$-N(R)-TMR
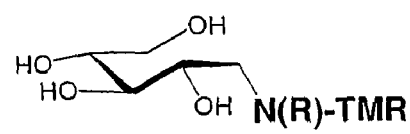
24: XylCH$_2$-N(R)-TMR
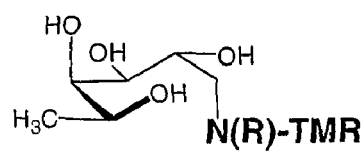
25: FucCH$_2$-N(R)-TMR
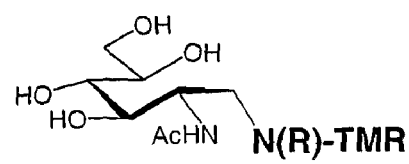
26: GlcNAcCH$_2$-N(R)-TMR
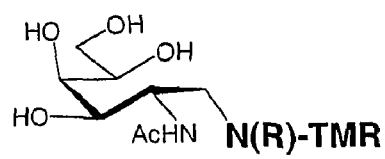
27: GalNAcCH$_2$-N(R)-TMR
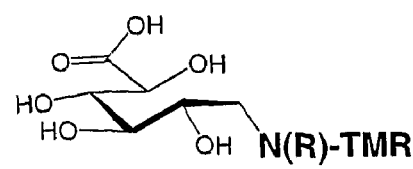
28: GlcACH$_2$-N(R)-TMR Fig. 7
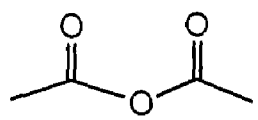
acetic anhydride
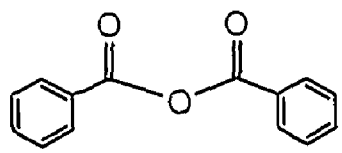
benzoic anhydride
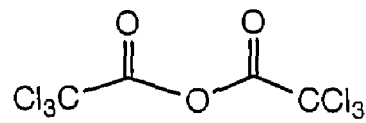
trichloroacetic anhydride
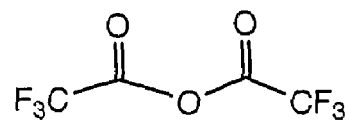
trifluoroacetic anhydride
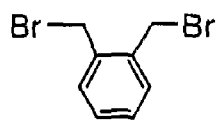
α,α'-dibromo-o-xylene
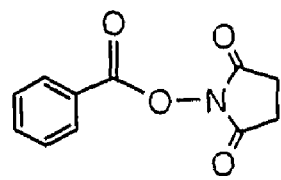
benzoic acid NHS-ester Fig. 8
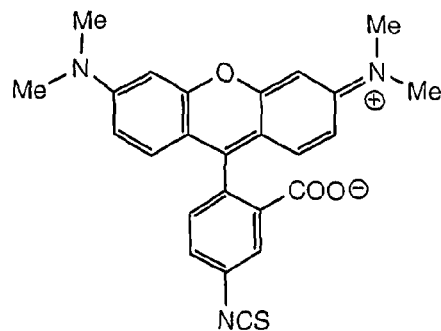
Tetrametylrhodamine isothiocyante
(TRITC)
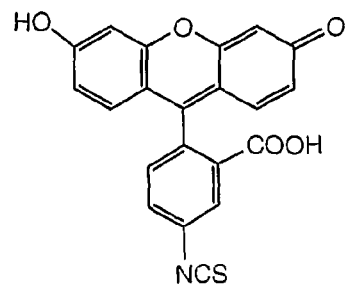
Fluorescein isothiocyante
(FITC)
p-bromophenyl isothiocyanate
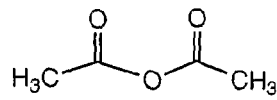
acetic anhydride
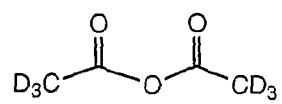
acetic anhydride-d$_6$
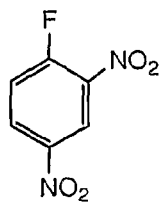
1-fluoro-2,4-dinitrobenzene
(Sanger reagent)

Fig. 10
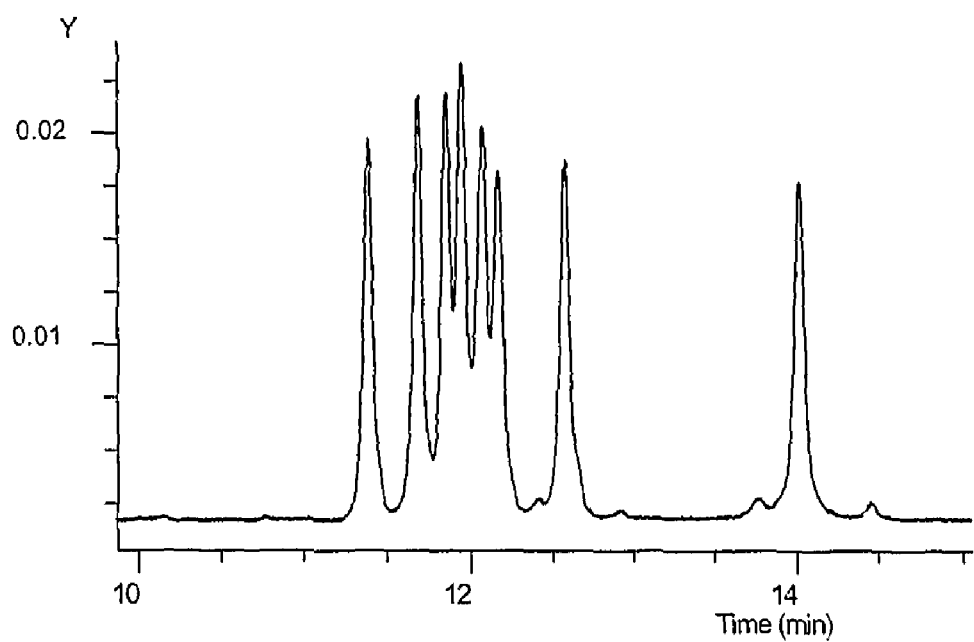
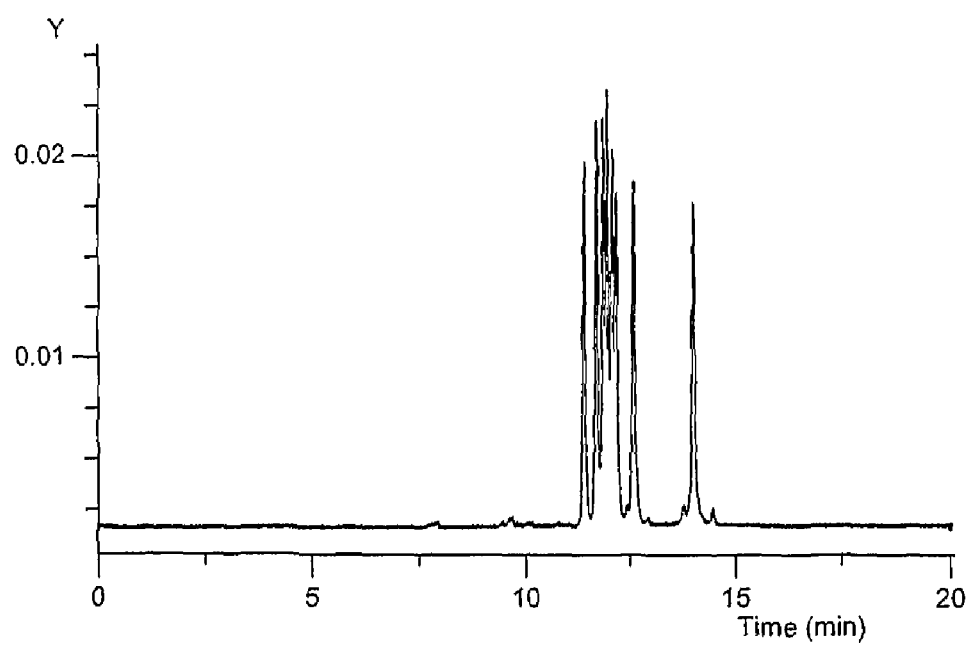

Fig. 13
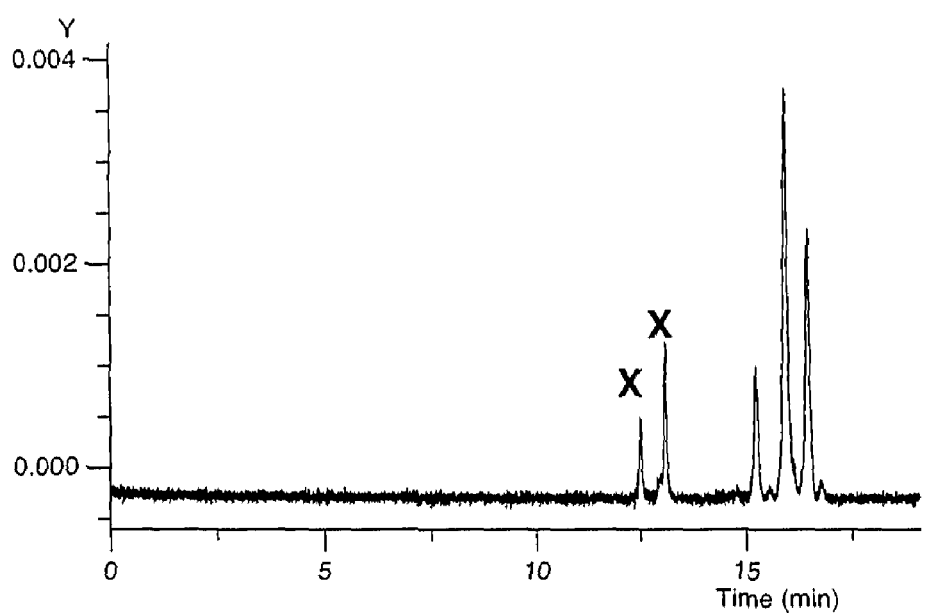
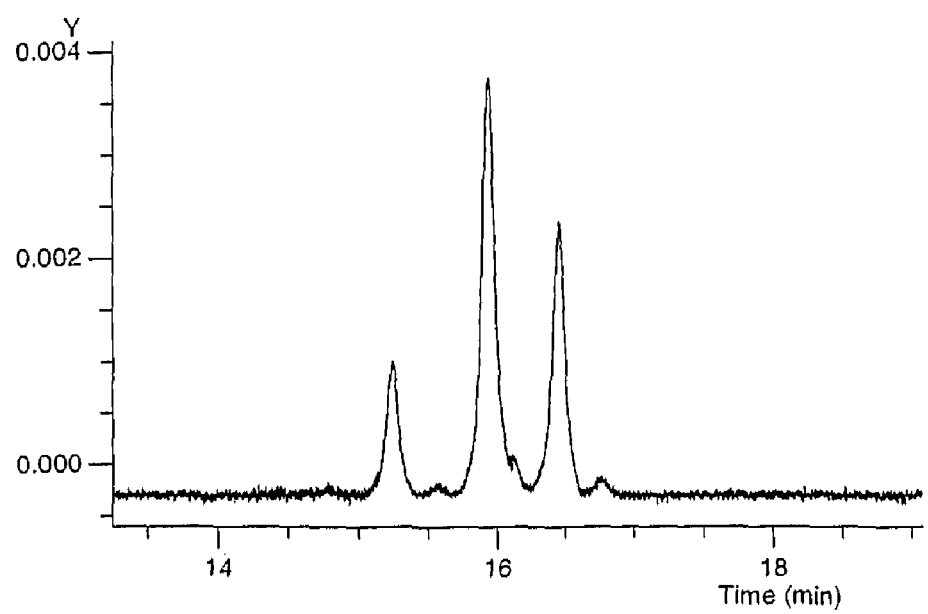

Fig. 14
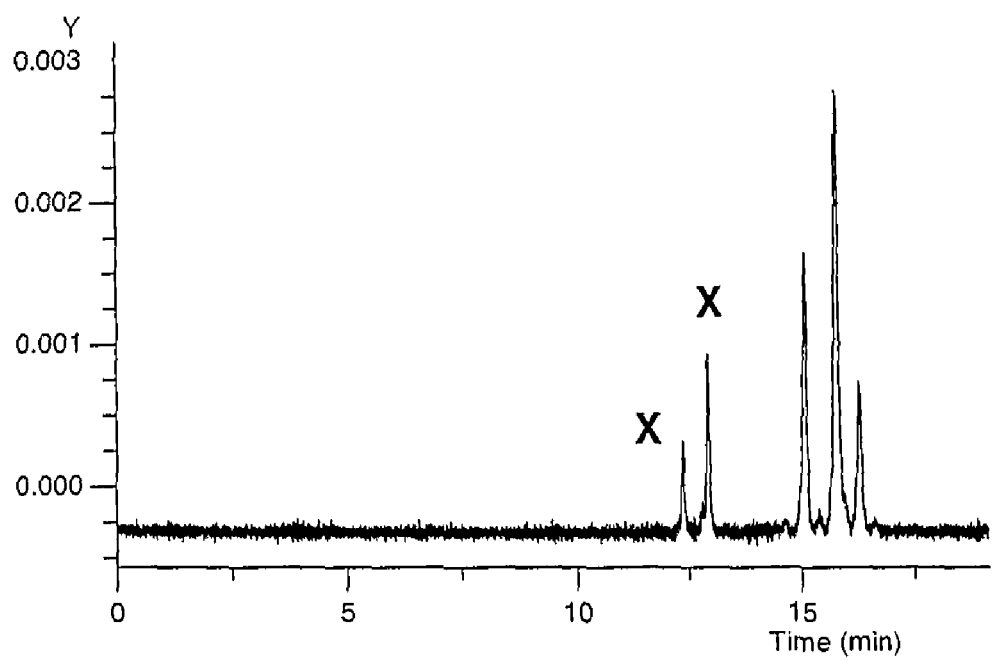
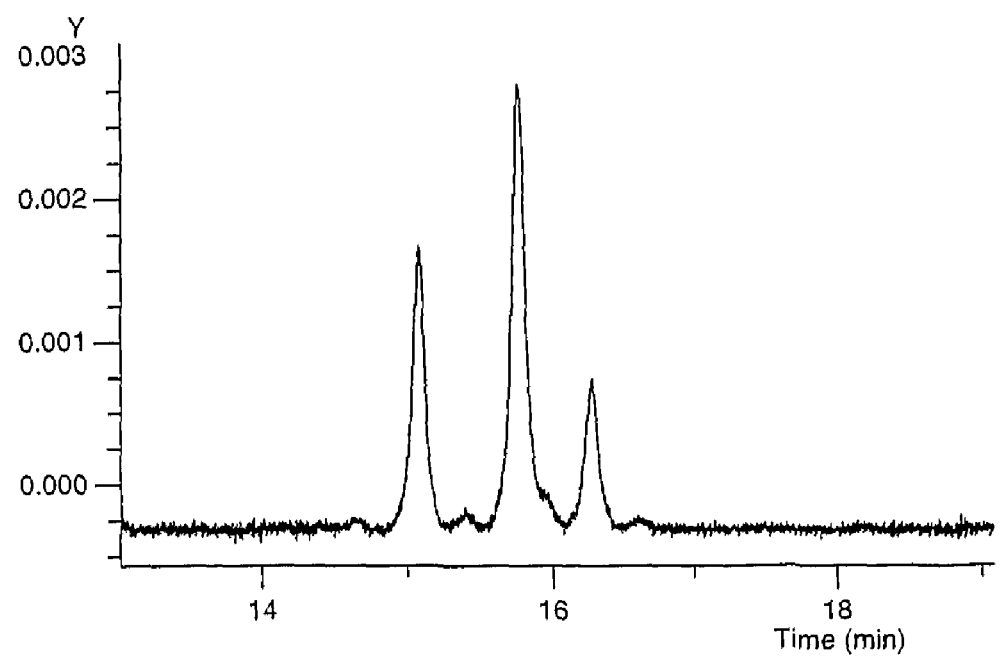

SOLID-PHASE OLIGOSACCHARIDE TAGGING: A TECHNIQUE FOR MANIPULATION OF IMMOBILIZED CARBOHYDRATES

This application claims the benefit of the filing date of U.S. Provisional Application Ser. No. 60/652,247 filed Feb. 11, 2005, which is incorporated by reference herein.

All patent and non-patent references cited herein are hereby incorporated by reference.

FIELD OF INVENTION

The present invention relates to the field of carbohydrate manipulation. In particular, the invention relates to methods of manipulating immobilised carbohydrates by derivatisation. Depending on the nature of the derivatisation, the carbohydrate may thereby be more easily detected and/or identified or handled. Thus, in one aspect the invention relates to the field of carbohydrate detection and identification.

BACKGROUND OF THE INVENTION

Carbohydrates exist in many forms in nature. In animals including man, examples include free reducing sugars in solution (such as the monosaccharide glucose in serum), free oligosaccharides in solution (such as the disaccharide lactose in milk), they can be attached to peptides or proteins through covalent linkages to a variety of amino acids (such as asparagine, serine, threonine and others), covalently attached to lipids such as ceramide (as in gangliosides) or attached to membrane anchors via phosphatidylinositols. Sugars are also found attached to many small molecules including some involved in metabolism, such as glucuronides. In the above examples, the length of the sugar chains can vary from one to over 100 sugar residues.

In lower organisms, including bacteria and plants, an even wider array of structures exists. The surface of bacterial cells can be covered by sugar polymers that are thousands of residues long, which can act as antigens in the detection of bacteria and as vaccines. Sugars are an integral part of bacterial cell walls. The sugars can themselves be antibiotics (such as the aminoglycoside antibiotics, for example streptomycin), or can be found as essential components of antibiotics (such as erythromycin and vancomycin), as enzyme inhibitors (as in Acarbose) or as anti-cancer agents (such as for example calicheamycin).

One area of particular interest is the structure of the carbohydrate chains (glycans) found attached to glycoproteins and glycolipids. The glycosylation pattern of glycoproteins has been shown to be important for their biological functions, including their bioavailability, their targeting, and have even been directly correlated with the metastatic potential of tumor cells. The glycosylation pattern of human serum transferrin, for example, is being used as a diagnostic test for a series of genetic diseases termed Carbohydrate-Deficient Glycosylation Syndromes. Specific glycolipid sequences have been shown to be involved in neuronal development and cell surface signalling, in diabetes, and are accumulated in certain specific metabolic diseases such as Tay-Sachs, for which they are diagnostic.

The linkages between the sugar residues in the oligosaccharides and polysaccharides described above can have either the alpha or beta configurations, and the glycans can be multiply branched. The diversity of structures possible for glycan chains is therefore enormous and their structural characterization is therefore inherently complex. There is therefore a strong interest in methods for the detection, structural characterization, identification, quantitation, and chemical/enzymatic manipulation of carbohydrate and glycan structures, in research, in diagnostics, in monitoring the glycosylation of recombinant glycoproteins and in the development of new pharmaceutical agents.

Several methods are in current use for the analysis for carbohydrate structures, and these have recently been reviewed. Underivatized oligosaccharides and glycolipids can be analyzed by NMR-spectroscopy, by mass-spectrometry, and by chromatography. For the much larger glycoproteins, mass spectrometry provides more limited information but analysis of their proteolytic digests, i.e. glycopeptides, has been extensively used. Indirect structural information about underivatized oligosaccharides can also be deduced from their abilities to interact with carbohydrate-binding proteins such as lectins, antibodies or enzymes.

Carbohydrates themselves have no characteristic chromophores, only N-acetyl groups, so monitoring their separation by optical or spectroscopic detection is not commonly used. Pulsed amperometric detection of the polyols has however been an important technique for detection in chromatography.

The most widely used method for high-sensitivity detection of carbohydrates has been the labeling of the reducing ends (lactols, tautomers of hydroxyaldehydes and hydroxyketones) with either radioactive or fluorescent TAGs. Both chemical and enzymatic methods have been described that cleave carbohydrates from glycoproteins and glycolipids, permitting the generation of the required reducing sugars from glycoproteins, glycolipids and other glycoconjugates. Most commonly, such reducing sugars are reacted with amino-containing derivatives of fluorescent molecules under conditions of reductive amination: i.e., where the initially formed imines (C=N) are reduced to amines (CH—NH) to produce a stable linkage. In most cases, the labeling reactions have been performed in solution using a large excess of labeling agent. This requires separation of the excess labeling agent and its by-products prior to or during analysis. Other TAGs of utility in mass-spectrometry have been added in the same manner, by either amination or reductive amination, the detection then being performed by the mass-spectrometer.

Once the label has been added to permit specific detection, the carbohydrates described above can subsequently be subjected to separation and detection/quantification. Additional structural information can be obtained by exposing the tagged carbohydrates to enzymes such as glycosidases. If specific glycosidases act on the tagged carbohydrates, they can cleave one or more sugar residues resulting in a change in chromatographic or electrophoretic mobility, as detected by, for example, a fluorescence detector in HPLC, CE or by a change in their mobility in SDS-PAGE, or a change in their mass as detected by a change in m/z value in a mass-spectrometer. Arrays of enzymes have been used to provide a higher throughput analysis.

Below a short overview of prior art is given:

Gao et al. 2003 reviews suitable techniques for derivatisation of carbohydrates in solution. In solution carbohydrates may be derivatised by reductive amination. In general, —$NH_2$ groups of amines may react with aldehyde or ketone group of reducing sugars, thereby producing compounds of —C=N structure. Such compounds may further be reduced for example by $NaCNBH_3$. Gao et al., 2003 does not disclose manipulation of immobilised carbohydrates.

U.S. Pat. No. 5,100,778 describes a method for oligosaccharide sequencing comprising placing an identifying label on the reducing terminal residue of an oligosaccharide, dividing into a plurality of separate portions, treating each portion with for example specific glycosidases, pooling product and analysing the pools obtained. The document does not describe immobilised oligosaccharides.

U.S. Pat. No. 4,419,444 describes methods for chemically binding organic compounds containing carbohydrate residues to a support bearing reactive —$NH_2$ groups. The methods involve either the periodate oxidation of carbohydrate diols to produce reactive aldehydes by cleaving of C—C bonds in the carbohydrate or oxidation of —$CH_2OH$ groups to —CHO groups enzymatically. Both oxidations will result in alteration of the structure of the carbohydrate. The reactive aldehydes can be immobilised by reaction with the —$NH_2$ groups. After immobilisation of the carbohydrate containing compound a reduction step (for example using $NaBH_4$) may be performed to increase stability. The document describes neither the immobilization of a reducing sugar through its reducing end nor manipulation of immobilised altered carbohydrate containing compounds via the reduced amine bond. Furthermore, the chemical nature of the carbohydrate has been altered and this alteration may impair further modulations, such as specific enzymatic cleavage by glycosidases. The document also does not describe the addition of any chemical reagents to the immobilised oligosaccharide that result in the addition of molecular structures to it.

WO92/719974 describes a method of sequencing oligosaccharides. The method involves immobilising oligosaccharides on a solid support and subsequent treatment with a variety of glycosidases. Prior to immoblisation, the oligosaccharide may be linked to a conjugate. The document does not describe modulation of immobilised oligosaccharides other than glycosidase treatment.

The above describes the biological importance and complexity of glycans, and summarizes some benefits of attaching TAGs to reducing sugars, such as monosaccharides, as well as to the reducing sugar end of oligosaccharides. To date, such attachment has been performed in solution using large excesses of tagging agent (and often additional chemical agents such as reducing agents), and thus require time consuming and frequently difficult separation techniques to be applied before either detection or further manipulation. Such separation techniques invariably result in losses of material, and dilution, thus considerably complicating and biasing the analysis. There is therefore a great need for simple methods that can install a TAG onto a carbohydrate structure and further manipulate the structure, without the need for complex and biased methods for separating reaction starting materials, reagents, by-products and sought after products. We describe herein such simple methods.

SUMMARY OF THE INVENTION

The present invention relates to methods of covalent attachment of reducing sugars, (which may be any of the reducing sugars mentioned herein below in the section "Reducing sugar") to a solid-support (which may be any of the solid supports described herein below in the section "Solid support") through reaction with an immobilized molecule consisting of an optional spacer (i.e. with or without spacer) and a linker (which can be cleavable) that incorporates a capture group containing an —$NH_2$ functionality. The resulting immobilized sugar has an acyclic form with a C=N bond, which may be in equilibrium with it's cyclic glycosylamine tautomer.

Free —$NH_2$ groups on the solid support after immobilisation may be capped and the C=N bond can be reduced. This method is outlined in FIG. 1 A+B→E. The figure shows an underivatised pyranose, which however is meant to represent any reducing sugar.

In a variation, the methods of the invention may comprise reduction of the immobilized sugar containing a C=N bond (exemplified by structure C, FIG. 1) to CH—NH prior to capping free —$NH_2$ groups, producing a compound of structure $C_{red}$ (FIG. 1). The —$NH_2$ groups in $C_{red}$ may then be capped at this stage to produce a compound of the same structure E as that produced by the sequence C to D to E described above and shown in FIG. 1.

Compounds of the structure E may thus be produced by either the sequence A+B goes to C goes to D goes to E, or A+B goes to C goes to $C_{red}$ goes to E.

It is therefore an object of the present invention to provide methods of preparing a reactive sugar, said method comprising the steps of
  i. Providing a sample comprising a reducing sugar (such as A in FIG. 1)
  ii. Providing a solid support (e.g. solid in FIG. 1) covalently attached to a linker comprising a capture group comprising an —$NH_2$ group, wherein said linker optionally is attached to said solid support via a spacer (such as B in FIG. 1)
  iii. Reacting said reducing sugar with said —$NH_2$ group, thereby obtaining an immobilised sugar (such as C in FIG. 1),
  iv. Reacting free —$NH_2$ groups with a capping agent, wherein the capping agent comprises a reactive group capable of reacting with a —$NH_2$ group
  v. Reducing C=N bonds with a reducing agent
  vi. thereby obtaining a reactive sugar containing the structure SugarCH$_n$—NH— linked to a solid support via a linker and optionally a spacer, wherein n is 1 or 2 (such as compound E of FIG. 1), wherein steps iv and v may be performed in any order.

In embodiments of the invention wherein step iv is performed prior to step v, capping —$NH_2$ groups in step iv will for example result in compound D of FIG. 1, whereas the reduction performed in step v will for example result in compound E of FIG. 1;

In embodiments of the invention wherein step v is performed prior to step iv, then the reduction of the C=N bond (for example of compound C of FIG. 1) will for example result in compound $C_{red}$ of FIG. 1. The capping of the —$NH_2$ groups in step iv will for example produce the compounds of structure E, FIG. 1. It is comprised within the present invention that the sample comprising the reducing sugar may be incubated with the solid support and the reducing agent simultaneously. Thus, reduction of C=N bonds (step v) will be performed immediately following reaction of the reducing sugar with the —$NH_2$ group of the solid support (step iii).

In step iii), preferably, the reducing end of said reducing sugar is reacted with said —$NH_2$ group. Thus preferably the aldehyde group or the hemiacetal of the reducing sugar is reacted with the —$NH_2$ group.

It is preferred that the methods further comprise the step of
  vii. Reacting the —NH— group of the reactive sugar (for example compound E of FIG. 1) with a derivatising agent comprising a nitrogen-reactive functional group (X), thereby obtaining a sugar covalently attached to said agent. Said sugar covalently attached to said agent may for example be compound F of FIG. 1 (when the derivatising agent is a TAG) or compound H of FIG. 1, when the derivatising agent is a tether linked to functional group.

The term "TAG" in the present context, and in FIG. 1 (vide infra) is meant to indicate any atom, molecule or entity that can become covalently attached to another molecule thereby labelling said another molecule as having undergone the covalent attachment.

DESCRIPTION OF DRAWINGS

FIG. 1 illustrates an example of the method according to the invention. FIG. 1: A-E illustrates capture and manipulation of a reducing sugar on a solid support to give a reactive sugar E. FIG. 1: E-G and J illustrates manipulation of a reactive sugar E on a solid support, and cleavage of a tagged sugar. The methods of the invention may comprise one or more of the steps illustrated in the FIG. 1. In the FIG. 1 the reducing sugar is exemplified with a pyranose, however any reducing sugar may be used with the method. The figure shows an example where the linker is linked to the solid support via a spacer, however, the linker may also be directly linked to the solid support. The solid support is designated "Solid" in the figure, however it may be any of the solid supports mentioned herein below.

FIG. 5. Structures 21-28 of synthetic tagged derivatives of the eight common mammalian monosoaccharides of general structure $SugarCH_2$—$N(R)$-TMR.

FIG. 7. Structures of some capping agents.

FIG. 8. Structures of some nitrogen-reactive tagging agents used, of general structure TAG-X FIG. 9. Example of E goes to J (30) using the protected nitrogen-reactive agent 29 of general structure X-tether-$Y_P$.

FIG. 10. Separation by CE of the eight TMR-labelled monosaccharide standards shown in FIG. 5. The order of elution is GalNAc (27), Xyl (24), Man (23), Glc (22), GlcNAc (26), Fuc (25), Gal (21), and GlcA (28). The top trace is an expansion.

FIG. 13. CE of $G^P6_a$ (with monosaccharide mixture 6 tagged using TRITC, section 4.2.3). X denotes unidentified peaks. The order of elution is GalNAc (27), Man (23) and Fuc (25). The lower trace is an expansion.

FIG. 14. CE of $G^P7_a$ (with monosaccharide mixture 7 tagged using TRITC, section 4.2.4). X denotes unidentified peaks. The order of elution is GalNAc (27), Man (23) and Fuc (25). The lower trace is an expansion.

DETAILED DESCRIPTION OF THE INVENTION

Methods of Manipulating a Reducing Sugar

Figure 2:
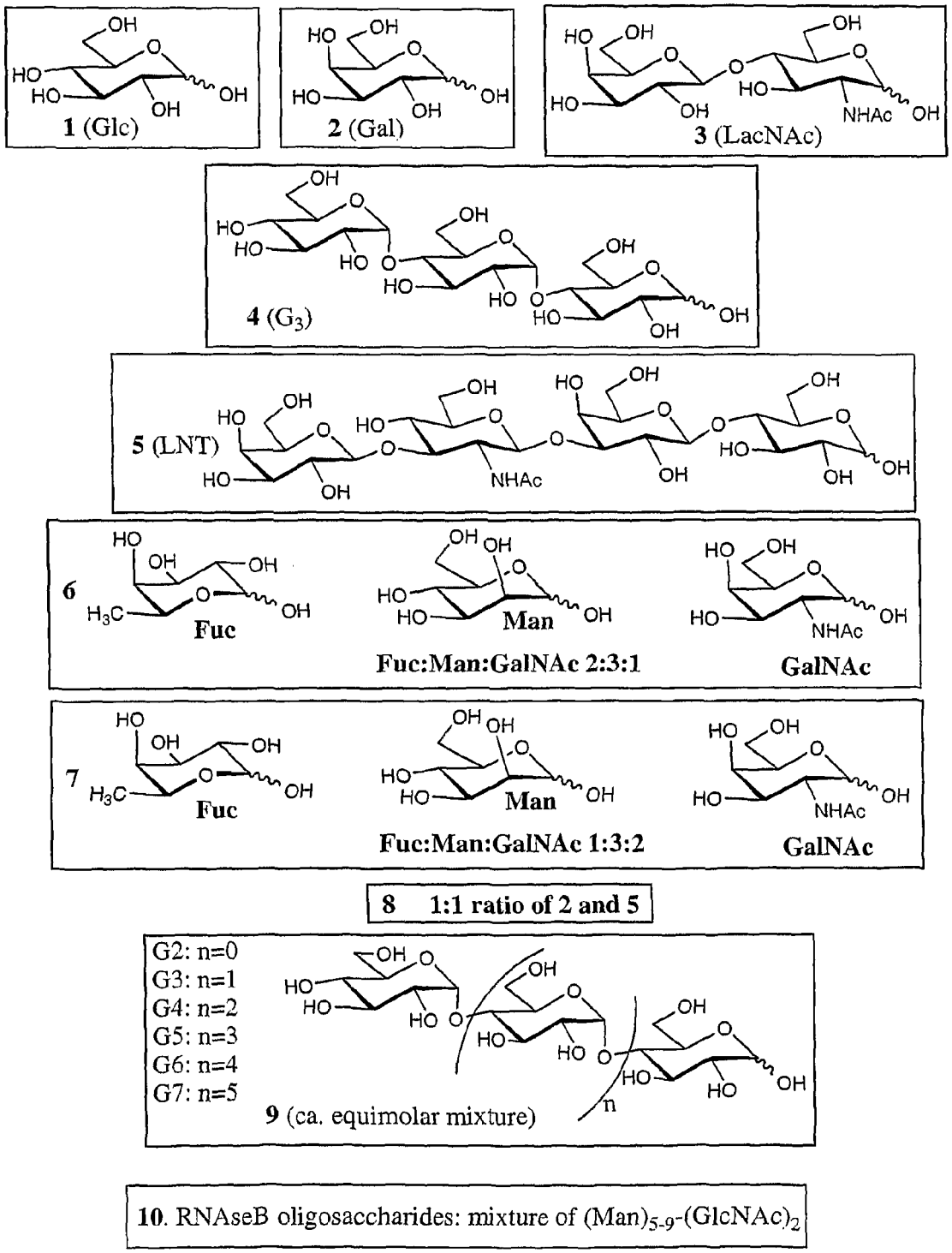
FIG. 2. Structures 1-10 of the reducing sugars, and mixtures thereof, used in the examples of the present invention.

The present invention relates to methods of manipulating a reducing sugar. An example of the methods of the invention is outlined in FIG. 1. It should be noted that the methods of the invention do not necessarily involve all of the steps illustrated in FIG. 1. Thus the methods may comprise only some of the steps outlined in FIG. 1. Preferably, the methods will comprise at least the steps A+B→C, C→D and D→E, or the steps A+B→C, C→$C_{red}$ and $C_{red}$→E In FIG. 1 the reducing sugar is exemplified by a pyranose, however any reducing sugar may be used with the invention, in particular any of the reducing sugars described herein below in the section "Reducing sugar". The —OH group dissecting the pyranose ring in FIG. 1 is meant to indicate that the reducing sugar may bear one or more hydroxyl groups attached to it.

Each of the steps of the methods of the invention are described herein below in more detail, wherein capital letters A to J and $C_{red}$ refer to FIG. 1

The identity of each of the compounds or intermediates of the present invention, for example of compounds A, B, C, $C_{red}$, D, E, F, G, H, I or J may be verified by standard techniques known to the skilled person, such as by NMR.

A. Reducing Sugar

The term "reducing sugar" as used herein covers the classical definition of sugars that are capable of reducing $Cu^{2+}$ to $Cu^+$. Whether a sugar is reducing may for example be tested using Fehlings reagent. In more modern terminology, reducing sugars are sugars that comprise an aldehyde group or a hemiacetal of the formula $R_2C(OH)OR'$, wherein R' is not H. Preferably, a reducing sugar is a carbohydrate structure containing an aldehyde, which is in equilibrium with the cyclized form called a hemiacetal. D-glucose is a non-limiting example of such a reducing sugar. The most abundant cyclic forms contain 5-membered rings, termed furanoses, and 6-membered rings termed pyranoses. (See rules of nomenclature).

The term "sugar" as used herein covers monosaccharides, oligosaccharides, polysaccharides, as well as compounds comprising monosaccharide, oligosaccharide, or polysaccharide. The terms "carbohydrate" and "sugar" are herein used interchangeably.

Oligosaccharides and polysaccharides are compounds consisting of monosaccharides linked glycosidically. In general polysaccharides comprise at least 10 monosaccharide residues, whereas oligosaccharides in general comprise in the range of 2 to 10 monosaccharides. Oligosaccharides and polysaccharides may be linear or branched. A monosaccharide is defined as a polyhydroxy aldehyde H—$(CHOH)_n$—CHO or polyhydroxyketone H—$(CHOH)_n$—CO—$(CHOH)_m$—H, wherein m and n are integers. Preferred monosaccharides comprises in the range of 4 to 9 carbons, thus preferably for polyhydroxy aldehydes n is an integer in the range of 3 to 8 and for polyhydroxyketones n+m is an integer in the range of 3 to 8. Monosaccharides are compounds such as aldoses and ketoses and a wide variety of derivatives thereof. Derivation includes those obtained by oxidation, deoxygenation, replacement of one or more hydroxyl groups by preferably a hydrogen atom, an amino group or thiol group, as well as alkylation, acylation, sulfation or phosphorylation of hydroxy groups or amino groups. According to IUPAC nomenclature, carbohydrates are compounds of the stoichiometric formula $C_n(H_2O)_n$, such as aldoses and ketoses as well as substances derived from monosaccharides by reduction of the carbonyl group (alditols), by oxidation of one or more terminal groups to carboxylic acids, or by replacement of one or more hydroxyl group(s) by a hydrogen atom, an amino group, thiol group or similar groups or derivatives of these compounds.

In a preferred embodiment, the reducing sugar is a naturally occurring reducing sugar or a reducing sugar, which has been liberated from a naturally occurring or recombinantly produced compound comprising a carbohydrate, preferably without having been subject to furthermore modifications after liberation. In particular it is preferred that the reducing sugar, is a naturally occurring reducing sugar or a reducing sugar liberated from a naturally occurring or recombinantly produced compound, wherein none of the alcohol groups of said naturally occurring sugar or said liberated sugar have been enzymatically transformed to an aldehyde or ketone by oxidation at the level of the oligosaccharide. It is also preferred that the reducing sugar, is a naturally occurring reducing sugar or a reducing sugar liberated from a naturally occurring or recombinantly produced compound, wherein said naturally occurring sugar or said liberated sugar have not been subjected to periodate treatment. It is thus generally preferred that no alcohol group of said naturally occurring sugar or said liberated sugar have been transformed to an aldehyde or ketone. In this context recombinantly produced compounds are compounds produced by a living organism with the aid of recombinant technologies, for example heterologous glycoproteins.

Reducing sugars may be derived from a variety of sources. For example the reducing sugar may be obtained from a living organism or part of a living organism, such as animals or plants or from one or more specific animal or plant tissues, from organisms such as prokaryotic or eukaryotic cells, from viruses, from in vitro cultivated mammalian cells, insect cells, plant cells, fungi, bacterial cells, yeast, or phages. For example the reducing sugar may be isolated from extracts of any of the aforementioned cells, microbial organisms or living organisms. Such extracts may comprise reducing sugars, such as free carbohydrates. Extracts may also comprise compounds comprising monosaccharide, oligosaccharide, polysaccharide or carbohydrate moieties, notably glycoproteins or glycolipids or small organic molecules to which carbohydrates are attached, which are generally referred to as glycosides. Glycoproteins are compounds in which a carbohydrate component is linked to a peptide, polypeptide or protein component. Thus as used herein the term glycoprotein also cover proteoglycans and glycosaminoglycans. Glycolipids are compounds containing one or more monosaccharide, oligosaccharide, polysaccharide or carbohydrate moieties bound by a glycosidic linkage to a hydrophobic moiety such as an acylglycerol, a sphingoid, a ceramide (N-acylsphingoid) or a prenyl phosphate. Glycosides are meant to describe small (MWt 100-5000) organic molecule glycosidically linked to one or more sugars via either O, N or S.

Reducing sugars may also be the products of chemical synthesis, or chemical/enzymatic synthesis, such as oligosaccharides prepared in vitro by chemical synthesis in solution or on the solid phase. These same synthetic oligosaccharides may be further modified by enzymatic reaction, such as for example by the sulfation, phosphorylation or glycosylation. Thus the methods described herein may also be used for manipulation of synthetic or semi-synthetic oligosaccharides or oligosaccharide libraries.

Preferably, the monosaccharide, oligosaccharide, polysaccharide or carbohydrate moiety is liberated from the glycoprotein, prior to performing the methods of the invention. This may be done by standard methods known to the skilled person. N-linked monosaccharides, oligosaccharides, polysaccharides or carbohydrates may be cleaved from glycoproteins by chemical or enzymatic methods. Enzymatic methods may for example involve use of glycosidases such as endoglycosidases H and F or N-glycanases such as PNGase-F. O-linked monosaccharides, oligosaccharides, polysaccharides or carbohydrates may be cleaved from glycoproteins by chemical methods, including hydrazinolysis or alkaline β-elimination or enzymatically using enzymes such as an O-glycosidase. Chemical methods useful for release of both N-linked and O-linked includes reactions with strong nucleophiles and/or strong bases such as hydrazine. Carbohydrates may be cleaved from small organic molecules using either acidic or basic reactions, or by the action of glycosidases.

In one embodiment of the invention a predetermined amount of a reference standard is added to the sample comprising the reducing sugar. This may facilitate quantification of said reducing sugar after immobilisation or after immobilisation and release in embodiments of the invention wherein the linker is cleavable.

The reference standard may be any compound capable of reacting with —$NH_2$, for example any compound comprising one of the nitrogen reactive functional groups described herein below in the section "E→F. Adding TAGs". Preferably the reference standard is an aldehyde or a ketone, more preferably a sugar. In another embodiment of the invention, the same or different reference standard is added to the solid support prior to contact with the solution containing the reducing sugar with or without the added reference standard included in the solution (see herein below in section "B. Solid support"). Thus two or more reference standards may be used, one (or more) added to the solid support prior to contact of the solid support with the solution comprising a reducing sugar, and one or more added to the solution containing the reducing sugar.

One or more reference standards may also be added to the solid support after contact with the reducing sugar, but preferably prior to capping. Thus for example the reference standard may be added to compound C or $C_{red}$ of FIG. 1, preferably after a washing step.

In embodiments of the invention wherein the solid support is coupled to a reference standard (see herein below in section "B. Solid support") it is preferred that different reference standards are used.

In one embodiment of the invention the methods comprises a step of pre-treatment of the sample to be used with the method. In particular, a sample comprising glycosidically-linked sugars such as a glycoproteins, glycolipids or glycosides may be pretreated with a scavenger resin prior to reaction with the solid support. The scavenger resin is preferably a resin comprising a nucleophilic group capable of reacting with aldehydes and ketones, including reducing sugars, preferably the scavenger resin comprises an amino group or a hydrazine. Incubation of the sample with the scavenger resin will thus remove additional aldehydes, ketones and reducing sugars. After pre-treatment, such methods will in general further comprise the step of liberating reducing sugars from said glycosidically-linked sugars thereby obtaining a sample comprising reducing sugars. The vast majority of aldehydes and ketone within said sample will thus be reducing sugars released from glycosidically-linked sugars. Said reducing sugars may be liberated by a number of methods, including chemical or enzymatic methods, such as any of the methods described herein above in this section. Treatment of the pretreated sample with for example PNGaseF can cause the release of reducing oligosaccharides into solution for capture and manipulation according to the methods of the invention. The oligosaccharides thus released will be essentially free of contaminating carbonyl compounds. Release of reducing carbohydrates may also be effected by other enzymes, such as glycosidases, or using chemical reactions, after scavenging of contaminating carbonyl compounds as described above.

B. Solid Support

The methods according to the present invention involve immobilisation of a reducing sugar to a solid support. Solid phase chemistry offers a number of advantages, such as easy handling, purification and concentration of immobilised compounds. However, not all reactions doable in solution can be performed on solid phases. The attachment to a solid support practically confer infinite size to each molecular entity.

This has the effect that the molecule reacts much more slowly in a bimolecular reaction than the same molecule would do in solution. Some reactions that may be carried out in solution with an acceptable yield simply will not perform on solid support.

The term "solid support" as used herein covers physical solids as well as insoluble polymers, insoluble particles, surfaces, membranes and resins, preferably the solid support is an insoluble polymer, an insoluble particle, a surface or a resin.

Thus the "solid support" may be an insoluble inorganic matrix (such as glass), an insoluble polymer (such as a plastic, for example polystyrene), an insoluble matrix consisting of parts of both organic and inorganic components (e.g. some hybrid silicates, such as compounds of the structure R—Si—O—), organic polymers in common use in solid-phase synthesis (polystyrenes, PEGA resins, PEG resins, SPOCC resins and hybrids thereof), polyethylene glycol chains (which can be soluble in certain organic solvents and made insoluble by the addition of other solvents). The solid may also be a metal (such as gold), an alloy, or a composite such as for example indium-tin oxide or mica.

Any of the above listed solid supports may additionally be coated with agents that have an affinity for carbohydrates, such as but not limited to aryl boronates or polymers thereof. Such coatings can increase the concentration of carbohydrate at the surface of the solid support, enhancing the rate and yield of capture.

Organic polymers used in solid-phase synthesis for example includes TentaGel (commercially available from Rapp polymere, Tübingen, Germany), ArgoGel (commercially available from Argonaut Technologies Inc., San Carlos, Calif.), PEGA (commercially available from Polymer Laboratories, Amherst, Mass.), POEPOP (Renil et al., 1996, *Tetrahedron Lett.*, 37: 6185-88; available from Versamatrix, Copenhagen, Denmark) and SPOCC (Rademann et al, 1999, *J. Am. Chem. Soc.*, 121: 5459-66; available from Versamatrix, Copenhagen, Denmark).

In one embodiment of the invention the solid support is a sensor, such as a surface acoustic wave sensor (such as any of the sensors described in Samoyolov et al. 2002, J. Molec. Recognit. 15: 197-203) or a surface plasmon resonance sensor (such as any of the sensors reviewed by Homola et al., 1999, Sensors and Actuators B, 54: 3-15). Such solid supports may be inorganic materials such as glass, metals such as gold, organic polymeric materials or hybrids thereof and may be covered various coatings such as proteins or polysaccharides, oligomers such as dendrimers or polymers such as polyacrylamide or polyethylene glycol. In a preferred embodiment the solid support is glass or PEGA resins.

In one embodiment of the present invention the solid support is coupled to a reference standard, which may facilitate quantification of immobilised reducing sugar. In particular, it is preferred that said reference standard is attached to the solid support (either directly or indirectly) by a cleavable linker, which could facilitate quantification of immobilised and released reducing sugar. In embodiments of the invention wherein the reducing sugar is immobilised to the solid support via a cleavable linker, it is preferred that the reference standard is immobilised to the solid support via an identical or similar cleavable linker.

The reference standard may be any detectable compound, for example the reference standard may or may not be a sugar, preferably however it is carbohydrate.

The amount of reference standard may vary, in general the solid support may comprise in the range of 20 to 500, preferably in the range of 50 to 200, such as in the range of 90 to 110-$NH_2$ groups per reference standard.

B. Spacer

According to the present invention the solid support is optionally coupled to a linker via a spacer. However, it is also comprised within the present invention that the solid support is directly coupled to the linker.

A spacer is a chemical entity in the range of 1 to 1000 atoms long. Preferably, said spacer is a linear or branched chain and/or a ring structure. The nature of the spacer may be hydrophobic or hydrophilic or have a mixture of these two properties. The group of spacers comprises molecules in common use in solid phase synthesis and on-bead, in-well or on-slide assays involving the detection of molecules attached via spacers to solid-supports. The skilled person will readily be able to identify a useful spacer for a given solid support.

The spacer is preferably an alkyl chain (more preferably a $C_1$ to $C_{1000}$ alkyl chain), which optionally may be branched, wherein said alkyl chain optionally is substituted at one or more positions by groups containing one or more of B, O, N, S, P, Si, F, Cl, Br or I. The spacer may also comprise one or more aryl residues which optionally may be branched or substituted in the same manner. In one preferred embodiment, the spacer is selected from the group consisting of amides and ethers. Thus the spacer may essentially consist of a chain containing one or more amide bonds (—CONH—), one more ethylene glycol units (—CH$_2$—CH$_2$—O—), or combinations of these units with the alkyl or aryl chains.

In one embodiment of the invention, the spacer preferably does not comprise either a primary or a secondary amine. In another embodiment of the invention any amines comprised within the spacer are capped.

B. Linker

The present invention relates to capture of reducing sugars onto solid supports covalently attached to a linker comprising a capture group. The linker serves to link the capture group, terminating in —NH$_2$, to the solid support optionally through a spacer. The linker may be any of a large variety of linkers such as those in common use in solid-phase organic synthesis.

The linker may either be a non-cleavable linker or a cleavable linker.

Non-cleavable linkers may for example be alkyl, aryl, ethers or amides, wherein any of the aforementioned may optionally be substituted. For example any of the aforementioned may be substituted with heteroatoms or they may contain, O-alkyl, alkyl, aryl or heteroatoms as branches. In one example the linker comprises or essentially consists of PEG and/or polyamide.

The linker may comprise a site where a reaction can be made to occur to sever the part containing the capture group (including the molecules it has captured and which have been optionally further modified) from the spacer and the solid support. Such linkers are referred to as cleavable linkers, and are in wide use in solid phase organic synthesis. Examples of cleavable linkers are known where the cleavage can be effected by electrophiles, nucleophiles, oxidizing agents, reducing agents, free radicals, acid, base, light, heat or enzymes.

Cleavable linkers may for example be acid labile (for example, the Rink amide as described in Rink, 1987, *Tetrahedrom Lett.*, 28: 387 and traceless silyl linkers as described in Plunkett et al., 1995, *J. Org. Chem.*, 60: 6006-7), base labile (for example, HMBA as described in Atherton et al. 1981, *J. Chem. Soc. Perkin Trans*, 1: 538), or photolabile (for example, 2-nitrobenzyl type as described in Homles et al., 1995, *J. Org. Chem.*, 60: 2318-2319). The linkers may be more specific and restrictive of the type of chemistry performed, such as silyl linkers (for example, those cleaved with fluoride as described in Boehm et al., 1996, *J. Org. Chem.*, 62: 6498-99), allyl linkers (for example, Kunz et al., 1988, *Angew. Chem. Int. Ed. Engl.*, 27: 711-713), and the safety catch sulfonamide linker (for example, as described in Kenner et al., 1971, *Chem. Commun.*, 12: 636-7). Enzyme cleavable linkers may for example be any of the enzyme cleavable linkers described in Reents et al., 2002, Drug Discov. Today, 7: 71-76, or any functionalised derivatives of the enzyme-labile protecting groups described in the review by Waldmann et al., 2001, Chem. Rev. 101: 3367-3396. Heat labile linkers may for example be of the type described in Meng et al., 2004, Angew. Chem. Int. Ed., 43: 1255-1260.

B. Capture Group

According to the present invention the linker comprises a capture group, wherein the capture group comprises at least one —NH$_2$ group. In a favourable format, the capture group terminates in an —NH$_2$ group that is attached to the linker through an optional group R. Thus the capture group preferably is of the structure R—NH$_2$. R may be a simple alkyl, aryl or substituted alkyl or aryl group. Preferably, R should contain a heteroatom directly attached to the —NH$_2$ group, to produce structures of the type linker-M-NH$_2$, wherein M is a heteroatom (i.e. not carbon), preferably M is selected from the group consisting of N, O and S. Especially favourable are compounds where M is a heteroatom, such as in the structures linker-O—NH$_2$, linker-NH—NH$_2$, linker-CO—NH—NH$_2$, linker-NH—CO—NH—NH$_2$, linker-S(O)$_2$NH—NH$_2$ and linker-S—NH$_2$.

A+B→C. Methods of Capture

The capture of the reducing sugar is done by reacting the —NH$_2$ group of the capture group with the reducing end of said reducing sugar, i.e. with the aldehyde or hemiacetal group. The reaction can occur at any pH values but is most favored in the range of pH 2-9. The methods may involve the addition of one or more additives, such as additives which may either facilitate or favourably alter the equilibrium between the open chain aldehyde form of the reducing sugar and the hemiacetal form of the reducing sugar (e.g. compound A, FIG. 1), wherein the open chain aldehyde form is preferred. The additive may for example be metal ions, boronates or silicates. The capture produces a species attached to the solid support through a covalent double bond (shown as C=N) where the C is derived from the sugar moiety and N from the capture group. This immobilized sugar may also be in equilibrium with its cyclic ring form, in particular if the reducing sugar was a pyranose, then the immobilised sugar may be in equilibrium with its cyclic 6-membered ring form (see for example compounds C and C' of FIG. 1), but it may also be in equilibrium with its 5-membered ring form if the appropriate OH group on the sugar is unsubstituted.

The capture reaction may be performed in any useful solvent. A person of ordinary skill in the art will readily be able to identify a useful solvent for any given compounds A and B. The solvent may for example be selected from the group consisting of water, aqueous buffer, organic solvents and mixed aqueous and organic solvents. The solvent may also be any of the aforementioned comprising one or more additives such as acids, bases, salts, divalent metal cations, detergents, complexing agents including inclusion-complex-forming molecules such as cyclodextrins or calixarenes, chelating agents (for example EDTA), borates, boronates or silicates.

In a preferred embodiment the amount of solid support (compound B of FIG. 1) added to the reaction is adjusted so that a molar excess of capture groups are present in relation to the reducing sugar, preferably said excess is large, such as at least 2 times, preferably at least 5 times, more preferably at least 10 times, such as at least 50 times, for example at least 100 times or more. This excess will ensure a more efficient capture of the reducing sugar.

The capture reaction may be carried out at any temperature, but preferably at temperatures in the range of 0 to 100° C.

C. Washing

Once the reducing sugar has been immobilised on the solid support through reaction with the capture group (step A+B→C of FIG. 1) the solid supports may be washed to remove non-covalently bound material. Accordingly, if the reducing sugar is provided in a solution comprising other compounds, in particular other compounds that do not comprise —NH$_2$ reactive groups, the reducing sugar may be purified from said solution. It is thus comprised within the present invention that the reducing sugar is provided in a non-purified form, such as in the form of a crude cellular extract or the like. It is also comprised that the reducing sugar may be produced from a purified or partially purified glycoprotein, glycolipid or glycoside by the action of an enzymes such as glycosidase or an amidase or through the cleavage of a glycosidic bond by chemical reagents.

The skilled person will readily be able to identify suitable washing conditions for a given immobilised sugar (compound C, FIG. 1). The washing may for example be done with any of the above-mentioned solvents optionally comprising any of the above-mentioned additives in addition to detergents and denaturing agents. The washing my be performed at any temperature, but preferably at temperatures in the range of 0-100° C.

C→D. Capping

The solid support coupled to the immobilised sugar (such as compound C of FIG. 1) still contains unreacted free —$NH_2$ groups and can be subjected to unique manipulations that increase the scope of its utility.

In one preferred embodiment of the invention, subsequent to immobilisation of the reducing sugar, unreacted —$NH_2$ groups are capped by a capping agent, such as an acylating agents (e.g. acetic anhydride) or other nitrogen-reactive agents well known in the art, under conditions where the C=N bond of C does not react. After capping the solid support will no longer comprise any free amine groups, but only capped nitrogen atoms (N(H)CAP) of very low reactivity towards electrophiles. The product of the capping of compound C has for example the general structure D (see FIG. 1) containing an —R—N(H)CAP group, wherein the (H) may or may not be present depending on the structure of the CAP group.

Thus if the C=N bond linking the sugar to the solid support is reduced to an —NH—, it will be a formally $SP^3$-hybridized nitrogen atom in the sequence R—NH—$CH_2$—. Specific reactions may thus be directed to this group allowing specific and stoichimetric reactions at the reducing sugar.

Preferably the capping agent specifically reacts with the remaining —$NH_2$ groups, without substantially reacting with the C=N functionality. Such reagents are well known in the art an include common acylating agents used for amid bond formation, e.g. acetic anhydride, other alkanoic acid anhydrides, aromatic anhydrides (e.g. benzoic anhydride), cyclic anhydrides (e.g. succinic anhydride, phthalic anhydride), other active esters such as N-hydroxysuccinimide esters, pentafluorophenyl esters and a variety of active esters in common use in amide bond formation including in the solid phase synthesis of peptide bonds. The —$NH_2$ groups may alternatively be capped by adding the corresponding free acids and an in-situ activating agent such as DCC, in common use in peptide-bond formation thereby creating an active ester in situ. Other reagents known to be reactive towards —$NH_2$ groups can be used, such as alkyl isothiocyanates (R—NCS), aryl isothiocyantes (Ar—NCS), alkylating agents R-L (where L is a leaving group typically from the series Cl, Br, I, $OS(O)_2$R' where R'can be alkyl or aryl), Michael acceptors such as alpha-beta unsaturated carbonyl compounds (CHR=CH—CO— where R can be H, alkyl or aryl or substituted alkyl or aryl) or alpha-beta unsaturated sulfones (CHR=$CHS(O)_2$R' or Ar where R can be H, alkyl or aryl or substituted alkyl or aryl), sulfonating agents (such as $RSO_2Cl$) and derivatives thereof. In a similar manner, the —$NH_2$ groups can be capped by reaction with active esters of carbonates of the general formula RO—C(O) L, where L is described as above.

D→E. Reduction

In a preferred embodiment of the invention, the C=N bond linking the sugar to the linker (for example compound D of FIG. 1) is reduced using a reducing agent. The C=N bond may be reduced by a variety of well known reducing agents, preferably the reducing agent is capable of saturating the double bond while placing a hydrogen atom on the N.

Of special value are boranes or borohydrides comprising a BH bond, examples include $NaBH_4$, $NaCNBH_3$, and $BH_3$ complexes such as $BH_3$-pyridine, $BH_3$-dimethylsulfide or the like. Silanes with the structures $R_3SiH$ can also be used, such as silanes comprising SiH bonds, as can hydrogen transfer agents such as diimides, or homogeneous hydrogenation catalysts or hydrogenation catalysts comprising a metal-H bond.

The reduction results in a reactive sugar containing the structure SugarCH—NH— preferably linked to a solid support via a linker and optionally a spacer. In general, if the reducing sugar was an aldehyde, then reduction will result in a compound of the structure Sugar$CH_2$—NH—. If the reducing sugar was a ketone, then the reduction will result in a compound of the structure SugarCH—NH—.

The products of the reduction are for example of the general structure E (FIG. 1) containing a formally $SP^3$ hybridized N atom.

C→$C_{red}$→E

In another preferred implementation of the method, the order of the capping and reduction steps is reversed. Reduction of the C=N bond in compound C (FIG. 1) can be effected by any of the reagents described in D→E above to produce a compound of the structure $C_{red}$ (FIG. 1). The reduction may also be performed in situ, meaning that a reducing agent (such as $NaCNBH_3$) may be added to the solid support (e.g. compound B) simultaneously with the reducing sugar so that the C=N bond is reduced as it forms producing also $C_{red}$. It is thus comprised within the present invention that the sample comprising the reducing sugar may be incubated with the solid support and the reducing agent simultaneously. Thus, reduction of C=N bonds (step v) will be performed immediately following reaction of the reducing sugar with the —$NH_2$ group of the solid support (step iii). The free —$NH_2$ groups in $C_{red}$ may then be capped using any of the reagents described in C→D above under conditions that do not cause reaction with the SugarCH—NH-moiety. In particular, in this embodiment of the invention it is preferred that the capping agent preferentially reacts with primary amino groups over secondary amino group. It is also preferred that reaction temperature and time are adjusted to yield preferential reaction with primary over secondary amino groups. Virtually all compounds that react with amino groups react more quickly with primary amino groups than with more substituted amino groups, but this is especially the case when such compounds are sterically large, such as for example active benzoyl esters, isopropanoic acid active-esters, pivaloyl active-esters, Boc anhydride or Boc-azide and the like. Useful compounds and conditions for preferential reaction with primary amino groups over secondary amino groups are described in Greene et al. 1999, Protective Groups in Organic Synthesis, $3^{rd}$. Ed., Chaper 7, pp. 503-653. Other very preferred capping agents are NHS-esters or sterically hindered pentafluorophenyl (PFP) esters or tetrafluorophenyl (TFP) esters.

E→F. Adding TAGs

Compound E, FIG. 1, obtained by either of the above routes, contains solids linked to a capped nitrogen atom (N(H)CAP) of very low reactivity towards electrophiles and a formally $SP^3$-hybridized nitrogen atom in the sequence SugarCH—NH—R. Reaction of E with suitable nitrogen-reactive functional groups (preferably the nitrogen-reactive functional group is a mild electrophile) therefore results in the exclusive, or near exclusive, addition of the electrophile to the $SP^3$ nitrogen atom effectively adding a molecular structure, herein described as "TAG", or another derivatising agent onto the nitrogen to which the sugar is attached. The product of the addition of a TAG is shown as F in FIG. 1.

Throughout the description the term "nitrogen-reactive group" is used to describe reactivity towards a formally $SP^3$-hybridized nitrogen, such as in compounds of the structure R—NH—R', for example amines, wherein R and R' independently are alkyl, or aryl (optionally substituted) or compounds wherein R' has an heteroatom such as O or N attached to the —NH— such as in hydroxylamine derivatives (R—NH—OR') or hydrazine derivatives (R—NH—NH—R').

The identity of the derivatising agent (for example a TAG), i.e. the specific chemical structure of the derivatising agent, may be selected by the user. For addition to the $SP^3$ nitrogen in E, the derivatising agent (for example the TAG) should itself comprise an nitrogen-reactive functional group designated "X" in FIG. 1, Preferably the TAG should contain an electrophile, or be attached to an nitrogen-reactive functional group X. Preferably the derivatising agent is of the general structure TAG-X (see FIG. 1), wherein X is a nitrogen-reactive functional group. Preferably X is any mild electrophile that is reactive with $SP^3$ nitrogen atoms, but preferably mild electrophiles that react poorly with the —OH groups present on the sugar. Such mild electrophiles include isothiocyanates (TAG-NCS), active esters (TAG-C(O)-L) where L is a leaving group commonly used in amide bond formation such as in the synthesis of peptide bonds, carboxylic acids (TAG-COOH) which can be activated to active esters in situ by methods commonly used in amide bond formation such as in the synthesis of peptide bonds, alkylating agents (TAG-L) where L is a leaving group preferably but not exclusively from the series Cl, Br, I, $OS(O)_2R$ where R can be alkyl or aryl, TAGs comprising Michael acceptors (typically containing the sequence —CR=CH—C(O)—) or alpha-beta unsaturated sulfones (—CR=CH—$S(O)_2$—) and derivatives of any of the aformentionned, aldehydes or ketone that may react with the sugar$CH_2$—NH-amino group by reductive amination, or substituted haloaromatic groups where the aromatic ring bears electronegative groups such as nitro groups, for example as in the Sanger reagent 1-fluoro-2,4-dinitrobenzene or the 4-halo-7-nitro-2-oxa-1,3-diazole (NBD) reagents where the halogens preferably F or Cl.

The TAG may for example be a fluorescent moiety, a mass spectrometry TAG, a first binding partner capable of binding to a second binding partner, a nucleic acid wherein any of the aforementioned TAGs preferably comprises or are attached to an nitrogen-reactive functional group. In particular the TAG may be any of the TAGs described in more detail herein below, wherein any of these TAGs may be attached to any of the aforementioned nitrogen-reactive functional groups.

An example of a compound which may be obtained by adding a TAG to compound E is shown as F in FIG. 1.

F. Washing

In one embodiment the tagged sugar (e.g. compound F, FIG. 1) is washed prior to any further manipulations. Thus any amount of unbound TAG is removed. Washing may easily be accomplished because the tagged sugar is immobilised on a solid support.

After washing, only covalent bound TAG will be present. Thus the amount of TAG will be correlatable to the amount of immobilised sugar. Accordingly, by determining the presence of TAG, the amount of immobilised sugar may be determined. If essentially all reducing sugar in a given sample was immobilised, the methods therefore in one aspect allow determining the amount of reducing sugar present in a sample.

The skilled person will readily be able to identify suitable washing conditions for a given tagged, immobilised sugar (e.g. compound F, FIG. 1). The washing may for example be done with a solvent selected from the group consisting of water, aqueous buffer, organic solvents and mixed aqueous and organic solvents. The solvent may also be any of the aforementioned comprising one or more additives such as salts, divalent metal cations, detergents, complexing agents including inclusion-complex-forming molecules such as cyclodextrins or calixarenes, chelating agents (for example EDTA), borates, boronates or silicates. Furthermore, the solvent may optionally comprise detergents and denaturing agents. The washing my be performed at any temperature, but preferably at temperatures in the range of 0-100° C.

H. Cleavage of Cleavable Linker

When the linker used is a cleavable linker, then methods of the invention may comprise a step of cleaving said cleavable linker thereby releasing captured sugar. Preferably the cleavage is performed subsequent to addition of a derivatising agent, such as a TAG (added using TAG-X) or a tether-Y (added using X-tether-Y) to the —NH— group of the immobilised sugar. Thus a tagged sugar (compound G or compound J in FIG. 1) may be released into solution from F or from 1, respectively. G consists of a sugar portion that bears a TAG on the Nitrogen atom which is attached to the residue (if any) of the linker that remains after cleavage, and for simplicity is denoted as sugar-TAG. J consists of a sugar portion that bears a tether on the nitrogen atom, which is attached to the residue (if any) that remains after cleavage. The tether may optionally be linked to a TAG.

However, the cleavable linker may be cleaved at any desirable time within the method.

If the TAG added to compound E has beneficial spectroscopic properties such as fluorescent properties, the amount of sugar-TAG (compound G, FIG. 1) can be quantitated in solution. Furthermore, the sugar-TAG (compound G, FIG. 1) can be subjected to analytical separation techniques such as HPLC or CE, and if more than one sugar is present, the individual components can be separated, their relative ratios determined, and they can be identified if authentic standards are available, and they can be quantitated. They can also be used as ligands that may bind to carbohydrate-recognizing proteins, thus providing information on the structure of either the carbohydrate or the protein.

If the TAG is a structure giving the sugar-TAG properties that are beneficial to the practice of mass-spectrometry, either due to increased sensitivity, simplification of spectral interpretation, or permitting the performance of differential analysis using isotope encoding, then the sugar-TAG released into solution can be favourably analyzed by mass-spectrometry.

F. TAGs with Spectroscopic Properties

In one preferred embodiment of the invention the TAG added to e.g. compound E or compound H has beneficial spectroscopic properties. Preferably, the TAG with the beneficial spectroscopic properties is added to e.g. compound E using a derivative of the structure X-TAG, wherein X is a nitrogen reactive functional group, such as any of the nitrogen reactive functional groups described herein above in the section "E→F Adding TAGs". By beneficial spectroscopic properties is meant that the TAG can easily be visualised, for example by spectrometry. Thus the TAG may for example be spectroscopically detectable. In a preferred embodiment the TAG is a fluorescent TAG. Examples of such tagging include the reaction with isothiocyanates (e.g. FITC, TRITC), active esters, Michael acceptors, alpha-beta-unsaturated sulfonyls (specifically vinyl sulfones) and alkylating agents such as alkyl halides and tosylates, an halo-aryl compounds such as for example the Sanger reagent The product of addition of such a TAG (for example compound F of FIG. 1) can absorb and re-emit light that can be detected. The number of such TAGs present on F will reflect the number of sugar molecules A added to B and captured to produce C. The number of reducing sugar molecules (A) originally present in a sample can therefore be estimated by the fluorescence of compound F, provided that the provided solid supports (compound B) comprise an excess of capture groups. TAGs other than fluorescent molecules can also be used. These can include radioactive TAGs, phosphorescent TAGs, chemiluminescent TAGs, UV-absorbing TAGs, nanoparticles, quantum dots, coloured compounds, electrochemically-active TAGs, infrared-active TAGs, TAGs active in Raman spectroscopy or Raman scattering, TAGs detectable by atomic force microscopy or TAGs comprising metal atoms or clusters thereof.

If the solid support of compound F is a sensor, such as a surface acoustic wave sensor or a surface plasmon resonance sensor, then addition of such a species that binds specifically to the TAG can result in the production of a signal that is proportional to the TAG and therefore to the number of sugar molecules. An example is when the TAG is a biotin residue, commonly introduced by reaction with an active ester of biotin. Addition of an avidin-protein to compound E, when the TAG is a biotin residue, can result in signal that is readily detected and reported by the sensor. Other examples of sensors that can be used to detect the binding of second binding partners to immobilized TAGs include but are not limited to piezoelectric sensors, amperometric sensors, surface plasmon fluorescence spectroscopy sensors, dual polarization interferometry (DPI) sensors, wavelength-interrogated optical sensors (WIOSs), impedence sensors, optical waveguide grating coupler sensors, acoustic sensors and calorimetric sensors.

Once the sugar has been attached to a TAG with spectroscopic properties, then said spectroscopic properties may be determined. The optical properties may be determined for sugars still immobilised on the solid support (such as for compound F or I of FIG. 1) or for sugars released to solution (for example for compound G or J of FIG. 1). The latter requires that the linker is a cleavable linker. Depending on the nature of the TAG with spectroscopic properties, said properties may be determined using conventional methods, such as spectrometry. Thus the methods of the invention may comprise the step of detecting the TAG attached to the sugar by spectrometry.

F. Mass-Spectrometry Tags

In one embodiment of the invention, the TAG is a mass spectrometry TAG. Said mass spectrometry TAG is preferably added by a reagent of structure X-TAG, wherein X is a nitrogen-reactive functional group, such as any of the nitrogen-reactive functional group mentioned herein above in the section "Adding TAGs". The term "mass spectrometry TAGs" as used herein refers to molecules that improve the detection and structural characterization of the products by mass spectrometry, preferably after cleavage from the solid support (as described herein above in the section "Cleavage of cleavable linker"). Examples include the introduction of a bromine label which imparts a characteristic isotope pattern in the mass-spectrum. Such a bromine label may be added, for example, by addition of p-bromophenyl isothiocyanate to compound E producing a compound of structure F where the TAG contains a bromine atom. The usefulness of bromine-containing labels in the mass-spectrometry of carbohydrates has been described for example in Li et al., 2003, Rapid. Commun. Mass Spectr., 17: 1462-1466. Another example includes introduction of molecules that impart either positive charges or negative charges for enhanced detection in either positive-ion mode or negative-ion mode of mass/charge separation. Another example includes the introduction of molecules that improve performance or sensitivity in electrospray, MALDI or other techniques of ionization common in the practice of mass spectrometry. Yet another example includes the introduction of stable isotope-labeled molecules that allow quantitation of the labelled species by mass-spectrometry. Useful methods for isotope labelling are for example reviewed in Tao et al., 2003, Current Opinion in Biotechnology, 14: 110-118.

Once the sugar has been attached to a mass spectrometry TAG, then the tagged sugar (F or G or I or J, FIG. 1) may be detected by mass spectrometry. Mass spectrometry may be performed on sugars still immobilised on the solid support (such as for compounds F and I of FIG. 1), but preferably is performed on sugars released to solution, for example by cleavage of a cleavable linker (for example for compounds G or J of FIG. 1). It is thus preferred that the linker is a cleavable linker. The skilled person will be able to perform a suitable mass spectrometry depending on the nature of the mass spectrometry TAG. Thus the methods of the invention may comprise the step of detecting the sugar attached to the mass spectrometry TAG by mass spectrometry.

F. Binding Partner TAGs

In another preferred embodiment of the present invention the TAG is a first binding partner, capable of specific interaction with a second binding partner, wherein said first binding partner is added to for example compound E (or to compound H) through the reaction with a reagent of structure X-TAG, wherein X is a nitrogen-reactive functional group (e.g. a "derivatising agent"). The second binding partner is preferably labelled with a detectable label, such as a dye, a fluorescent label, a radioactive isotope, a heavy metal or an enzyme. The first binding partner may for example be a molecule that is a ligand for a protein useful in the detection of the resulting immobilized ligand, either stoichiometrically or following amplification. The first binding partner may also be a protein and the second binding partner a ligand for said protein.

Examples of binding partners include ligand-protein pairs in common use in ELISA assays. For example compound E may be reacted with a biotinylation reagent, and after washing, detecting the now immobilized biotin with streptavidin (or other avidins) that is directly labelled with a detectable label, such as with a fluorescent TAG, a radioactive isotope or a heavy metal, or with streptavidin (or other avidins) that is conjugated to an enzyme such as horseradish peroxidase that can catalyze a chemical reaction that results in the production of a signal that can be detected by spectrometry.

Other examples of binding partners are antibody-epitope pairs. Thus the one binding partner could comprise an epitope and the other binding partner could be an anti-body capable of binding said epitope with high affinity, preferably an antibody specifically binding said epitope.

F. Nucleic Acid Tags

In another embodiment of the invention the TAG is a nucleic acid. Nucleic acids according to the invention may be any nucleic acid, such as DNA or RNA, or analogues thereof such as LNA, PNA, HNA or the like. Preferably the nucleic acid is DNA, preferably a DNA oligomer. Preferably, said DNA is derivatised with an nitrogen-reactive functional group, such as any of the nitrogen-reactive functional groups mentioned herein above in the section "Adding TAGs". It is preferred that the sequence of said nucleic acid TAG is known or at least partially known, which will enable the skilled person to readily detect said TAG using standard methods.

The nucleic acid TAG may be any desirable length, preferably at least a length which will allow specific detection. Thus preferably the nucleic acid is at least 6 nucleotides, more preferably at least 10 nucleotides, for example in the range of 10 to 5000 nucleotides long.

After addition of a nitrogen-reactive nucleic acid TAG to the sugar, then the nucleic acid, such as the DNA oligomers can then be detected directly on the solid support by hybridisation to their complementary nucleic acids or essentially complementary nucleic acid. By essentially complementary nucleic acids, is meant a nucleic acid, which may hybridise to a given nucleic acid under stringent conditions as for example described in Sambrook et al., 1989, in "Molecular Cloning/A Laboratory Manual", Cold Spring Harbor. Preferably, said complementary nucleic acids may be attached to a detectable label. Said detectable label may for example be a fluorescent label or a radioisotope or an enzyme, preferably a fluorescent label. Thus, the nucleic acid TAG may for example be detected by hybridisation to their complementary fluorescently-labeled DNA. Alternatively, a nucleic acid TAG may be amplified using conventional methods known in the art, such as Polymerase Chain Reaction (PCR) or ligase chain reactin. Thus, the immobilised nucleic acid TAG may be subjected to PCR reactions to amplify the immobilized DNA oligomer which can be measured in solution by a variety of well know techniques for quantification in PCR. This process has particular value in the indirect detection and quantification of very low amounts of SugarCH—NH-Linker-Spacer-Solid present on the solid support. Alternatively, the Sugar bound to DNA may be released to solution by cleavage of the linker and thereafter amplified in solution by for example PCR or detected in solution by virtue of specific hybridisation to essentially complementary nucleic acids.

E→H Tethers

The derivatising agent according to the present invention may also be a tether coupled to at least two functional groups. Such bifunctional reagents will in general be of the structure X-tether-Y or X-tether-$Y_p$, wherein X is an nitrogen-reactive functional group and Y is a second reactive functional group and $Y_p$ is a latent reactive functional group or a protected reactive group Y. The product of the reaction of compound E with X-tether-Y (or X-tether-Yp) may for example have the general structure of compound H of FIG. 1. The second reactive functional group Y may be reactive to any of the types of reagents in use in solid-phase synthesis. For example, the N in SugarCH—NH-Linker-Spacer-Solid can be reacted with bifunctional reagents (X-tether-Y) where one function reacts by making a bond to the immobilized nitrogen (the nitrogen reactive functional group X) and the other function can either be, or can be converted to (by for example unmasking, deprotection or further reaction) a second reactive functional group Y.

The tether may be any useful tether, for example alkyl, alkenyl or alkynyl (which may be linear, branched or cyclic), aryl or any of the aforementioned comprising amide bonds (NC(O)R) or ethyleneglycol groups (—$CH_2CH_2$—O—) or substituted with heteroatoms and their derivatives.

The second functional reactive group Y may for example be selected from the group consisting of thiols, carboxyl groups, activated carboxyl groups, disulfides, activated disulfides, alkylating agents, alkenes, alkynes, aldehydes, ketones and azides. The alkylating agent may for example be an alkyl halide or an alpha-halo carbonyl group. $Y_p$ may for example be protected amines or protected derivatives of any of the aforementioned groups Y. Thus $Y_p$ may for example be selected from the group consisting of protected amines, protected thiols, protected carboxyl groups, protected aldehydes and protected ketones. Protected reactive groups are herein denoted $Y_p$, wherein $Y_p$ may be deprotected to yield a functional reactive group Y. Useful protecting groups can be found in Greene et al., 1999, "Protective Groups in Organic Synthesis", 3rd. Ed., John Wiley and Sons, New York, specifically for carbonyl groups (chapter 4, pp. 293-368), for carboxyl groups (chapter 5, pp. 369 453-), for thiols (chapter 6, pp. 454-493) and for amino groups (chapter 7, pp. 494-653). Examples of protected amines include, but are not limited to, those in common use in solid-phase peptide synthesis, such as Fmoc, Boc, Alloc, p-nitrobenzyloxycarbonyl, trityl and substituted trityl, o-nitrobenzyloxycarbonyl, N-sulfenyl or azido. However, the second reactive functional group may be any functional groups Y, or protected functional groups ($Y_p$) that have been made to react on the solid phase, such as examples well known in the art of solid phase synthesis and the coupling of small molecules to solid supports and surfaces. These functionalized groups can then directly, or after deprotection to reactive species, capture a second derivatising agent comprising a functional group (Z) capable of reacting with the second functional group Y.

If Y in compound H contains an $NH_2$ group, or on deprotection can be made to contain an $NH_2$ group, then any of the amine reactive reagents described in E-goes-to-F (for example, isothiocyanates) can be used to add a TAG to produce compounds of the general structure I (FIG. 1).

The second derivatising agent made to react with any of the functional groups Y in compound H (FIG. 1) may for example be spectroscopic TAGs or any of the TAGs mentioned above in section E→F, wherein said TAGs in stead of a nitrogen reactive group, comprises or are derivatised with a functional group (Z) capable of reacting with Y. They may also be small molecules like drugs, imaging agents, peptides, proteins, enzymes and other molecules exhibiting biological activities, nucleic acids such as DNA or RNA Said small molecules, imaging agents, peptides or nucleic acids preferably comprises or are attached to a functional group Z, capable of reacting with the given second functional reactive group Y. The skilled person will readibly be able to identify useful functional groups Y and Z. The second derivatising agent may also be any of the above-mentioned TAGs described above in the sections "TAGs with Spectroscopic properties", "Mass spectrometry TAGs", "Binding partner TAGs" and "Nucleic acid TAGs", wherein said TAGs in place of a nitrogen reactive functional group contains a functional group Z capable of reacting with the functional group Y. The functional group attached to the tether in H (FIG. 1) may also be a latent or protected group ($Y_p$) that can be converted by chemical or enzymatic reaction into Y which may then react further as described above. If this latent group can be converted to a primary or secondary amine (i.e. Y will comprise the structure —$NH_2$ or —NH—), then any of the amine-reactive species described in E→F above may be added to produce tagged compounds of the structure I.

The methods of the invention may therefore comprise the step of vii. Reacting the —NH— group of the reactive sugar with a bifunctional reagent of the structure X-tether-Y or X-tether-$Y_p$, wherein X is a nitrogen-reactive functional group and Y is a second reactive functional group and $Y_p$ is a latent functional group that can be converted to or deprotected to a reactive functional group Y, thereby obtaining a sugar covalently attached to said tether-Y or said tether-$Y_p$.

This step is preferably performed using compound E of FIG. 1 as starting material. Thus this step may for example generate a compound of the general structure H of FIG. 1.

In embodiments of the invention wherein the bifunctional reagent is of the structure X-ether-$Y_p$, then preferably, the method furthermore comprises the step of converting or deprotecting $Y_p$ to obtain a reactive functional group Y. This step may be performed before or after reacting X with —NH—, preferably it is performed subsequent to reacting X with —NH—.

In addition the methods of the invention may furthermore comprise the steps of viii. providing a second derivatising agent comprising a functional group (Z) capable of reacting with Y ix. reacting the functional groups Z and Y, thereby covalently attaching the second derivatising agent to the sugar via a tether and the first derivatising agent.

Alternatively, the methods of the invention may further comprise the step of:

viii. providing a particle selected from the group consisting of eukaryotic cells, prokaryotic cells, microbial organisms, micelles, phages, vira and nanoparticles, wherein the particle comprises a functional group (Z) capable of reacting with Y.

ix. reacting the functional groups Z and Y, thereby covalently attaching the particle to the sugar via the tether and the agent.

Step ix. may thus generate a compound of the general structure I outlined in FIG. 1 where the TAG is a particle. Provided that the linker is a cleavable linker, the methods may further comprise the step of cleaving the linker thereby for example generating a compound of the general structure J of FIG. 1.

The product of the reaction of SugarCH—NH-Linker-Spacer-Solid (e.g. compound E of FIG. 1) with bifunctional reagents X-tether-Y for example has the general structure H and may contain, or can be made to contain, further reactive groups that can form covalent bonds to assemblies larger than molecules: for example bacteria, phage, yeast, micelles, viruses, nanoparticles or eukaryotic or prokaryotic cells. Cleavage of the linker then results in species of the general formula SugarCH—N(assembly)-Linker, effectively adding the sugar to the assembly. Thus, the sugar can in principle be transferred from a solid support to an assembly.

Enzyme Treatment

If the solid support is biocompatible, i.e. permits contact with biological macromolecules like enzymes without significantly altering their activities, then the immobilised sugar molecule can be acted on by enzymes that will alter its structure. The immobilised sugar molecule may for example be a compound of any of the general structures C, $C_{red}$, D, E, F, H or I of FIG. 1.

Non-limiting examples of biocompatible solid supports includes glass, PEGA, SPOCC or polysaccharide gels. Within this embodiment it is preferred that the linker is relatively long, and thus it is preferred that the linker comprises at least 2 atoms, preferably at least 6 atoms, more preferably the linker comprises a chain of at least 6 atoms, for example the longest chain of atoms within the linker is at least 6 atoms long, such as in the range of 6 to 1000 atoms long. It is also preferred that the linker is hydrophilic.

It is also possible to contact the sugars liberated into solution by cleavage of a cleavable linker, such as the compounds G or J of FIG. 1 with biological macromolecules, such as enzymes.

The enzymes can belong to any class that can act on carbohydrates, for example glycosidases, glycosyltransferases, and enzymes that modify the alcohol groups by acylation, phosphorylation, sulfation or oxidation. Alternatively, if the sugars are already substituted on —OH groups, such as acylated, phosphorylated or sulphated, then deacylases, phosphatases and sulfatases can alter their structures. Thus the methods of the invention may furthermore comprise the step of contacting the sugar (for example any of the compounds C, $C_{red}$, D, E, F, G, H, I or J of FIG. 1) with one or more enzymes selected from the classes of glycosyltransferases, sulfatases, phosphorylases, sulfotransferases, phosphotransferases, glycosynthases and transglycosidases, thereby converting said sugar into a new structure. In a preferred embodiment the methods furthermore comprise the step of contacting the sugar (for example any of the compounds C, $C_{red}$, D, E, F, G, H, I or J of FIG. 1) with one or more glycosidases, thereby generating a new reducing sugar, provided that the first sugar is a substrate for said glycosidase(s).

An example would include the incubation of uncapped Sugar-C=N-Linker-Spacer-Solid (for example, compounds C of FIG. 1), which still contains free —$NH_2$ groups, with an exoglycosidase causing the decrease in the length of the sugar by one monosaccharide residue. The cleavage of this monosaccharide residue leaves an oligosaccharide attached to the solid support that is one sugar unit shorter, and produces a reducing sugar which can be captured by the same or a different solid support, such as a solid support of the general structure B in FIG. 1, which can subsequently be submitted to any of the manipulations described above in B to J.

Thus the methods of the invention may furthermore comprise the steps of a) providing one or more enzymes that can act on carbohydrates b) contacting the sugar with said one or more enzymes These steps may be performed at any given time during the method. The enzymes may be any of the enzymes described in the present section.

In a particular embodiment the enzyme is a glycosidase and the method described herein above in the summary section comprises the further steps of:

iii.a) providing one or more glycosidases that can act on carbohydrates iii.b) contacting the sugar with said one or more glycosidases, thereby generating a new reducing sugar, provided that the first sugar is a substrate for said glycosidase(s).

iii.c) immobilising newly generated reducing sugar(s) on a solid support.

The steps iii.a-iii.c may be carried out following step iii. of the method outlined in the section "Summary of the invention" herein above. However, the steps iii.a to iii.c may also be carried out following any of steps iv, v, vi or vii of said method. Accordingly, steps iii.a-iii.c may be carried out on any of the immobilized sugars exemplified by structures C, $C_{red}$, D, E, F, H or I of FIG. 1.

In particular, said newly generated reducing sugars may be immobilised to free —$NH_2$ groups of the same solid support or on another solid support. Said other solid support may for example either be unsubstituted or carry an immobilised reference standard. It is preferred that said other solid support is a solid support as described herein above, and that the solid support is attached to a linker (optionally via a spacer), wherein said linker comprises a capture group (see detailed description of linkers, capture groups and spacers herein above).

Of particular value is the reduction and fluorescence labeling of the glycosidase product and the released monosaccharide on the same or a different solid support, for purposes of obtaining structural information. A specific example includes the capture of Gal-GlcNAc-Gal-Glc (lacto-N-tetraose, LNT) on $NH_2$-Linker-Spacer-Solid of structure B (FIG. 1), incubation of the captured and immobilized LNT (an example of a compound of structure C of FIG. 1) with beta-galactosidase followed by capture of the released galactose on the same solid support (C) to yield a mixture of unreacted Gal-GlcNAc-Gal-GlcC=N-Linker-Spacer-Solid, and the products of the reaction which are GlcNAc-Gal-GlcC=N-Linker-Spacer-Solid and Gal-C=N-Linker-Spacer-Solid. Capping, reduction, fluorescence tagging with TRITC and cleavage form the solid as described in step F→G above then allows confirmation that the immobilized LNT had a terminal beta-galactose residue, by co-migration of the trisaccharide and monosaccharide products with known standards.

Many useful glycosidases are described in the art, for example any of the glycosidases described in U.S. Pat. No. 5,100,778 or WO92/19974 may be employed with the present invention.

If the solid support is biocompatible, then the unreacted —$NH_2$ groups in Sugar-C=N-Linker-Spacer-Solid (e.g. compound C, FIG. 1) can be capped (for example with acetic anhydride as described in C→D above) and then exposed to carbohydrate-active enzymes, or further reduced to SugarCH—NH-Linker-Spacer-Solid (as described in section D→E above) and then exposed to carbohydrate-active enzymes. Alternatively, compound C of FIG. 1 can be reduced to $C_{red}$ and then exposed to carbohydrate active enzymes. The SugarCH—NH-Linker-Spacer-Solid (e.g. compound E, FIG. 1) can be further tagged (as described in sections E→F herein above) to yield SugarCH—N(TAG)-Linker-Spacer-Solid (e.g. compound F, FIG. 1), and then exposed to carbohydrate-active enzymes. In any of these processes, the product of the enzyme reaction that remains attached to the solid support can be further manipulated according to the methods of the invention or cleaved by reaction at the linker, for further analysis. Any product of the enzyme reaction that results in cleavage of fragments of the immobilized sugar will appear in solution, where it may be further investigated using established techniques of analytical chemistry or, in the case where it is itself a reducing sugar, may be subjected to the manipulations described for the generic sugar A in FIG. 1.

The individual sugars may be detected by capillary gas chromatography (GC), microcolumn supercritical fluid chromatography (SFC), microcolumn liquid chromatography (LC), high performance liquid chromatography (HPLC), high performance capillary electrophoresis (HPCE), ion-exchange chromatography or mass-spectrometry. Detection of individual sugars may be done before or after labelling with a derivatising agent, and either in solution or on the solid phase.

Detection Agents

In one embodiment of the invention, the method comprises the steps of
 viii. contacting the sugar with a detection agent capable of associating with said sugar
 ix. detecting the detection agent Preferably, said sugar is immobilised on a solid support as described herein above, and thus for example a compound of the general structure C, $C_{red}$, D, E, F, H or I of FIG. 1 may be contacted with said detection agent. It is also possible that said sugar has been released from the solid support by cleavage of a cleavable linker, as thus a compound of the general structure G or J may also be contacted with said detection agent.

The detection agent may be any agent capable of associating with said sugar. Preferred detection agents are compounds capable of associating with sugars with much higher affinity than with any other compounds, such as compounds having at least a 2-fold, such as at least a 5-fold higher affinity for sugars, than for any other compound.

In addition it is preferred that said detection agent is directly or indirectly detectable by a method known to the skilled person. For example the detection agent may itself be for example a fluorescent or coloured compound. The detection agent may also be a compound for which easy detection methods are available.

In one embodiment of the invention the detection agent comprises an aryl boronate or heteroaryl boronate where the aryl moiety is substituted with a spectroscopically active group such as a fluorescent TAG or any of the other detectable TAGs described herein above in the section "F. TAGs with spectroscopic properties".

In another embodiment the detection agent is a polypeptide, preferably a polypeptide selected from the group consisting of lectins, selectins and other carbohydrate binding proteins, toxins, receptors, antibodies and enzymes. When the detection agent is a polypeptide, said polypeptide may be coupled to a detectable label, such as an enzyme or a fluorescent compound. The polypeptide may also be detected by the aid of antibodies or similar high affinity compounds.

EXAMPLES

The following are illustrative examples of the methods of the invention and should not be considered as limiting for the invention. Unless otherwise clear from the context, capital letters A, B, C, $C_{red}$, D, E, F, G, H, I and J refers to the general structures outlined in FIG. 1.

Experimental

1. Examples of A

Reducing Sugars Used in the Present Work

The structures of the reducing sugars captured by solid supports B are shown in FIG. 2. These included the monosaccharides D-Glc (1) and D-Gal (2), the disaccharide N-acetyl-lactosamine (LacNAc, 3), the trisaccharide maltotriose (maltotriose G3, 4) and the tetrasaccharide lacto-N-tetraose (LNT, 5). Samples 6 and 7 contained mixtures of the monosaccharides Fuc:Man:GalNAc in ratios of 2:3:1 and 1:3:2, respectively. Sample 8 contained a 1:1 mixture of Gal (2) and LNT (5). Sample 9 contained an approximately equimolar mixture of maltobiose (G2), maltotriose (G3), maltotetraose (G4), maltopentaose (G5), maltohexaose (G6) and maltoheptaose (G7). Sample 10 consisted of the N-linked oligosaccharide chains released from ribonuclease B (Sigma) by the action of PNGase F (product number 1365177, Boehringer Mannheim GmbH, Germany).

Figure 3:
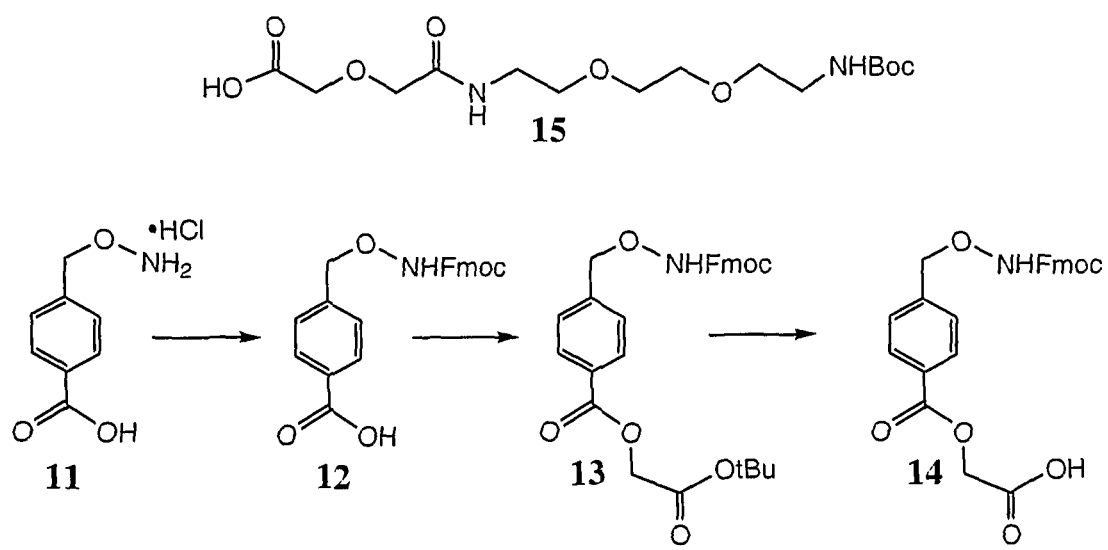
FIG. 3. Synthesis of a linker (14) and structure of a spacer (15).

2. Linkers, Spacers and Tagged-Sugar Reference Standards 2.1 Linker and Spacer The synthesis of the cleavable linker and the structure of the spacer are shown in FIG. 3 and described below.

12: N-Fmoc-4-aminooxymethyl-benzoic acid

To a solution of 4-aminooxymethyl-benzoic acid, hydrochloride 11[1] (2.0 g, 0.010 mol) in dioxane (20 mL) and half saturated $Na_2CO_3$ solution (20 mL) was added Fmoc-Cl (2.8 g, 0.011 mol) and the mixture was stirred for 2 h. Ethyl acetate (100 mL) was added and the pH of the aqueous phase was adjusted to 1-3 by careful addition of $HCl_{(conc.)}$. The mixture was poured in to a separating funnel and the organic phase was isolated, washed once with water (100 mL), dried over $Na_2SO_4$ and the solvent was removed on a rotavap to give an oil that solidified upon standing. The crude product was purified by flash column chromatography (petroleum ether, ethyl acetate, AcOH 60:40:1). Yield: 3.5 g (92%) $^1$H-NMR (250 MHz, DMSO-d6) δ=4.05 (1H, t, J=6.3 Hz), 4.27 (2H, d, J=6.3 Hz), 4.51 (2H, s), 7.08-7.22 (6H, m), 7.46 (2H, d, J=7.4 Hz), 7.66 (2H, d, J=7.1 Hz), 7.72 (2H, d, J=8.4 Hz), 10.29 (1H, br. s), 12.78 (1H, br. s). $^{13}$C-NMR (63 MHz, DMSO-d6) δ=47.04, 66.03, 76.91, 120.51, 125.41, 127.45, 128.03, 128.89, 129.33, 129.63, 130.82, 141.19, 144.01, 157.12, 167.48. MS (ES) m/z=389 (MH$^+$).

[1] The material was prepared as previously described: Deles, J. et al.; PJCHDQ; Pol. J. Chem.; EN; 53; 1979; 1025-1032

13: Reaction of N-Fmoc-4-aminooxymethyl-benzoic acid (12) with t-butyl bromoacetate N-Fmoc-4-aminooxymethyl-benzoic acid (12) (1.0 g, 2.57 mmol) was dissolved in DMF (15 mL) and $Cs_2CO_3$ (0.42 g, 1.28 mmol, Aldrich) was added followed by stirring for 5 min at rt. tert-Butyl bromoacetate (0.55 g, 2.28 mmol, Fluka) was added and the mixture was heated to 50° C. for 30 min and then cooled to rt again. $CH_2Cl_2$ (70 mL) was added and the mixture as poured in to a separating funnel and washed with half saturated $NaHCO_3$ solution (3×50 mL) and then water (2×50 mL), dried over $MgSO_4$. The solvent was removed under reduced pressure to give the crude product as an oil. After flash column chromatography (20-40% ethyl acetate in petroleum ether) a white solid was obtained in a yield of 1.15 g (89%). $^1$H-NMR (250 MHz, CDCl$_3$) δ=1.37 (9H, s), 4.06 (1H, t, J=6.7 Hz), 4.37 (2H, d, J=6.7 Hz), 4.61 (2H, s), 4.67 (2H, S), 7.11-7.18 (2H, m), 7.22-7.27 (4H, m), 7.43 (2H, d, J=7.5 Hz), 7.60 (2H, d, J=7.3 Hz), 7.75 (1H, s), 7.93 (2H, dd, J=1.7 Hz, 6.6 Hz). $^{13}$C-NMR (63 MHz, CDCl$_3$) δ=26.31, 45.28, 59.95, 65.52, 75.99, 80.84, 118.30, 123.27, 125.41, 126.10, 126.93, 127.23, 128.30, 139.29, 139.58, 141.73, 155.70, 163.94, 165.15. MS (ES) m/z=542 (MK$^+$).

14: Preparation of Linker

The white solid 13 (1.15 g) obtained in the previous experiment was stirred in a 50% solution of $CF_3CO_2H$ in $CH_2Cl_2$ (30 mL) for 3 h and evaporated to dryness. The oily residue was taken up in a small amount of ethyl acetate and the product was precipitated as a fine white powder by slow addition of hexanes to the solution. The product was filtered and washed a couple of times with hexanes and dried under vacuum to give the desired product in an almost quantitative yield (1.0 g, 98%). $^1$H-NMR (250 MHz, DMSO-d6) δ=4.07 (1H, t, J=6, 3 Hz), 4.28 (2H, d, J=6, 3 Hz), 4.53 (2H, s), 4.62 (2H, S), 7.07-7.14 (2H, m), 7.17-7.26 (4H, m), 7.46 (2H, d, J=7.4 Hz), 7.66 (2H, d, J=7.2 Hz), 7.77 (2H, d, J=8.3 Hz), 10.30 (1H, br. s). $^{13}$C-NMR (63 MHz, DMSO-d6) δ=47.04, 61.62, 66.04, 76.79, 120.50, 125.41, 127.46, 128.03, 129.05, 129.69, 141.19, 142.20, 144.00, 157.12, 165.50, 169.47. MS (ES) m/z=446 (M-H$^+$). HRMS (ES) calculated ($C_{25}H_{21}NO_7Na^+$): 470.1210 found: 470.1224.

2.2 Synthesis of Tetramethylrhodamine (TMR)-Tagged Monosaccharide Standards of the General Structure G.

Figure 4:
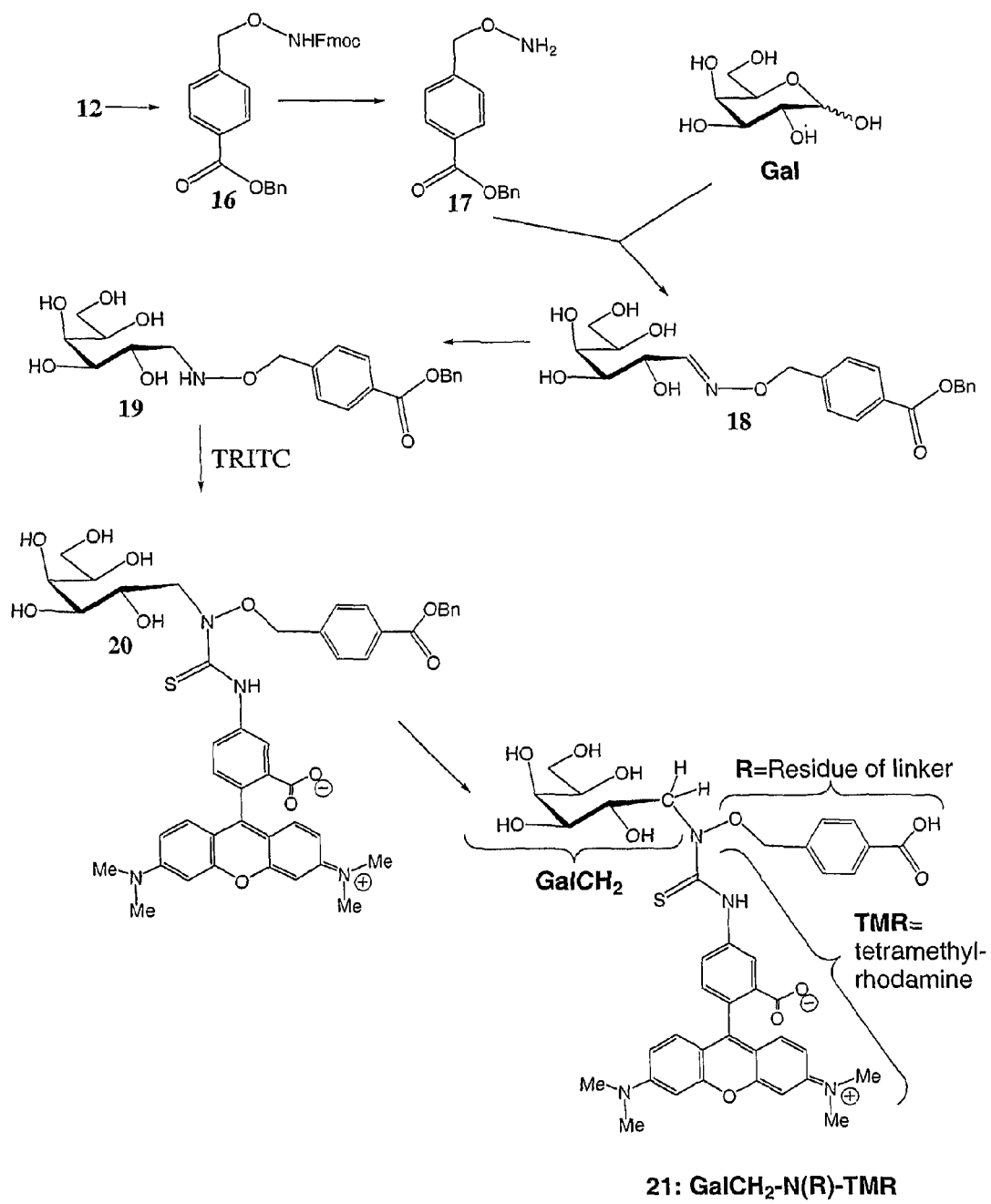
FIG. 4. Solution-phase synthesis of the TMR-tagged D-galactose derivative, $GalCH_2$—$N(R)$-TMR (21), and description of nomenclature used for monosaccharide standards.

The 8 monosaccharides D-Glc, D-Gal, D-Man, D-Xyl, D-GlcNAc, D-GalNAc, L-Fuc and D-GlcA were used. The general synthetic scheme is shown in FIG. 4 for D-Gal (2), and the structure of the product 21 is shown in FIG. 4 and is abbreviated GalCH$_2$—N(R)-TMR as shown. The structures of all eight SugarCH$_2$—N(R)-TMR monosaccharide derivatives prepared are shown in FIG. 5.

16: Reaction of N-Fmoc-4-aminooxymethyl-benzoic acid (12) with Benzylbromide

N-Fmoc-4-aminooxymethyl-benzoic acid (12, 2.0 g, 5.14 mmol) was dissolved in DMF (30 mL) and $Cs_2CO_3$ (0.84 g, 2.57 mmol) was added followed by stirring for 5 min at rt. Benzyl bromide (1.05 g, 6.17 mmol) was added and the mixture was allowed to stir for another 30 min at rt. Water (200 mL) was added and the mixture was extracted with $CH_2Cl_2$ (2×100 mL). The combined organic phases were washed with water (3×50 mL), dried over $MgSO_4$, evaporated to dryness to yield an oil which was used without further characterization in the next experiment.

17: Removal of Fmoc-Group from benzyl-(N-Fmoc-4-aminooxymethyl)-benzoate

The crude product (16) obtained in the previous experiment was stirred with 20% piperidine in DMF (20 mL) for 1 min and passed through a bed of silica gel to remove the majority of DMF and piperidine by suction. The product was eluted from the bed of silica gel with a mixture of ethyl acetate and pet. ether (1:1) and concentrated on a rotavap. Further purification was achieved by flash column chromatography (ethyl acetate, petroleum ether 1:1) to give a clear oil in a yield of 1.16 g (88%, two steps). $^1$H-NMR (250 MHz, CDCl$_3$) δ=4.66 (2H, s), 5.29 (2H, s), 7.25-7.39 (7H, m), 7.99 (2H, dd, J=1.7 Hz, 6.5 Hz). $^{13}$C-NMR (63 MHz, CDCl$_3$) δ=67.11, 77.59, 128.32, 128.57, 128.66, 129.02, 129.19, 130.32, 136.48, 143.47, 166.64. MS (MALDI-TOF) m/z=258 (MH$^+$).

General procedure for preparation of TMR labelled monosaccharide standards exemplified by the preparation of galactose standard.

18: Oxime Formation Between Galactose and benzyl-(4-aminooxymethyl)-benzoate

Galactose (90 mg, 0.50 mmol) was dissolved in a mixture of DMSO and AcOH (7:3, 3 mL) and (17, 128 mg, 0.50 mmol) was added. The mixture was heated for 3 h at 55° C. and poured into water (30 mL) and cooled on an ice bath which caused the product to crystallize as fine white crystals. The product was isolated by filtration, washed with water (2×10 mL) and dried under vacuum to yield the 170 mg (83%) of product as a single isomer. $^1$H-NMR (250 MHz, DMSO-d6) δ=3.38-3.55 (4H, m), 3.67-3.75 (1H, m), 4.27-4.33 (1H, m), 5.12 (2H, s), 5.37 (2H, s), 7.36-7.52 (7H, m), 7.56 (1H, d, J=7.6 Hz), 8.00 (2H, d, J=8.1 Hz). $^{13}$C-NMR (63 MHz, DMSO-d6) δ=63.40, 66.52, 68.37, 69.21, 70.04, 72.63, 74.27, 128.25, 128.33, 128.49, 128.91, 129.13, 129.67, 136.52, 144.22, 154.00, 165.78. MS (MALDI-TOF) m/z=442 (MNa$^+$)

19: Reduction of "galactose-oxime" (18) with $BH_3$-pyridine

The oxime (18,150 mg, 0.36 mmol) obtained in the previous experiment was dissolved in methanol (10 mL). $BH_3$-pyridine (225 μL, 8 M solution in pyridine, 1.80 mmol, Fluka) and $CCl_3CO_2H$ (0.50 mL, 50% aqueous solution) were added and the mixture was stirred for 1 h at rt. The reaction mixture was carefully poured into a half-saturated solution of $Na_2CO_3$ (20 mL) and extracted with a 1:1 mixture of ether and hexanes (2×10 ml) to remove excess borane reagent. The pH was now adjusted to 2-3 by careful addition of $HCl_{(conc.)}$ and the volume was reduced to half of the original on a ratovap. During the evaporation the product separated out as nice white crystalline solid, which was filtered of, washed with water (2×10 mL), ether (2×10 mL) and finally the product was dried under vacuum to give 112 mg (75%) of pure product. $^1$H-NMR (250 MHz, DMSO-d6) δ=3.31-3.33 (2H, m), 3.40-3.55 (5H, m), 3.74 (1H, t, J=6.3 Hz), 5.24 (2H, s), 5.37 (2H, s), 7.36-7.50 (5H, m), 7.60 (2H, d, J=8.2 Hz), 8.04 (2H, d, J=8.2 Hz). $^{13}$C-NMR (63 MHz, DMSO-d6) δ=53.34, 63.40, 64.73, 66.68, 69.37, 70.19, 70.89, 74.20, 128.36, 128.53, 128.92, 129.47, 129.87, 130.27, 136.41, 139.73, 165.62. MS (MALDI-TOF) m/z=422 (MH$^+$).

20: Labelling of Reduced Product (19) Using TRITC

A small amount of the product (19, 4.2 mg, 10 μmol) prepared in previous experiment was dissolved in DMF (1 mL) and TRITC (4.4 mg, 10 μmol) was added. After stirring for 1 h water (10 mL) was added and the precipitated product was redissolved by addition of $HCl_{(conc.)}$ and the clear red solution was applied to a small C-18 Sep-Pak column to bind the product. The column was flushed several times with water (total volume 30 mL) followed by release of the product with methanol (5 mL). The volume was reduced to approximately 0.5 mL and the material was purified by flash column chromatography on silica gel with a mixture of $CH_2Cl_2$, methanol, water, AcOH (70:20:9:1). The identity of the compound was confirmed by MS and used directly in the next experiment. MS (MALDI-TOF) m/z=865 (MH$^+$).

21: Hydrolysis of Ester Protecting Group to Give Final Standard

All the material (20) obtained in the previous experiment was dissolved in 1 M LiOH (1 mL) and stirred for 30 min followed by addition of water (10 mL) and acidification with $HCl_{(conc.)}$ to give a clear red solution. The product was desalted on a small C-18 Sep-Pak column by repeated washings with water (total volume 30 mL) followed by release of the product with methanol (5 mL). The volume was reduced to approximately 0.5 mL and the product was purified by flash column chromatography on silica gel with a mixture of chloroform, methanol, water (120:85:20). The identity of the compound was confirmed by high resolution MS and its purity was analysed using CE. HRMS (ES) calculated ($C_{39}H_{43}N_4O_{11}S$): 775.2649 found: 775.2700

Standards of the remaining monosaccharides (glucose, mannose, N-acetylglucosamine, N-acetylgalactosamine, xylose, fucose and glucuronic acid) were prepared using the same protocol as described for galactose in similar yields and purity. The compounds' identities were likewise confirmed by high resolution mass spectroscopy (see table below). Each compound gave a single peak in CE, and all 8 compounds (21-28) could be resolved in CE (FIG. 10).

| I. Standard | II. Calculated mass | III. Found mass | Variation |
|---|---|---|---|
| Galactose (21) | 775.2649 ($C_{39}H_{43}N_4O_{11}S$) | 775.2700 | Δ = 6.58 ppm |
| Glucose (22) | 775.2649 ($C_{39}H_{43}N_4O_{11}S$) | 775.2696 | Δ = 6.06 ppm |
| Mannose (23) | 775.2649 ($C_{39}H_{43}N_4O_{11}S$) | 775.2695 | Δ = 5.93 ppm |
| Xylose (24) | 745.2543 ($C_{38}H_{41}N_4O_{10}S$) | 745.2536 | Δ = 0.94 ppm |
| Fucose (25) | 759.2700 ($C_{39}H_{43}N_4O_{10}S$) | 759.2728 | Δ = 3.69 ppm |
| N-Acetylglucosamine (26) | 816.2914 ($C_{41}H_{46}N_5O_{11}S$) | 816.2983 | Δ = 8.45 ppm |
| N-Acetylgalactosamine (27) | 816.2914 ($C_{41}H_{46}N_5O_{11}S$) | 816.2995 | Δ = 9.92 ppm |
| Glucuronic acid (28) | 789.2441 ($C_{39}H_{41}N_4O_{12}S$) | 789.2507 | Δ = 8.36 ppm |

3. Examples of B

Preparation and Nomenclature of Solid Supports

Figure 6:
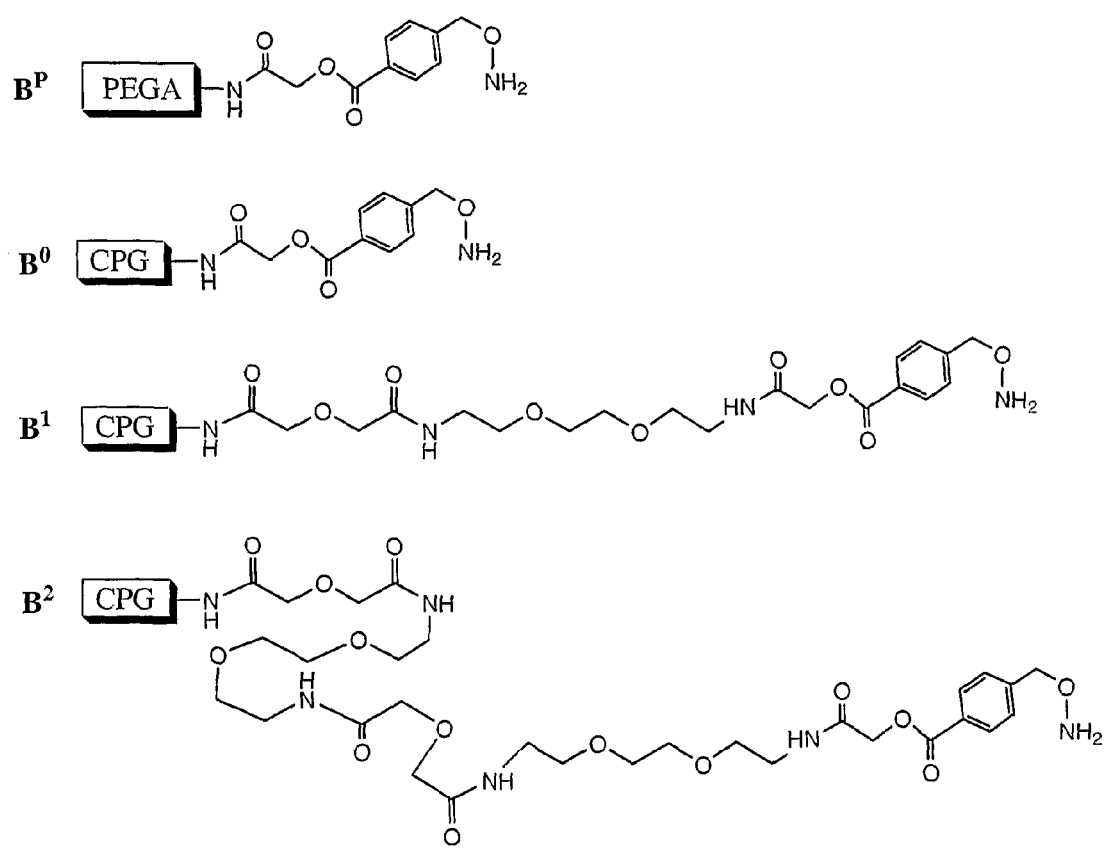
FIG. 6. Structures of the four solid supports $B^P$, $B^0$, $B^1$ and $B^2$.

Solid supports of general structure B (FIG. 1) were prepared using both PEGA resin (PEGA 1900, Versamatrix A/S) and controlled-pore glass (CPG). $B^P$ indicates a PEGA resin where the linker is attached directly to the amino groups on the commercial resin without a spacer. $B^0$, $B^1$ and $B^2$ indicate CPG where the linker has been attached through 0, 1 and 2 spacers respectively to aminopropylated glass (AMP-CPG, CPG-Biotech). The structures of the four solid supports are shown in FIG. 6.

3.1 $B^P$ (PEGA Resin of General Structure B)

1 g of commercial PEGA 1900 resin (loading of amino groups: 0.23 mmol/g) swelled in methanol was washed repeated time with DMF to ensure complete removal of the methanol. The linker (14) (308 mg, 0.69 mmol), TBTU (207 mg, 644 mmol) and DIPEA (119 mg, 0.92 mmol) were mixed in DMF (10 mL) and left to pre-activate for 5 min before adding the mixture to the resin. After 3 h the reagents were removed by suction and the resin was washed with $CH_2Cl_2$ (5×20 mL).

A small portion of the resin was taken out for Kaiser test which confirmed a successful coupling of the linker to the resin. Likewise, the loading of linker on the resin was determined as described in example 3.3 and found to be approximately 0.20 mmol/g by comparison with a standard curve. The hydroxylamine protecting group (Fmoc) was now removed from the remaining resin by treatment with 20% piperidine in DMF (15 mL for 2 min and 15 mL for 18 min) followed by extensive washings with DMF (5×20 mL) and $CH_2Cl_2$ (7×20 mL). The resin was dried under high vacuum for 24 h to give the final PEGA resin ($B^P$) which was used for all subsequent experiments.

3.2 $B^0$, $B^1$ and $B^2$ (Controlled Pore Glass, CPG)

$B^0$: Coupling of Linker 14 with CPG-$NH_2$

AMP CPG (250 mg, loading=50.1 μmol/g, 0.0125 mmol. Millipore, product no. AMP1400B) was washed with DMF (3×2 mL), 50% DIPEA in DMF (3×2 mL), and DMF (3×2 mL). The beads were treated with a mixture of 14 (17 mg, 0.038 mmol), TBTU (12 mg, 0.037 mmol), and DIPEA (8.6 μL, 0.05 mmol) in DMF at rt over night. The beads were washed with DMF (3×2 mL), $CH_2Cl_2$ (3×2 mL), and treated with 50% of $Ac_2O$ in pyridine for 15 min at rt, washed with $CH_2Cl_2$ (3×2 mL), DMF (3×2 mL), $CH_2Cl_2$ (3×2 mL), and dried. The loading was determent to 14.2 μmol/g as described for $B^1$. The Fmoc group was removed using 20% piperidine in DMF for 2×10 min at rt and washed with, DMF (3×2 mL), CH$_2$Cl$_2$ (3×2 mL), and ethanol (3×2 mL), and CH$_2$Cl$_2$ (3×2 mL). The resin was dried in vacuum.

B$^1$: Coupling of One Spacer 15 and Linker 14 with CPG-NH$_2$

AMP CPG (2.26 g, loading=50.1 µmol/g, 0.11 mmol. Millipore, product no. AMP1400B) was washed with DMF (3×2 mL), 50% DIPEA in DMF (3×2 mL), and DMF (3×2 mL). The beads were treated with a mixture of 15 (168 mg, 0.34 mmol), TBTU (105 mg, 0.33 mmol), and DIPEA (78 µL, 0.45 mmol) in DMF for 3 h at rt. The resin was washed with DMF (3×5 mL), CH$_2$Cl$_2$ (3×5 mL), and treated with 50% Ac$_2$O in pyridine for 15 min at rt. The beads were washed with CH$_2$Cl$_2$ (3×5 mL), DMF (3×5 mL), CH$_2$Cl$_2$ (3×5 mL), and treated with 50% TFA in CH$_2$Cl$_2$ for 2 h at rt. Washed with CH$_2$Cl$_2$ (3×5 mL), DMF (3×5 mL), and CH$_2$Cl$_2$ (3×5 mL). ⅓ of the beads (2.5 mL, ~0.70 g, ~35 µmol) were washed with DMF (3×5 mL). Treated with 14 (47 mg, 0.11 mmol), TBTU (33 mg, 0.10 mmol), and DIPEA (34 µL, 0.20 mmol) in DMF over night at rt. The beads were washed with DMF (3×5 mL), CH$_2$Cl$_2$ (3×5 mL), and treated with 50% Ac$_2$O in pyridine for 15 min at rt, washed with CH$_2$Cl$_2$ (3×5 mL), DMF (3×5 mL), CH$_2$Cl$_2$ (3×5 mL), and dried. The loading was determined (29 µmol/g) and the beads were treated with 20% piperidine in DMF at rt for 2×10 min. The beads were washed with, DMF (3×2 mL), CH$_2$Cl$_2$ (3×2 mL), and ethanol (3×2 mL), CH$_2$Cl$_2$ (3×2 mL), and dried.

B$^2$: Coupling of Two Spacers 15 and Linker 14 with CPG-NH$_2$

⅔ of the resin with one spacer from B$^1$ (5.5 mL, ~1.54 g, ~77 µmol) was washed with DMF (3×5 mL). The beads were treated with a mixture of 15 (114 mg, 0.23 mmol), TBTU (72 mg, 0.22 mmol), and DIPEA (53 µL, 0.31 mmol) in DMF over night at rt. The beads were washed with DMF (3×5 mL), CH$_2$Cl$_2$ (3×5 mL), and treated with 50% Ac$_2$O in pyridine for 15 min at rt, washed with CH$_2$Cl$_2$ (3×5 mL), DMF (3×5 mL), CH$_2$Cl$_2$ (3×5 mL), and treated with 50% CF$_3$CO$_2$H in CH$_2$Cl$_2$ for 2 h at rt, washed with CH$_2$Cl$_2$ (3×5 mL), DMF (3×5 mL), and CH$_2$Cl$_2$ (3×5 mL). Half the amount of the beads (~42 µmol) were washed with DMF (3×5 mL) and treated with 14 (56 mg, 0.13 mmol), TBTU (39 mg, 0.12 mmol), and DIPEA (29 µL, 0.17 mmol) at rt over night. The beads were washed with DMF (3×5 mL), CH$_2$Cl$_2$ (3×5 mL) and treated with 50% Ac$_2$O in pyridine for 15 min at rt, washed with CH$_2$Cl$_2$ (3×5 mL), DMF (3×5 mL), CH$_2$Cl$_2$ (3×5 mL) and dried. The loading was determent as described for B$^1$ to 36 µmol/g. The resin was covered with 20% piperidine in DMF at rt for 2×10 min, washed with, DMF (3×5 mL), CH$_2$Cl$_2$ (3×5 mL), ethanol (3×5 mL) 3×CH$_2$Cl$_2$ (3×5 mL), and dried in vacuum.

3.3 Example of the Estimation of the Loading of Capture Groups on Solid Supports of General Structure B (FIG. 1)

Seven concentrations of Fmoc-Gly-OH in 20% piperidine in DMF (0.0 mM, 0.1 mM, 0.25 mM, 0.5 mM, 1.0 mM, 1.5 mM, 2.0 mM) were prepared. The UV absorbance of released fulvene were measured at 290 nm using nonodrop technology (Saveen Werner Nanodrop, Model: ND-1000, Serial No: 0911). The absorbance was plotted against the concentration giving a linear curve with slope 0.581 mM$^{-1}$.

Fmoc protected B$^1$ beads (4.8 mg) were treated with 20% piperidine in DMF (200 µL) for 10 min. The UV absorbance at 290 nm was measured to 0.410 and the liberated fulvene concentration was calculated $$[\text{fulvene}] = \frac{\text{abs}_{obs}}{\text{slope}_{std\ curve}}$$

$$[\text{fulvene}] = \frac{0.410}{0.581\ \text{mM}^{-1}} = 0.706\ \text{mM}$$

The loading was then calculated by using $$\text{loading} = \frac{[\text{fulvene}] \times V_{solvent}}{m_{beads}}$$

$$\text{Loading of } B^1: \text{loading} = \frac{0.706\ \text{mmol/L} \times 200\ \mu L}{4.8\ \text{mg}} = 29.4\ \mu\text{mol/g}$$

4. Examples of A+B→C, and Processing of C 4.1 Variation of Capture Conditions Using Glucose as the Reducing Sugar and B$^2$ as the Solid Support.

Various solvents, temperatures and additives were examined in order to find preferable conditions for the capture of reducing sugars on solid supports of general structure B$_1$ to produce C. D-Glc was used as the model compound, as the amount of uncaptured Glc in solution could be readily estimated with high sensitivity using the Amplex Red assay from Molecular Probes. The amount of Glc captured was thus calculated to be the amount added minus the amount remaining in solution after incubation.

15-20 mg of beads (B$^2$) were treated with a solution of glucose under different conditions. After end reaction time the supernatant was removed and the amount of unreacted glucose was estimated using the Amplex Red Glucose/Glucose Oxidase Assay Kit (A-22189, Molecular Probes).

Capture of glucose using different solvents, concentrations, temperatures and reaction times

| No | Glc | Vol | [Glc] | Solvent | pH | Temp | Time | Capture |
|---|---|---|---|---|---|---|---|---|
| C$^2$A$_1$ | 1 eq | 108 µL | 4.0 mM | Citrate* | 5 | 37° C. | 4 h | 8% |
| C$^2$A$_2$ | 1 eq | 108 µL | 4.0 mM | DMSO/AcOH | 3 | 37° C. | 4 h | 2% |
| C$^2$A$_3$ | 1 eq | 108 µL | 4.0 mM | Citrate | 5 | 37° C. | on | 16% |
| C$^2$A$_4$ | 1 eq | 108 µL | 4.0 mM | DMSO/AcOH | 3 | 37° C. | on | 21% |
| C$^2$A$_5$ | 1 eq | 108 µL | 4.0 mM | Citrate | 5 | 55° C. | 4 h | 13% |
| C$^2$A$_6$ | 1 eq | 108 µL | 4.0 mM | DMSO/AcOH | 3 | 55° C. | 4 h | 16% |
| C$^2$A$_7$ | 1 eq | 108 µL | 4.0 mM | Citrate | 5 | 55° C. | on | 35% |
| C$^2$A$_8$ | 1 eq | 108 µL | 4.0 mM | DMSO/AcOH | 3 | 55° C. | on | 35% |
| C$^2$A$_9$ | 0.1 eq | 104 µL | 0.4 mM | Citrate | 5 | 55° C. | on | 85% |
| C$^2$A$_{10}$ | 0.1 eq | 104 µL | 0.4 mM | DMSO/AcOH | 3 | 55° C. | on | 94% |

*0.1 M citrate/phosphate buffer, pH 5.0.

4.2 Capture, Processing and Analysis of Representative Reducing Sugars on $B^P$.

The following designations are used below to describe compounds of the general structures C, $C_{red}$, D, E, F, G, H, I and J (FIG. 1). The particular letter describing the particular structure under discussion is given first, e.g. C or E. The next superscript number refers to which of the four solid supports shown in FIG. 6 was used. Thus, by way of example if $B^P$ (FIG. 6) is used to capture a sugar, then the product will have the general structure C which is further designated as $C^P$. The next number refers to which of the ten samples of reducing sugars shown in FIG. 2 was captured. Thus, $C^P2$ refers to the product of the PEGA resin $B^P$ that has captured galactose (compound 2 of FIG. 2). In the same way, $D^25$ would refer to the product obtained when the solid support $B^2$ has captured the tetrasaccharide LNT (5, FIG. 2) to give $C^25$, and then been further capped to $D^25$.

4.2.1 Capture and Processing of Reducing Sugar 3

$C^P3$: Capture of LacNAc (3) on $B^P$

A stock solution was made by first dissolving LacNAc (3) (38 mg, 0.10 mmol) in water (1.0 mL) and then diluting the sample 10 times with a mixture of DMSO and AcOH (7:3, 9 mL) to give a 10 mM stock solution of LacNAc (3). 40 µL (0.40 µmol) was then taken from the stock solution and diluted further with the mixture of DMSO and AcOH (7:3, 150 µL) and the whole was added to $B^P$ (10 mg, 2 µmol) and left to incubate at 60° C. over night. The resin was washed several times: DMF (5×0.5 mL), methanol (5×0.5 mL) and used directly in the next experiments.

$D^P3$: Capping of $C^P3$ with Acetic Anhydride

All the resin obtained in experiment $C^P3$ was treated with a mixture of $Ac_2O$ and methanol 1:1 (0.4 mL) for 1 h followed by washing with DMF (5×0.5 mL), water (2×0.5 mL), methanol (5×0.5 mL) and used directly in the next experiment.

$E^P3$: Reduction of $D^P3$ with $BH_3$-pyridine

The resin obtained in experiment $D^P3$ was covered with methanol (0.1 mL) and $BH_3$-pyridine (20 µL, 8 M in pyridine) was added followed by addition of 50% $CCl_3CO_2H$ acid in water (40 µL). The reaction was left to proceed for 2 h at rt followed by washing with DMF (5×0.5 mL), methanol (5×0.5 mL) and $CH_2Cl_2$ (5×0.5 mL). The resin was used directly in the next step.

$F^P3$: Tagging of $E^P3$ Using TRITC

TRITC (0.89 mg, 2 µmol) was dissolved in DMF (0.2 mL) and the solution was added to the resin ($E^P3$) and left for 2 h at rt followed by extensive washing DMF (5×0.5 mL), $CH_2Cl_2$ (5×0.5 mL), methanol (5×0.5 mL), and finally water (5×0.5 mL) to remove excess dye. The resin was used directly in the next step.

$G^P3$: Cleavage of TMR Tagged LacNAc from Support

Figure 11:
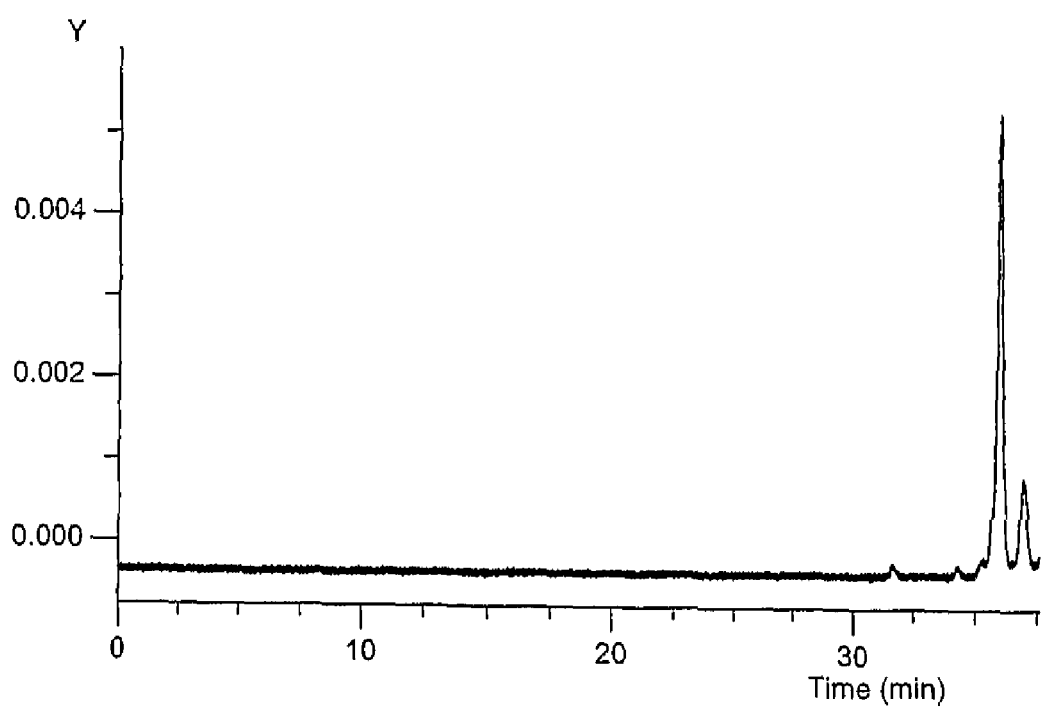
FIG. 11. CE of $G^P3$ (with LacNAc as the reducing sugar tagged using TRITC, section 4.2.1).

The resin obtained in the previous experiment $F^P3$ was covered with a 1 M solution of LiOH (0.2 mL) and left for 2 h. The liquid was collected from the beads by suction followed by washing of the beads with water (3×0.5 mL). The collected liquid and washings were pooled and pH was adjusted to neutral with 10% AcOH. The dark red solution was adsorbed on a Sep-Pak column (50 mg), washed with water (2 mL) and eluted with methanol (0.5 mL). The identity of the product was confirmed by MS (ES) m/z=978 ($MH^+$) and the profile was recorded by CE (FIG. 11).

4.2.2 Capture and Processing of Reducing Sugar 5

$C^P5$: Capture of Lacto-N-tetraose (5) on $B^P$

A solution was made by dissolving 5 (5.0 mg, 7.1 µmol) in a mixture of DMSO and AcOH 7:3 (3 mL). This mixture was added to PEGA resin $B^P$ (175 mg, 35 µmol) and incubated at 60° C. over night. The resin was washed several times: DMF (5×5 mL), methanol (5×5 mL) and used directly in the next experiments.

$D^P5$: Capping of $C^P5$ with Acetic Anhydride

All the resin obtained in experiment $C^P5$ was treated with a mixture of $Ac_2O$ and methanol 1:1 (5 mL) for 1 h followed be washing with DMF (5×5 mL), water (2×5 mL), methanol (5×5 mL) and used directly in the next experiment.

$E^P5$: Reduction of $D^P5$ with $BH_3$-pyridine

The resin obtained in experiment $D^P5$ was swelled in methanol (2 mL) and $BH_3$-pyridine (200 µL, 8 M in pyridine) was added followed by addition of 50% $CCl_3CO_2H$ acid in water (400 µL). The reaction was left to proceed for 2 h at rt followed by washing with DMF (5×5 mL), methanol (5×5 mL) and $CH_2Cl_2$ (5×5 mL). Finally the resin was dried down under vacuum over night and stored at room temperature for further use.

$F^P5$: Tagging of $E^P5$ with Bromine Containing MS-Tag

A small amount of the dried resin $E^P5$ (10 mg, 0.4 µmol) was washed with $CH_2Cl_2$ (3×0.5 mL) in order to swell the resin. A solution was made by dissolving 4-bromophenyl isothiocyanate (0.85 mg, 4 µmol) in DMF (0.2 mL) and the mixture was added to the resin and left to react for 2 h at rt followed by washing of the resin DMF (5×0.5 mL), $CH_2Cl_2$ (5×0.5 mL), methanol (5×0.5 mL), and finally water (5×0.5 mL). The resin was used directly in the next step.

$G^P5$: Cleavage of Bromine Tagged Lacto-N-tetraose from Support

Figure 12:
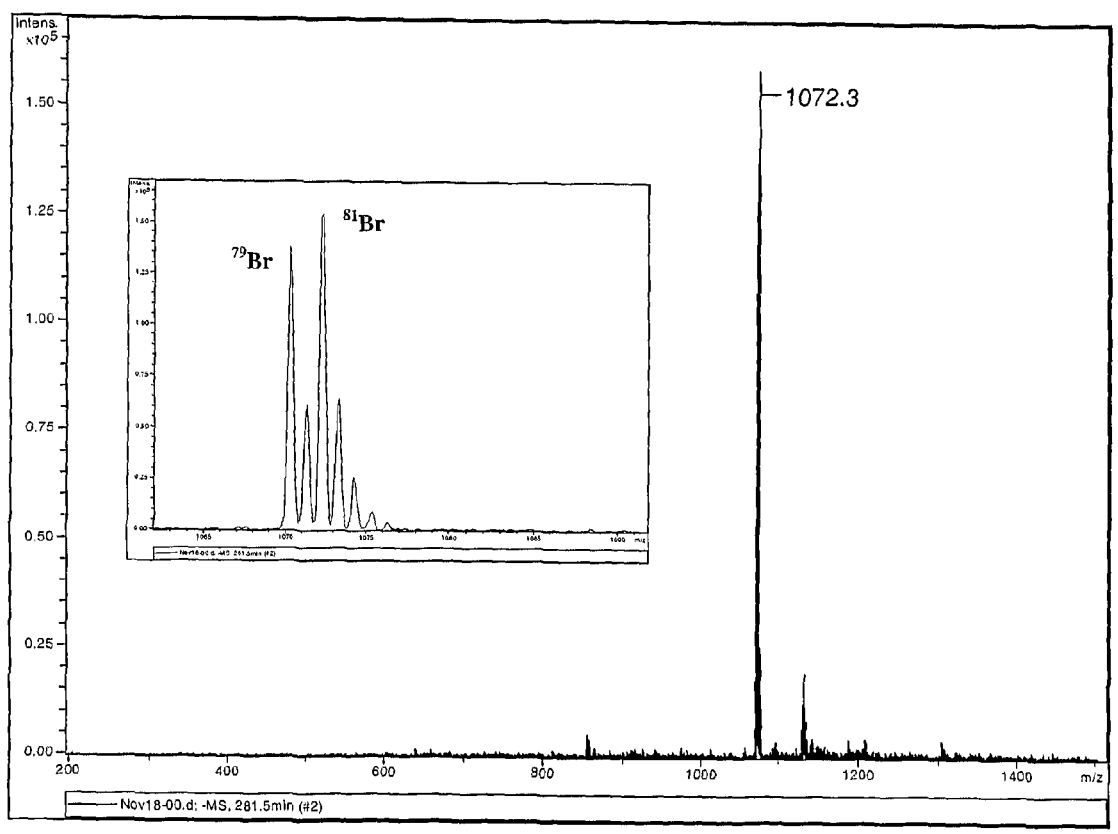
FIG. 12. Electrospray mass-spectrum in the negative ion mode of $G^P5$ (with lacto-N-tetraose as the reducing sugar tagged using 4-bromophenylisothiocyanate, section 4.2.2). The inset is an expansion showing the two peaks corresponding to the major isotopes of Br.

The resin obtained in the previous experiment $F^P5$ was covered with a 1 M solution of LiOH (0.2 mL) and left for 2 h. The liquid was collected from the beads by suction followed by washing of the beads with water (3×0.5 mL). The collected liquid and washings were pooled and pH was adjusted to slightly acidic (pH 3-4) with 10% AcOH. The solution containing the desired product was adsorbed on a Sep-Pak column (50 mg), washed with water (2 mL) and eluted with methanol (0.5 mL). The identity of the product was confirmed by MS (ES) m/z=1072 (98%, $MH^+$), 1074 (100%, $MH^+$), m/z=1070 (98%, $M-H^+$), 1072 (100%, $M-H^+$). FIG. 12 shows the mass-spectrum with an inset expansion where the two isotopes of bromine can clearly be distinguished.

4.2.3 Capture and Processing of Reducing Sugar Mixture 6

$C^P6$: Capture of Monosaccharide Mixture 6 (Fuc:Man:GalNac, 2:3:1) on $B^P$

A series of 3 stock solutions were made by dissolving the 3 individual monosaccharides (Fuc: 16 mg, 0.10 mmol, Man: 18 mg, 0.10 mol, GalNAc: 22 mg, 0.10 mmol) in water (3×1.0 mL) and then diluting the samples 10 times with a mixture of DMSO and AcOH (7:3, 3×9 mL) to give 10 mM stock solutions of the 3 monosaccharides. A mixture was now prepared by taking the following amounts from the 3 stock solutions: Fuc (20 µL, 0.2 µmol), Man (30 µL, 0.3 µmol) and GalNAc (10 µL, 0.1 µmol). This monosaccharide solution was diluted further by addition of the mixture of DMSO and AcOH (7:3, 150 µL) and the whole was added to PEGA resin $B^P$ (10 mg, 2 µmol) and left to incubate at 60° C. over night. The resin was washed several times: DMF (5×0.5 mL), methanol (5×0.5 mL) and used directly in the next experiments.

$D^P6$: Capping of $C^P6$ with Acetic Anhydride

All the resin obtained in experiment $C^P6$ was treated with a 1:1 mixture of $Ac_2O$ and methanol (0.4 mL) for 1 h followed be washing with DMF (5×0.5 mL), water (2×0.5 mL), methanol (5×0.5 mL) and used directly in the next experiment.

$E^P6$: Reduction of $D^P6$ with $BH_3$-pyridine

The resin obtained in experiment $D^P6$ was covered with methanol (0.1 mL) and $BH_3$-pyridine (20 μL, 8 M in pyridine) was added followed by addition of 50% $CCl_3CO_2H$ in water (40 μL). The reaction was left to proceed for 2 h at rt followed by washing with DMF (5×0.5 mL), methanol (5×0.5 mL) and $CH_2Cl_2$ (5×0.5 mL). The resin was split into 2 separate containers ($E^P6_a$ and $E^P6_b$, app. 5 mg each) and used directly in the next steps.

$F^P6_a$: Tagging of $E^P6_a$ Using TRITC

TRITC (0.5 mg, 1.2 μmol) was dissolved in DMF (0.2 mL) and the solution was added to the resin ($E^P6_a$) and left for 2 h at rt followed by extensive washing DMF (5×0.5 mL), $CH_2Cl_2$ (5×0.5 mL), methanol (5×0.5 mL) and finally water (5×0.5 mL) to remove excess dye. The resin was used directly in the next step.

$G^P6_a$: Cleavage of TMR Tagged Monosaccharide Mixture from Support

The resin obtained in the previous experiment ($F^P6_a$) was covered with a 1 M solution of LiOH (0.1 mL) and left for 2 h. The liquid was collected from the beads by suction followed by washing of the beads with water (3×0.5 mL). The collected liquid and washings were pooled and pH was adjusted to neutral with 10% AcOH. The dark red solution was adsorbed on a Sep-Pak column (50 mg), washed with water (2 mL) and eluted with methanol (0.5 mL). The identity of the 3 tagged products was confirmed by MS (ES) m/z=759 (Fuc, $MH^+$), 775 (Man, $MH^+$) 816 (GalNAc, $MH^+$) and their profile was recorded by CE (FIG. 13).

$F^P6_b$: Tagging of $E^P6_b$ with Acetic Anhydride

A 1:1 mixture of $Ac_2O$ and methanol (0.2 mL) was added to the resin ($E^P6_b$) and left for 16 h at rt followed by extensive washing DMF (5×0.5 mL), $CH_2Cl_2$ (5×0.5 mL), methanol (5×0.5 mL) and finally water (5×0.5 mL). The resin was used directly in the next step.

$G^P6_b$: Cleavage of Acetic Acid Tagged Monosaccharide Mixture from Support

The resin obtained in the previous experiment ($F^P6_b$) was covered with a 10% solution of $NH_4OH$ (0.1 mL) and left for 2 h. The liquid was collected from the beads by suction followed by washing of the beads with water (3×0.5 mL). The collected liquid and washings were pooled and evaporate to dryness on a rotavap, re-dissolved in water (1 mL) and freeze dried. The identity of the 3 tagged products was confirmed by MS (ES) m/z=356 (Fuc, $M-H^+$), 372 (Man, $M-H^+$), 413 (GalNAc, $M-H^+$). The ratio of the intensities of the 3 signals was approximately 1.3:2:1.

4.2.4 Capture and Processing of Reducing Sugar Mixture 7

$C^P7$: Capture of Monosaccharide Mixture 7 (Fuc:Man:GalNac, 1:3:2) on $B^P$

The same 3 stock solutions of monosaccharides (10 mM each) that were used in experiment $C^P6$ was used in the following experiment. A mixture was prepared by taking the following amounts from the 3 stock solutions: Fuc (10 μL, 0.1 μmol), Man (30 μL, 0.3 μmol) and GalNAc (20 μL, 0.2 μmol). This monosaccharide solution was diluted further by addition of the mixture of DMSO and AcOH (7:3, 150 μL) and the whole was added to PEGA resin $B^P$ (10 mg, 2 μmol) and left to incubate at 60° C. over night. The resin was washed several times: DMF (5×0.5 mL), methanol (5×0.5 mL) and used directly in the next experiments.

$D^P7$: Capping of $C^P7$ with Acetic Anhydride

All the resin obtained in experiment $C^P7$ was treated with a 1:1 mixture of $Ac_2O$ and methanol (0.4 mL) for 1 h followed by washing with DMF (5×0.5 mL), water (2×0.5 mL), methanol (5×0.5 mL) and used directly in the next experiment.

$E^P7$: Reduction of $D^P7$ with $BH_3$-pyridine

The resin obtained in experiment $D^P7$ was covered with methanol (0.1 mL) and $BH_3$-pyridine (20 μL, 8 M in pyridine) was added followed by addition of 50% $CCl_3CO_2H$ in water (40 μL). The reaction was left to proceed for 2 h at rt followed by washing with DMF (5×0.5 mL), methanol (5×0.5 mL) and $CH_2Cl_2$ (5×0.5 mL). The resin was split into 2 separate containers ($E^P7_a$ and $E^P7_b$, app. 5 mg each) and used directly in the next step.

$F^P7_a$: Tagging of $E^P7_a$ Using TRITC

TRITC (0.5 mg, 1.2 μmol) was dissolved in DMF (0.2 mL) and the solution was added to the resin ($E^P7_a$) and left for 2 h at rt followed by extensive washing DMF (5×0.5 mL), $CH_2Cl_2$ (5×0.5 mL), methanol (5×0.5 mL) and finally water (5×0.5 mL) to remove excess dye. The resin was used directly in the next step.

$G^P7_a$: Cleavage of TMR Tagged Monosaccharide Mixture from Support

The resin obtained in the previous experiment ($F^P7_a$) was covered with a 1 M solution of LiOH (0.1 mL) and left for 2 h. The liquid was collected from the beads by suction followed by washing of the beads with water (3×0.5 mL). The collected liquid and washings were pooled and pH was adjusted to neutral with 10% AcOH. The dark red solution was adsorbed on a Sep-Pak column (50 mg), washed with water (2 mL) and eluted with methanol (0.5 mL). The identity of the 3 tagged products was confirmed by MS (ES) m/z=759 (Fuc, $MH^+$), 775 (Man, $MH^+$) 816 (GalNAc, $MH^+$) and their profile was recorded by CE (FIG. 14).

$F^P7_b$: Tagging of $E^P7_b$ with Deuteroacetic Anhydride

A 1:1 mixture of deuteroacetic anhydride and methanol (0.2 mL) was added to the resin ($E^P7_b$) and left for 16 h at rt followed by extensive washing DMF (5×0.5 mL), $CH_2Cl_2$ (5×0.5 mL), methanol (5×0.5 mL) and finally water (5×0.5 mL). The resin was used directly in the next step.

$G^P7_b$: Cleavage of Deuterium Tagged Monosaccharide Mixture from Support

The resin obtained in the previous experiment ($F^P7_b$) was covered with a 10% solution of $NH_4OH$ (0.1 mL) and left for 2 h. The liquid was collected from the beads by suction followed by washing of the beads with water (3×0.5 mL). The collected liquid and washings were pooled and evaporate to dryness on a rotavap, re-dissolved in water (1 mL) and freeze dried. The identity of the 3 deuterium tagged products was confirmed by MS (ES) m/z=359 (Fuc, $M-H^+$), 375 (Man, $M-H^+$), 416 (GalNAc, $M-H^+$). The ratio of the intensities of the 3 signals was approximately 1:4:4.

4.2.5 Capture and Processing of Reducing Oligosaccharide Mixture 9

$C^P9$: Capture of Oligosaccharide Mixture 9 (G2-G7) on $B^P$

A solution was made by dissolving an equimolar amount (10 μmol each) of the pure oligosaccharides G2-G7 in water (1 mL). 100 μL of the oligosaccharide containing solution was added to a mixture of DMSO and AcOH (7:3, 0.9 mL) and the whole was added to PEGA resin B$^P$ (60 mg, 12 µmol) and left to incubate at 50° C. over night. The resin was washed several times: DMF (5×2 mL), methanol (5×2 mL) and used directly in the next experiments.

D$^P$9: Capping of C$^P$9 with Acetic Anhydride

All the resin obtained in experiment C$^P$9 was treated with a 1:1 mixture of Ac$_2$O and methanol (2 mL) for 1 h followed be washing with DMF (5×2 mL), water (2×2 mL), methanol (5×2 mL) and used directly in the next experiment.

E$^P$9: Reduction of D$^P$9 with BH$_3$-pyridine

The resin obtained in experiment D$^P$9 was covered with methanol (1 mL) and BH$_3$-pyridine (150 µL, 8 M in pyridine) was added followed by addition of 50% CCl$_3$CO$_2$H in water (300 µL). The reaction was left to proceed for 2 h at rt followed by washing with DMF (5×2 mL), methanol (5×2 mL) and CH$_2$Cl$_2$ (5×2 mL). The resin was used directly in the next step.

F$^P$9: Tagging of E$^P$9 Using FITC

FITC (12 mg, 30 µmol) was dissolved in a 1:1 mixture of DMF and methanol (1 mL) and the solution was added to the resin (E$^P$9) and left for 2 h at rt followed by extensive washing DMF (5×2 mL), CH$_2$Cl$_2$ (5×2 mL), methanol (5×2 mL) and finally water (5×2 mL) to remove excess dye. The resin was used directly in the next step.

G$^P$9: Cleavage of Oligosaccharide Mixture Tagged Using FITC from Support

Figure 15:
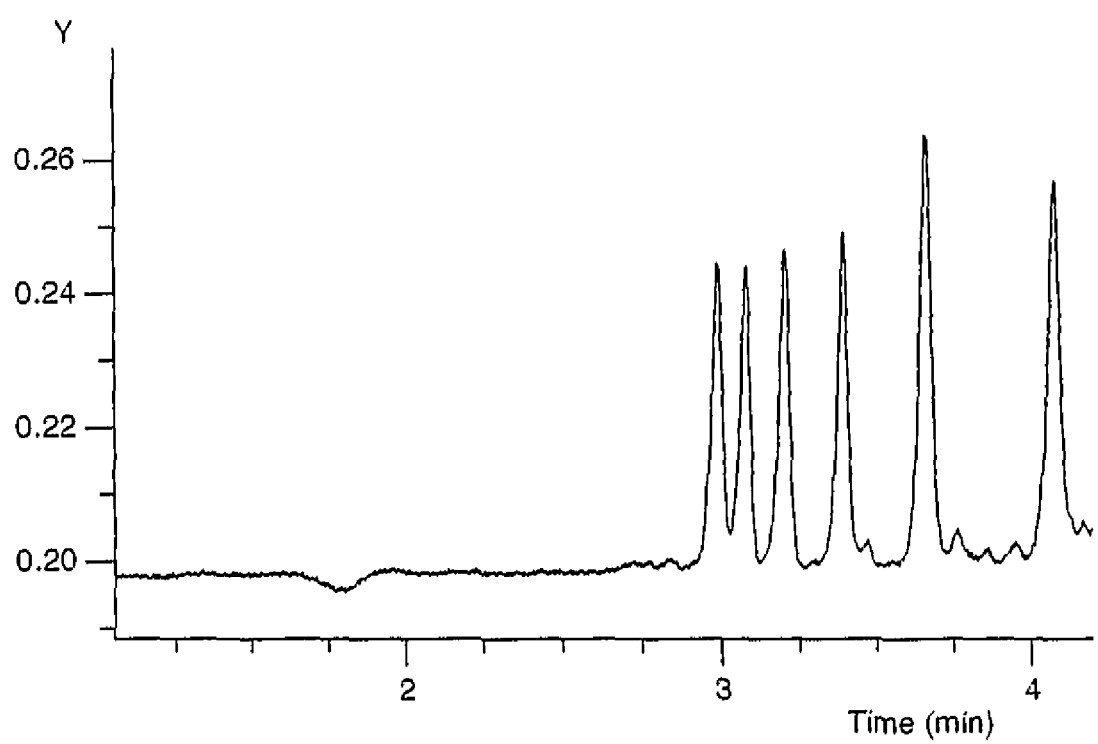
FIG. 15. CE of $G^P9$ (with the oligosaccharide mixture 9 tagged using FITC, section 4.2.5). The order of elution is G7 to G2 (FIG. 2).

The resin obtained in the previous experiment (F$^P$9) was covered with a 1 M solution of LiOH (1 mL) and left for 2 h. The liquid was collected from the beads by suction followed by washing of the beads with water (3×3 mL). The collected liquid and washings were pooled and pH was adjusted to neutral with 10% AcOH. The strong yellow solution was adsorbed on a Sep-Pak column (350 mg), washed with water (10 mL) and eluted with methanol (3 mL). The presence of all 6 tagged oligosaccharides was confirmed by MS (ES) m/z=881 (G2, MH$^+$), 1043 (G3, MH$^+$), 1205 (G4, MH$^+$), 1367 (G5, MH$^+$), 1529 (G6, MH$^+$), 1691 (G7, MH$^+$) and the profile of the mixture was recorded by CE (FIG. 15).

4.2.6 Capture and Processing of Oligosaccharides Released from Ribonuclease B.

C$^P$10: Capture and Processing of Oligosaccharides from Rnase B (10) on B$^P$

Crude oligosaccharides from PNGase F digestion of RNAse B (Sigma, R-7884) were used after protein removal on a Centricon-10 concentrator (Millipore) followed by carbohydrate purification on a Carbograph SPE column (150 mg bed weight; Scantec Lab). A solution was made by dissolving crude oligosaccharides from RNAse B (10)$^2$ (300 µg, app. 0.2 µmol) in a mixture of DMSO containing 0.9 M citric acid and THF 2:1 (100 µL). This mixture was added to PEGA resin B$^P$ (5 mg, 1.0 µmol) and incubated at 60° C. over night. The resin was washed several times: DMF (5×0.3 mL), methanol (5×0.3 mL) and used directly in the next experiments.

D$^P$10: Capping of C$^P$10 with Acetic Anhydride

All the resin obtained in experiment C$^P$10 was treated with a 1:1 mixture of Ac$_2$O and methanol (0.2 mL) for 1 h followed be washing with DMF (5×0.3 mL), water (2×0.3 mL), methanol (5×0.3 mL) and used directly in the next experiment.

E$^P$10: Reduction of D$^P$10 with BH$_3$-pyridine

The resin obtained in experiment D$^P$10 was covered with methanol (0.2 mL) and BH$_3$-pyridine (10 µL, 8 M in pyridine) was added followed by addition of 50% CCl$_3$CO$_2$H in water (20 µL). The reaction was left to proceed for 2 h at rt followed by washing with DMF (5×0.3 mL), methanol (5×0.3 mL) and CH$_2$Cl$_2$ (5×0.3 mL). The resin was used directly in the next step.

F$^P$10: Tagging of E$^P$10 Using FITC

FITC (1.9 mg, 5 µmol) was dissolved in a mixture of DMF and methanol (1:1, 0.2 mL) and the solution was added to the resin (E$^P$10) and left for 2 h at 600 followed by extensive washing DMF (5×0.3 mL), CH$_2$Cl$_2$ (5×0.3 mL), methanol (5×0.3 mL) and finally water (5×0.3 mL) to remove excess dye. The resin was used directly in the next step.

G$^P$10: Cleavage of Oligosaccharides from RNAse Tagged Using FITC from Support

Figure 16:
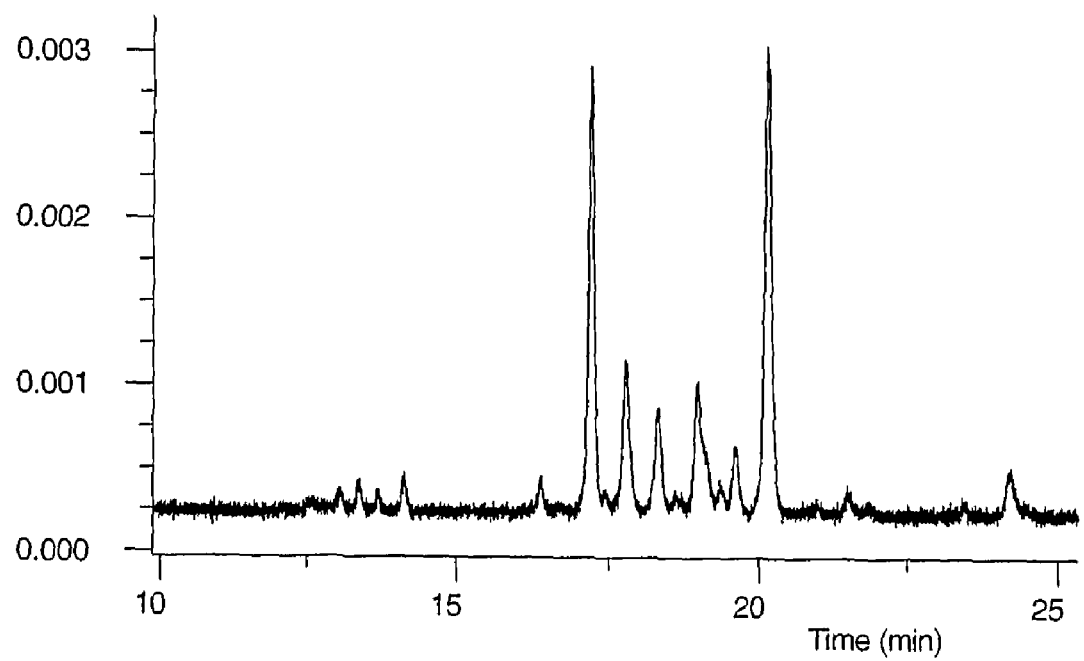
FIG. 16. CE of $G^P10$ (ribonuclease B oligosaccharides 10 tagged using FITC, section 4.2.6).

The resin obtained in the previous experiment (F$^P$10) was covered with a 1 M solution of LiOH (0.2 mL) and left for 2 h. The liquid was collected from the beads by suction followed by washing of the beads with water (3×0.5 mL). The collected liquid and washings were pooled and pH was adjusted to neutral with 10% AcOH. The yellow solution containing the desired product was adsorbed on a Sep-Pak column (50 mg), washed with water (2 mL) and eluted with methanol (0.5 mL). The profile of the labelled oligosaccharides was analysed by CE. The CE (FIG. 16) indicates the presence of several oligosaccharides and some unidentified contaminants. The identity of at least one of the known components was confirmed by MS (ES) m/z 1775 (Man$_5$GlcNAcGlcNAcCH$_2$—N—(R)-TAG, MH$^+$).

4.3 Capture and Processing of Representative Reducing Sugars on CPG Supports.

4.3.1 Capture and Processing of 2 on B$^1$

C$^1$2: Capture of galactose (2) on B$^1$

B$^1$ (20 mg, 0.6 µmol) was treated with 2 (6.6 µL, 1 mg/mL water, 0.03 µmol) in citrate-phosphate buffer (113 µL) and left over night at 55° C. The beads were transferred to a syringe and washed with water (3×0.5 mL) and ethanol (3×0.5 mL) giving C$^1$2.

D$^1$2: Capping of C$^1$2 with Acetic Anhydride

C$^1$2 (0.6 µmol) were capped with 50% Ac$_2$O in ethanol for 15 min at rt and washed with ethanol (3×0.5 mL) giving D$^1$2.

E$^1$2: Reduction of D$^1$2 with BH$_3$-pyridine

D$^1$2 (0.6 µmol) was treated with 100 µL of a solution of BH$_3$-pyridine (25 µL), 50% CCl$_3$CO$_2$H (50 µL) in ethanol (500 µL). The mixture was left for 2 h at rt. The beads were washed with ethanol (3×0.5 mL) giving E$^1$2.

F$^1$2: Labelling of E$^1$2 with TRITC

E$^1$2 (0.6 µmol) was treated with TRITC (100 µL of 1.0 mg in 300 µL NMP and 300 µL CH$_2$Cl$_2$) and left for 2 h at rt. The beads were washed with CH$_2$Cl$_2$ (3×0.5 mL), ethanol (3×0.5 mL), and water (3×0.5 mL) giving F$^1$2 (red beads).

G$^1$2: Base Treatment of F$^1$2

Figure 17:
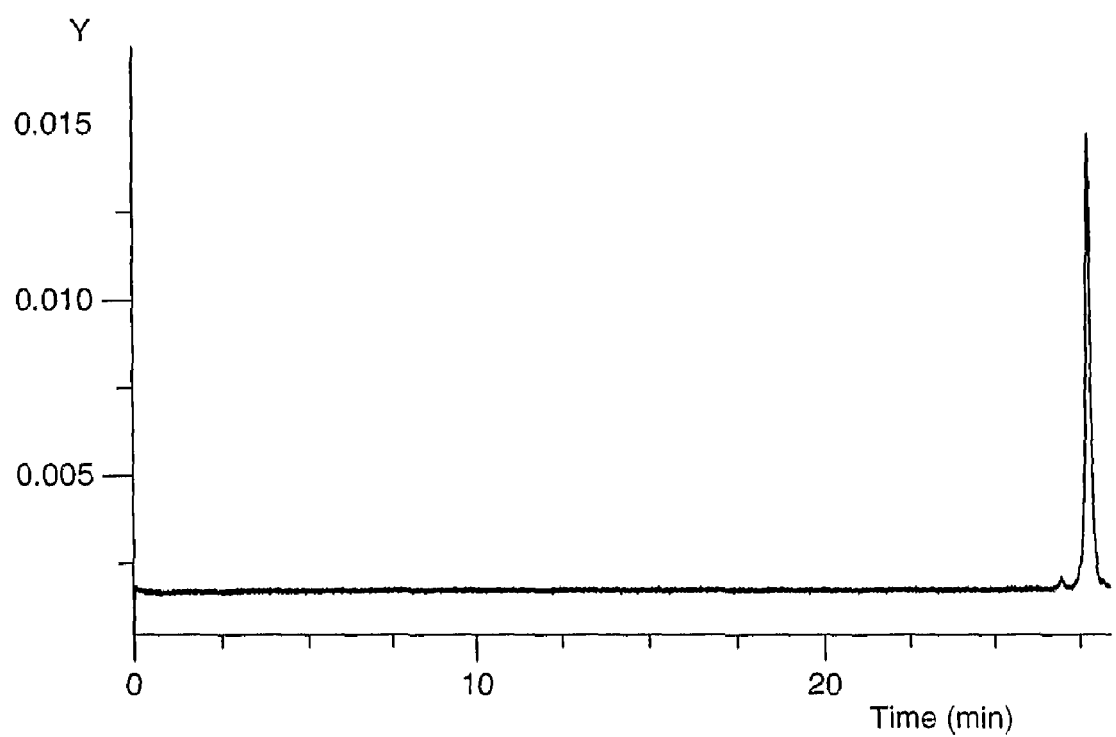
FIG. 17. CE of $G^12$ (with Gal 2 as the reducing sugar tagged using TRITC, section 4.3.1).

F$^1$2' (0.6 µmol) was treated with 1 M solution of LiOH (100 µL) for 1 h at rt and the red solution was isolated and neutralised with 50% AcOH in water giving G$^1$2 (red solution) which were passed through a Sep-Pak column (30% CH$_3$CN in water) and analysed by MS (775.3, MH$^+$) and CE (FIG. 17).

4.3.2 Capture and Processing of 5 on B$^1$

C$^1$5: Capture of LNT (5) on B$^1$

B$^1$ (20 mg, 0.6 µmol) was treated with 5 (25 µL, 2 mg/mL water, 0.03 µmol) in citrate-phosphate buffer (113 µL) and left over night at 55° C. The beads were transferred to a syringe and washed with water (3×0.5 mL) and ethanol (3×0.5 mL) giving $C^1 5$.

$D^1 5$: Capping of $C^1 5$ with Acetic Anhydride $C^1 5$ (0.6 µmol) was treated with 50% $Ac_2O$ in ethanol for 15 min at rt and washed with (3×0.5 mL) giving $D^1 5$.

$E^1 5$: Reduction of $D^1 5$ with $BH_3$-pyridine $D^1 5$ (0.6 µmol) was treated with 100 µL of a solution of $BH_3$-pyridine (25 µL), 50% $CCl_3CO_2H$ (50 µL) in ethanol (500 µL). The mixture was left for 2 h at rt. The beads were washed with ethanol (3×0.5 mL) giving $E^1 5$.

$F^1 5$: Labelling of $E^1 5$ with TRITC $E^1 5$ (0.6 µmol) was treated with TRITC (100 µL of 1.0 mg in 300 µL NMP and 300 µL $CH_2Cl_2$) and left for 2 h at rt. The beads were washed with $CH_2Cl_2$ (3×0.5 mL), ethanol (3×0.5 mL), and water (3×0.5 mL) giving $F^1 5$ (red beads).

$G^1 5$: Base Treatment of $F^1 5$

Figure 18:
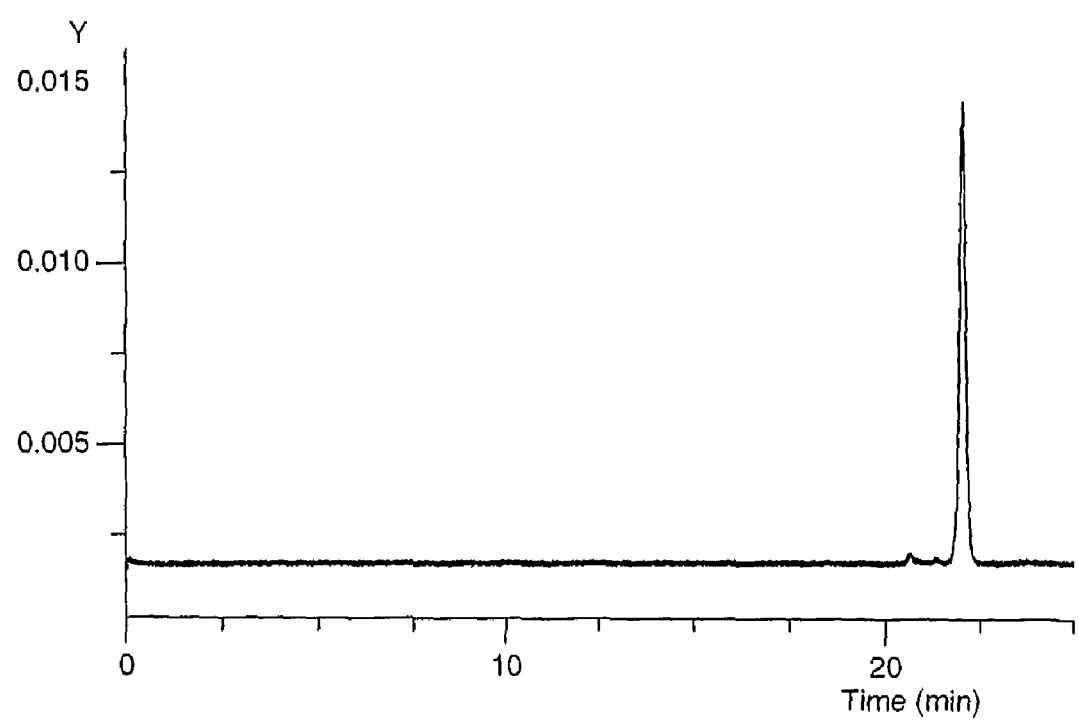
FIG. 18. CE of $G^15$ (with LNT 5 as the reducing sugar tagged using TRITC, section 4.3.2).

The resin was treated with a 1 M solution of LiOH (100 µL) for 1 h at rt and the red solution was isolated by filtration and the beads were washed with water (3×75 µL) and neutralised with 50% AcOH in water giving $G^1 5$ (red solution) which were passed through a Sep-Pak column (30% $CH_3CN$ in water) and analysed by MS (ES) m/z=1300.6 (M-H$^+$), 1302.4 (MH$^+$) and by CE (FIG. 18).

Alternatively, $E^1 5$ could be labelled with 1-fluoro-2,4-dinitrobenzene (Sanger's reagent, (FIG. 8) as follows. The resin was treated with Sanger's reagent (20 eq, 0.4 µL, Sigma) and TEA (10 eq, 0.2 µL) in ethanol (70 µL) for 2 h at 55° C. The beads were washed with ethanol (3×0.5 mL), $CH_2Cl_2$ (3×0.5 mL), ethanol (3×0.5 mL), and water (3×0.5 mL) (yellow beads), then treated with 1 M solution of LiOH (70 µL) for 1 h at rt (brown solution). The solution was collected by filtration and the beads were washed with water (3×50 µL). The mixture was neutralised with 50% AcOH (yellow solution). The mixture was passed through a Sep-Pak column with 30% $CH_3CN$ in water. MS (ES) m/z=1023.1 (M-H$^+$).

4.3.3 Capture and Processing of Mixture 8 on $B^1$ $C^1 8$: Capture of Galactose (2) and LNT (5) on $B^1$ $B^1$ (20 mg, 0.6 µmol) was treated with 2 (6.6 µL, 1 mg/mL water, 0.03 µmol), 5 (25 µL, 2 mg/mL water, 0.03 µmol), citrate-phosphate buffer (100 µL), and left over night at 55° C. The beads were washed with water (3×0.5 mL) and ethanol (3×0.5 mL) giving $C^1 8$.

$D^1 8$: Capping of $C^1 8$ with Acetic Anhydride

The remaining hydroxylamines in $C^1 8$ (0.6 µmol) were capped with 50% $Ac_2O$ in ethanol for 15 min at rt and washed with ethanol (3×0.5 mL) giving $D^1 8$.

$E^1 8$: Reduction of $D^1 8$ with $BH_3$-pyridine $D^1 8$ (0.6 µmol) was treated with 100 µL of a solution of $BH_3$-pyridine (Fluka, 25 µL), 50% $CCl_3CO_2H$ (50 µL) in ethanol (500 µL). The mixture was left for 2 h at rt. The beads were washed with ethanol (3×0.5 mL) giving $E^1 8$.

$F^1 8$: Labelling of $E^1 8$ Using TRITC $E^1 8$ (0.6 µmol) was treated with TRITC (100 µL of 1.0 mg in 300 µL NMP and 300 µL $CH_2Cl_2$) and left for 2 h at rt giving $F^1 8$. The beads were washed with $CH_2Cl_2$ (3×0.5 mL), ethanol (3×0.5 mL), and water (3×0.5 mL) (red beads).

Figure 19:
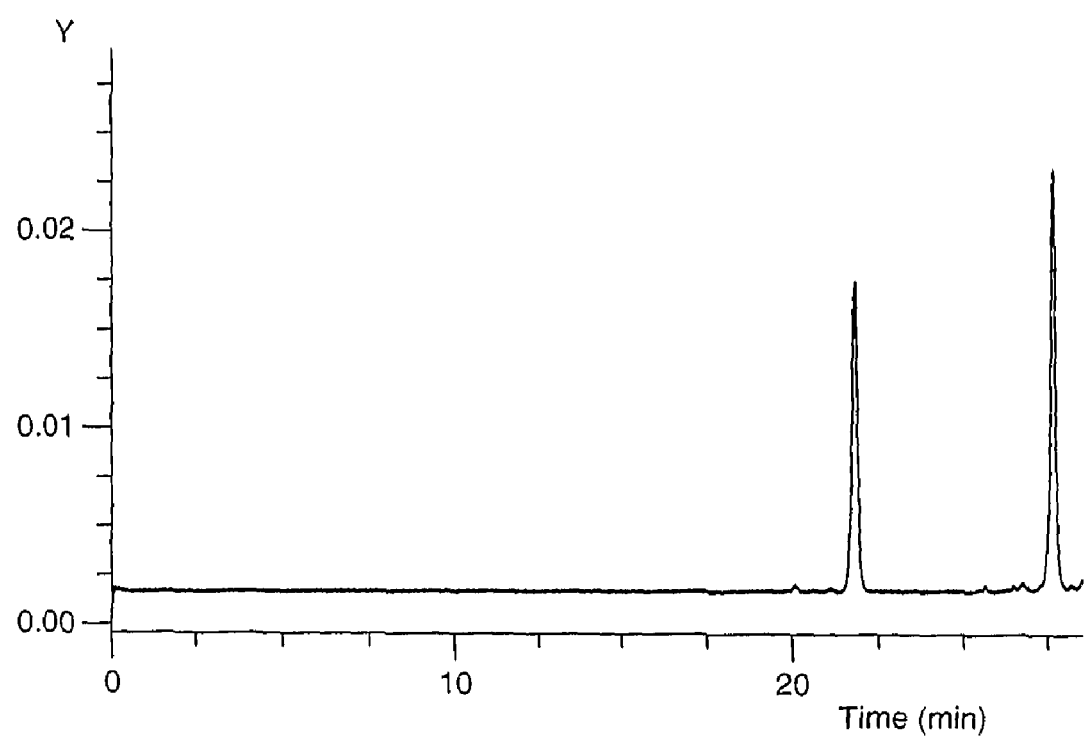
FIG. 19. CE of $G^18$ (with 8 as the reducing sugar mixture tagged using TRITC, section 4.3.3). The order of elution is LNT followed by Gal.

$G^1 8$: Base Treatment of $F^1 8$ $F^1 8$ was treated with 1 M solution of LiOH (100 µL) for 1 h at rt and the red solution was isolated and neutralised with 50% AcOH in water giving $G^1 8$ (red solution) which were passed through a Sep-Pak column (30% $CH_3CN$ in water) and analysed by CE (FIG. 19).

5. Reaction of Immobilized Oligosaccharides with Enzymes 5.1 Reaction of an Immobilized Tagged Oligosaccharide with a Glycosidase 5.1.1 Reaction of immobilized lacto-N-tetraose (LNT, 5) of structure F (cap=acetyl, TAG=TMR) with beta-galactosidase (bovine testes, SIGMA product G-4142, 1 U/mL) on CPG supports with none ($F^0 5$), one ($F^1 5$) and two ($F^2 5$) spacers. All 3 immobilized oligosaccharides were prepared essentially as described for $F^1 5$ (section 4.3.2).

The solid supports (5 mg) were incubated with beta-galactosidase (100 µL of 0.2 U/mL solution in 0.1 M citrate/phosphate buffer pH 5.0 containing 0.2% BSA for 23 h at 37° C., and the resin was then washed with 3× water, 3× ethanol, 3× $CH_2Cl_2$, 3× Et ethanol OH, and 3× water. The beads were treated with 1 M solution of LiOH (60 µL) for 1 h at rt giving products of the general structures $G)_5$, $G^1 5$, and $G^2 5$ in solution. Each red solution was collected by filtration. The filtrate was neutralised with 50% AcOH and analysed using CE.

Figure 20:
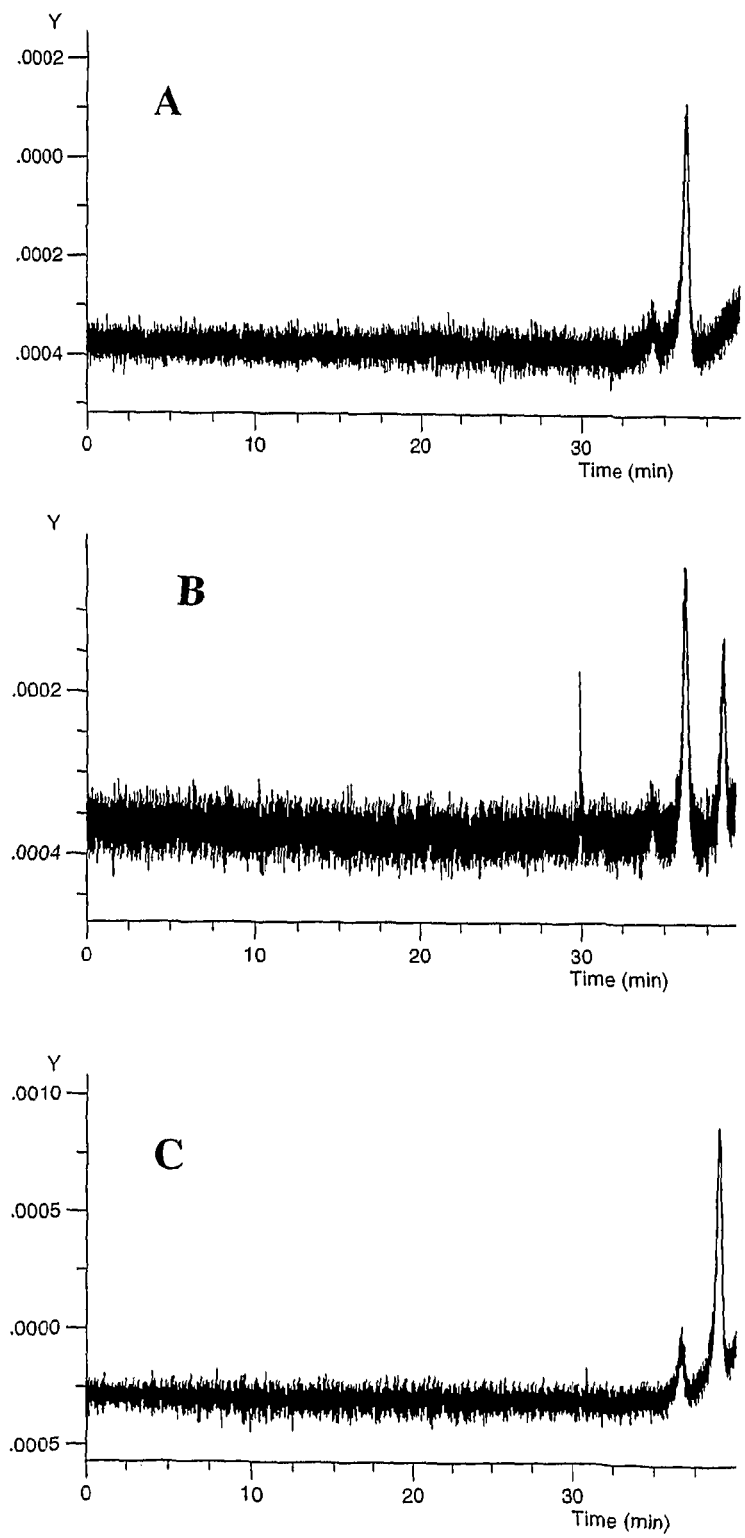
FIG. 20. CE of the cleaved products $G^05$ (A), $G^15$ (B) and $G^25$ (C) after beta-galactosidase digestion of immobilized LNT (5), section 5.1.1). The TRITC-labelled LNT tetrasaccharide elutes first near 36 minutes. Loss of galactose yields the trisaccharide product eluting after 38 minutes.

FIG. 20 shows that there was no detectable cleavage of galactose from LNT for $F^0 5$, 39% conversion for $F^1 5$ (i.e. 39% of the tetrasaccharide had lost the terminal Gal residue and been converted to the trisaccharide) and 83% conversion for $F^2 5$. The nature of the spacer was therefore found to be important to the course of the enzyme reaction.

Figure 21:
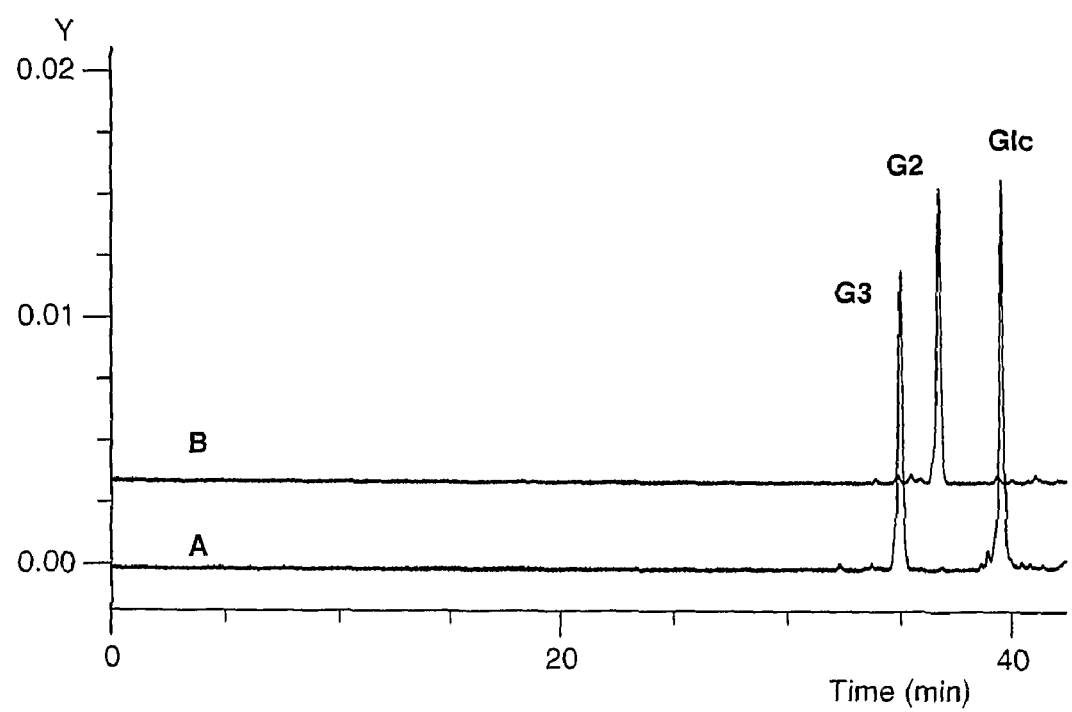
FIG. 21. CE of the cleaved product before (trace A) and after (trace B) incubation of $F^24$ (maltotriose (G3) as the reducing sugar tagged using TRITC) with glucoamylase, section 5.1.2). A reference sample of tagged Glc (22, FIG. 5) was added to the sample prior to recording trace A.

5.1.2 Reaction of immobilized maltotriose $F^2 4$ (cap=acetyl, TAG=TMR) with glucoamylase 2 from *Aspergillus niger* (kindly provided by Dr. Birte Svensson, Carlsberg Laboratories) on CPG support with two spacers. $F^2 4$ was prepared essentially as described for $F^1 5$ (section 4.3.2) but using maltotriose (G3, FIG. 2) as the reducing sugar and $B^2$ as the solid support. $F^2 4$ (ca 5 mg) was incubated for 23 h at 37° C. with 50 µL of 0.1 mg/mL of enzyme in 0.1 M sodium acetate buffer pH 5.5 containing 0.2% BSA. After washing and cleavage as described above, the product was analyzed by CE (FIG. 21), which showed complete conversion of immobilized labelled maltotriose to a new peak eluting between labelled maltotriose and glucose, therefore assigned as the maltobiose (G2) TMR adduct.

5.2 Reaction of an immobilized untagged oligosaccharide with a glycosidase and capture of the released reducing monosaccharide on the same support.

Figure 22:
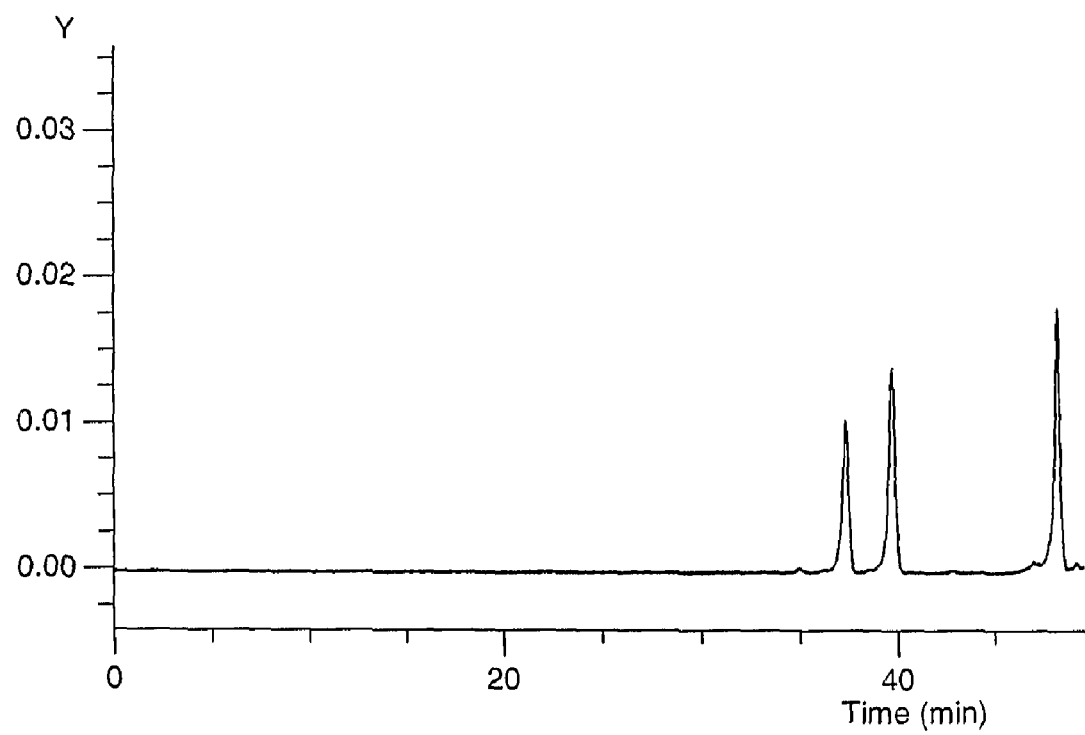
FIG. 22. CE of the cleaved products obtained after beta-galactosidase treatment of $C^25$ (bearing LNT and free $NH_2$ groups), followed by capture of the released galactose, reduction and tagging using TRITC, section 5.2. The order of elution is LNT, the trisaccharide resulting from loss of galactose and galactose (21).

Reaction of immobilized LNT of structure $C^2 5$ (non-reduced, non-capped, non-tagged) with beta-galactosidase (bovine testes) was carried out on CPG solid support with two spacers. $C^2 5$ was prepared essentially as described for $C^1 5$ (section 4.3.2). Prior to use, the enzyme solution was freed from small-molecule contaminants by repeated centrifugation using a Microcon YM-3 centrifugal filter device (Millipore). $C^2 5$ (5 mg) was incubated for 23 h at 37° C. with 55 µL of 0.9 U/mL of enzyme in 0.1 M citrate/phosphate, pH 5.0, containing 0.2% BSA, and then a further 20 h at 55° C. to permit capture of released galactose. The solid was washed, reduced, capped with acetic anhydride, tagged using TRITC and cleaved with LiOH as described above for the conversion of $C^1 5$ to $G^1 5$. The CE of cleaved product is shown in FIG. 22 which shows the presence of unreacted LNT (32%) and similar amounts of both the TMR-labelled product trisaccharide and cleaved galactose. This experiments confirms the capture of cleaved sugar on the same uncapped support from which it was cleaved.

6. Variation of Capping Agents

6.1. Capping of C to Produce D

Figure 23:
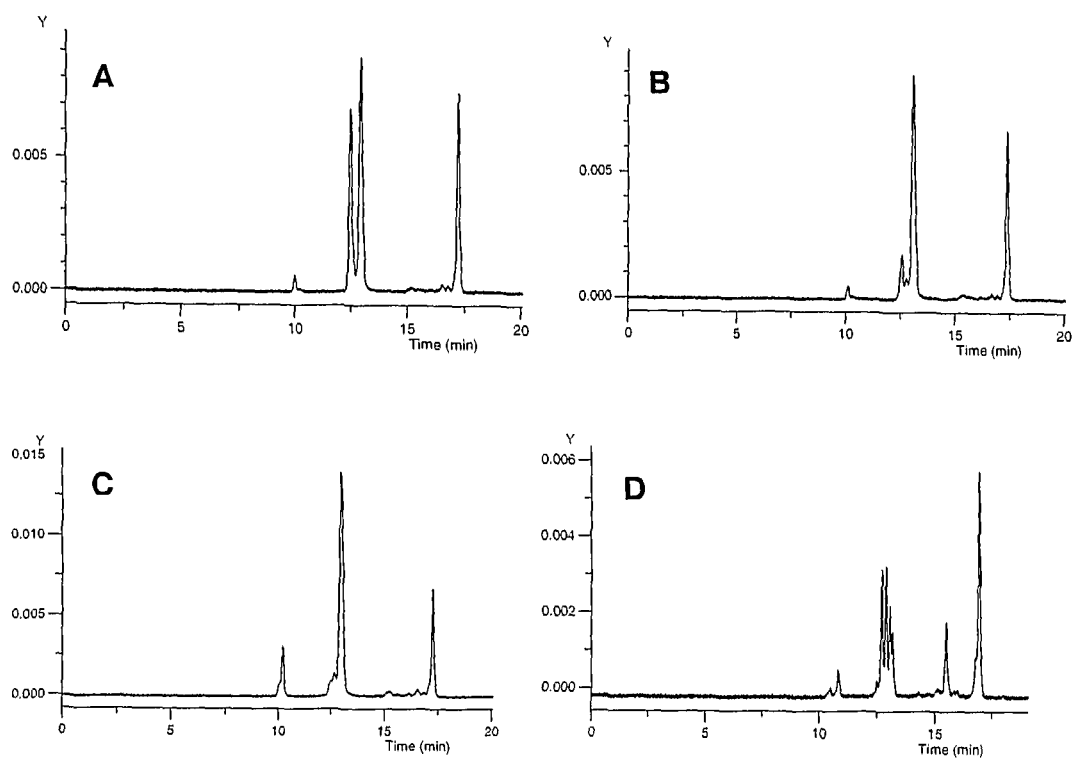
FIG. 23. CE analysis of the cleaved products derived from $C^22$ (immobilized galactose) after capping with various agents, reduction and labelling using TRITC, section 6.1). The capping agents were A (acetic anhydride), B (benzoic anhydride), C (trichloroacetic anhydride) and D (dibromoxylene). Tagged galactose (21) elutes near 17 minutes in all traces.

A selection of capping agents was used to effect the conversions C goes to D (FIG. 1). $C^22$ was used as the substrate (where the solid was CPG with 2 spacers and the captured sugar was galactose). The amino groups on C were then capped with, among others, acetic anhydride, benzoic anhydride, tricholoracetic anhydride and dibromoxylene (FIG. 6). The capping was carried with 50% solutions of the capping agent in ethanol, for 15-120 min at rt. The samples were then processed as described for the conversion of $C^12$ to $G^12$ (section 4.3.1), i.e., reduction, labelling using TRITC, base-cleavage and analysis by CE. The results are shown in FIG. 23 which shows that all conditions provided the target TMR-labelled galactose (compound 21, FIG. 5) with varying amounts of other impurities appearing before compound 21 in the electropherogram.

Figure 24:
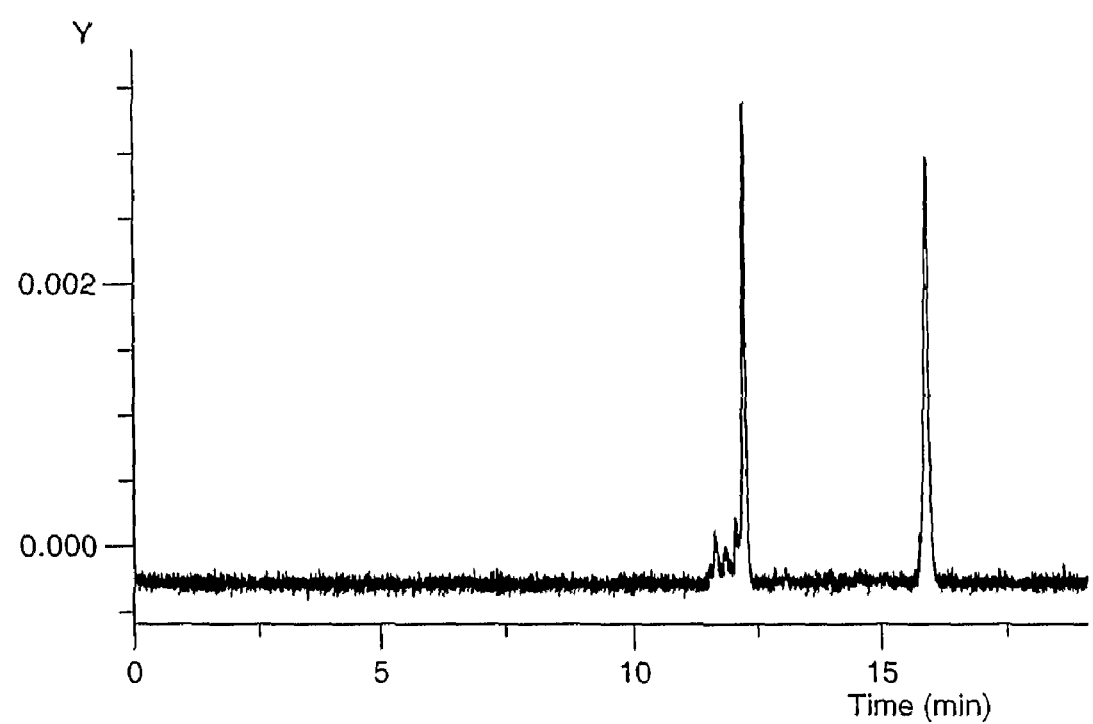
FIG. 24. CE of the cleaved product obtained from processing galactose through the sequence C→$C_{red}$→→G, section 6.2). The galactose 21 elutes at 17 minutes.

6.2 Example of Capping of $C_{red}$ to Produce E $C^22$ from section 6.1 above was reduced with $BH_3$-pyridine as described for the conversion of $D^12$ to $E^12$ above (section 4.3.1). The product $C_{red}^22$ differs from $E^12$ in that it contains uncapped $NH_2$ groups. $C_{red}^22$ (5 mg) was reacted with benzoic acid NHS-ester (0.4 mg, 1.75 μmol) and TEA (1.0 μL) in DMF (50 μL) over night at 60° C. The product of the reaction having the general structure $E^22$ (with the cap being a benzoate) was then washed and processed as usual, by tagging using TRITC, cleavage and analysis by CE. FIG. 24 shows the product to be substantially the same as that formed by the sequence C goes to D goes to E and on to G. The identity of the product was confirmed by its MS (ES) m/z=775.0 ($MH^+$).

7. Example of the Use of a Tether

E Goes to H Goes to I Goes to J (FIG. 1)

Synthesis of 29 as Example of X-Tether-$Y_p$

29: 4-Isothiocyanato-benzyl)-carbamic acid 9H-fluoren-9-ylmethyl ester

To a solution of 4-aminobenzylamine (0.93 mL, 8.20 mmol) in anhydrous $CH_2Cl_2$ (20 mL) was added TEA (1.15 mL, 8.27 mmol) followed by a solution of Fmoc-N-hydroxysuccinimide ester (2.48 g, 7.35 mmol) in dry $CH_2Cl_2$ (10 mL). After 30 min of stirring, $CH_2Cl_2$ (100 mL) was added and the mixture was washed successively with sat. aq. $NaHCO_3$ (2×50 mL) and brine (50 mL), and dried ($Na_2SO_4$). The solvent was removed under reduced pressure and the residue purified by dry column vacuum chromatography (0-60% EtOAc in n-heptane) to yield the Fmoc-protected material (4-Amino-benzyl)-carbamic acid 9H-fluoren-9-ylmethyl ester (2.30 g, 91%). $^1$H-NMR (250 MHz, DMSO-d6) δ=4.03 (2H, d, J=5, 3 Hz), 4.22 (1H, t, J=6, 8 Hz), 4.33 (2H, d, J=6, 8 Hz), 4.95 (2H, s), 6.53 (2H, d, J=8.3 Hz), 6.92 (2H, d, J=8.2 Hz), 7.29-7.44 (4H, m), 7.64-7.72 (3H, m), 7.88 (2H, d, J=7.3 Hz). $^{13}$C-NMR (63 MHz, DMSO-d6) δ43.97, 47.19, 65.65, 114.09, 120.46, 121.75, 125.58, 127.11, 127.42, 127.96, 128.47, 129.30, 141.13, 144.32, 147.89, 156.63. MS (ES) m/z=345 ($MH^+$).

A solution of (4-Amino-benzyl)-carbamic acid 9H-fluoren-9-ylmethyl ester (718 mg, 2.09 mmol) in $CH_2Cl_2$ (30 mL) was added dropwise to a solution of thiophosgene (199 μL, 2.61 mmol) in a $CH_2Cl_2$-water mixture (40 mL, 1:1, v/v). After the mixture was stirred over night, the organic phase was isolated and dried ($Na_2SO_4$). The solvent was removed under reduced pressure and the residue purified by dry column vacuum chromatography (0-100% $CH_2Cl_2$ in n-heptane) to yield 29 (643 mg, 80%). $^1$H-NMR (250 MHz, DMSO-d6) δ=4.18-4.25 (3H, m), 4.38 (2H, d, J=6.7 Hz), 7.25-7.45 (8H, m), 7.69 (2H, d, J=7.3 Hz), 7.87-7.90 (3H, m). $^{13}$C-NMR (63 MHz, DMSO-d6) δ=43.64, 47.19, 65.70, 115.55, 120.48, 125.15, 125.49, 126.20, 127.42, 127.98, 128.72, 128.83, 133.55, 136.29, 140.26, 141.16, 144.23, 156.74. MS (ES) m/z=387 ($MH^+$).

Figure 9:
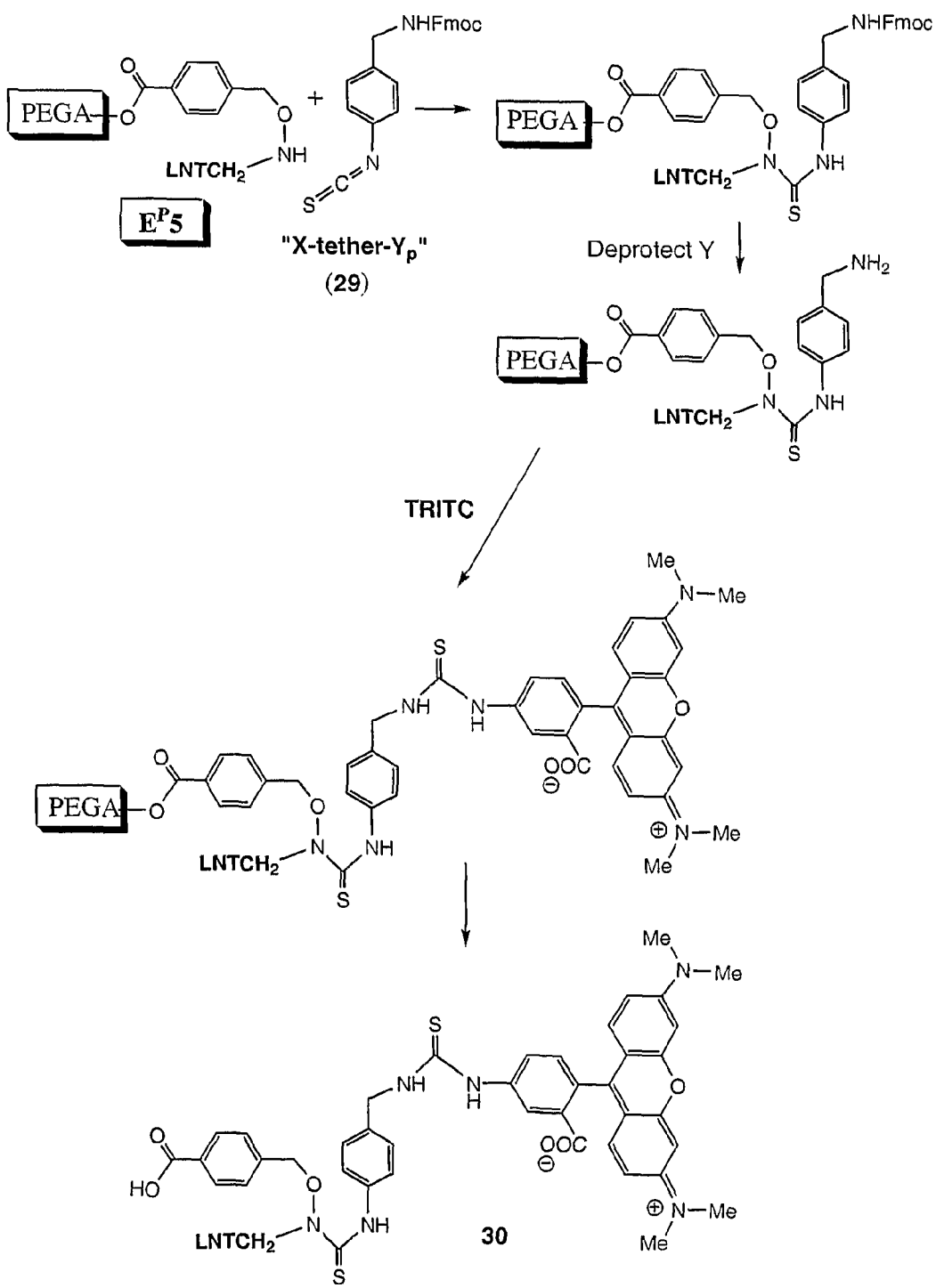

$H^P5$: Attachment of Fmoc-Protected Amino Tether to $E^P5$ Using 29 (FIG. 9)

5 mg of the dried resin ($E^P5$) (0.2 μmol) was washed a couple of times with $CH_2Cl_2$ to ensure proper swelling of the resin. The Fmoc-protected tether (29) (0.8 mg, 2 μmol) was dissolved in DMF (0.2 mL) and added to the resin and left to react for 2 h. The resin was washed with DMF (5×0.5 mL), $CH_2Cl_2$ (5×0.5 mL) and the Fmoc protecting group was removed under standard conditions (20% piperidine in DMF, 0.5 ml 2×10 min). The resin was used directly in the next experiment after washing with DMF (5×0.5 mL)

$I^P5$: Tagging of $H^P5$ Using TRITC

The resin obtained in experiment $H^P5$, now containing a free primary amino group, was incubated with TRITC (0.9 mg, 2 μmol) in DMF (0.2 mL) at rt for 2 h followed by extensive washing with DMF (5×0.5 mL), $CH_2Cl_2$ (5×0.5 mL), methanol (5×0.5 mL) and finally water (5×0.5 mL) to remove excess dye. The resin was used directly in the next step.

$J^P5$: Cleavage of Lacto-N-Tetraose Tagged Using TRITC Via an Amino Tether

The resin obtained in the previous experiment ($I^P5$) was covered with a 1 M solution of LiOH (0.2 mL) and left for 2 h. The liquid was collected from the beads by suction followed by washing of the beads with water (3×0.5 mL). The collected liquid and washings were pooled and pH was adjusted to slightly acidic (pH 3-4) with 10% AcOH. The dark red solution containing the desired product was adsorbed on a Sep-Pak column (50 mg), washed with water (2 mL) and eluted with methanol (0.5 mL). The identity of the product was confirmed by MS (ES) m/z=1465 ($MH^+$).

Capillary Electrophoresis Analysis of Labeled Carbohydrates

Capillary electrophoresis (CE) was performed using an automated PrinCE 2-lift, model 560 CE system (Prince Technologies, The Netherlands). Separations were carried out in an uncoated fused-silica capillary of 75 μm ID with an effective length in the range 50-75 cm (plus 30 cm of extra length from the detection window to the outlet), thermostatically controlled at 25° C. The CE background electrolyte (BGE) was either (A) 50 mM borate buffer pH 9.3 containing 150 mM SDS or (B) 0.2 M borate buffer pH 9.3 containing 0.8% (w/v) γ-CD (Sigma, C-4892). Conditions A were used for the analyses shown in FIGS. 11 and 15-22. Conditions B were used for the analyses shown in FIGS. 10, 13, 14, 23 and 24.

The capillary was conditioned at room temperature by rinsing at 2000 mbar for 30 min with 1 M NaOH, 10 min with water, and 10 min with BGE before use. Between runs the capillary was washed at 2000 mbar for 3 min with 1 M NaOH, 3 min with water, and 3 min with BGE. Samples were injected hydrodynamically for 6 sec at 50 mbar and electrophoresed across a potential difference of 25 kV. All experiments were carried out at a normal polarity, i.e. inlet anodic. Detection was carried out using a fluorescence detector (Argos 250B, Flux Instruments, Switzerland) equipped with the appropriate filters. For samples labeled using TRITC, the excitation and emission filters were respectively 546.1/10 and 570 nm. For samples labeled using FITC, the excitation and emission filters were respectively UG11 (200-400 nm) and 495 nm.

ABBREVIATIONS

The following abbreviations have been used throughout the present application:
AMP CPG Aminopropyl controlled pore glass
BGE Background electrolyte
BSA Bovine serum albumin
CE Capillary electrophoresis
CPG Controlled pore glass
DIPEA N,N-Diisopropylethylamine
DMF N,N-Dimethylformamide
ES Electrospray
FITC Fluorescein isothiocyanate
Fmoc 9-Fluorenylmethyloxycarbonyl
HRMS High resolution mass spectroscopy
LNT Lacto-N-tetraose
MS Mass spectroscopy
NHS N-Hydroxysuccinimide
NMP 1-methyl-2-pyrrolidone
PEGA Polyethylenglycol acrylamide polymer
RNAse B Ribonuclease B
rt Room temperature
TBTU N,N,N',N'-tetramethyl-O-(1H-benzotriazol-1-yl)uroniumtetrafluorborate
TEA Triethylamine
TMR Tetramethylrhodamine
TRITC Tetramethylrhodamine isothiocyanate

We claim:

1. A method of preparing a reactive sugar, comprising the steps of
   i. Providing a sample comprising a reducing sugar
   ii. Providing a solid support (solid) covalently attached to a linker comprising a capture group comprising an —$NH_2$ group, wherein said linker optionally is attached to said solid support via a spacer
   iii. Reacting said reducing sugar with said —$NH_2$ group, thereby obtaining an immobilised sugar,
   iv. Reacting free —$NH_2$ groups with a capping agent, wherein the capping agent comprises a reactive group capable of reacting with an —$NH_2$ group;
   v. Reducing C=N bonds with a reducing agent; and
   vi. obtaining an reactive sugar of the structure SugarCH$_n$—NH— linked to a solid support via a linker and optionally a spacer, wherein n is 1 or 2, wherein step iv is performed prior to step v.

2. The method according to claim 1, which further comprises the step of
   vii. Reacting the —NH— group of the reactive sugar with a derivatising agent comprising an nitrogen-reactive functional group (X), thereby obtaining a sugar covalently attached to said agent.

3. The method according to claim 2, wherein said nitrogen-reactive functional group is an isothiocyanate, an active ester, a carboxylic acid, a Michael acceptor, an alpha-beta unsaturated sulfone, an alkylating agent, an aldehyde, a ketone or a substituted haloaromatic group bearing an electronegative group.

4. The method according to claim 2, wherein said derivatising agent is a spectroscopically detectable compound which is derivatized with a nitrogen-reactive functional group.

5. The method according to claim 2, wherein said derivatizing agent is a fluorescent compound derivatized with a nitrogen-reactive functional group.

6. The method according to claim 4, which furthermore comprises the step of
   viii. detecting said agent attached to the sugar by spectrometry.

7. The method according to claim 2, wherein said derivatizing agent is a mass spectrometry TAG derivatized with a nitrogen-reactive functional group, wherein the mass spectrometry TAG is capable of improving the detection and/or structural characterization of a sugar.

8. The method according to claim 7, wherein the mass spectrometry TAG is a molecule comprising bromine.

9. The method according to claim 7, wherein the mass spectrometry TAG is a charged molecule.

10. The method according to claim 7, wherein the mass spectrometry TAG is an isotope labeled molecule.

11. The method according to claim 7, which furthermore comprises the step of
    viii. detecting said mass spectrometry TAG attached to said sugar by mass spectometry.

12. The method according to claim 2, wherein said derivatizing agent is a first binding partner capable of specific interaction with a second binding partner, and wherein said first binding partner is derivatized with a nitrogen-reactive functional group.

13. The method according to claim 12, wherein one binding partner is a protein and the other binding partner is a ligand of said protein.

14. The method according to claim 12, wherein one binding partner comprises an epitope and the other binding partner is an antibody specifically recognising said epitope.

15. The method according to claim 12, wherein one binding partner is biotin and the other binding partner is an avidin.

16. The method according to claim 12, wherein the second binding partner is conjugated to a detectable label.

17. The method according to claim 2, wherein the derivatizing agent is a nucleic acid derivatized with a nitrogen-reactive functional group or a protected nitrogen reactive functional group.

18. The method according to claim 17, wherein said nucleic acid is a DNA.

19. The method according to claim 17, which furthermore comprises the step of
    viii. detecting said nucleic acid attached to said sugar.

20. The method according to claim 19, wherein said nucleic acid is detected by an essentially complementary nucleic acid conjugated to a detectable label.

21. The method according to claim 19, wherein detection of said nucleic acid comprises amplification of the nucleic acid.

22. The method according to claim 2, wherein said agent is a bifunctional reagent of the structure X-tether-Y or X-tether-$Y_p$, wherein X is a nitrogen-reactive functional group and Y is a second reactive functional group and $Y_p$ is a protected reactive group Y.

23. The method according to claim 22, wherein said second reactive functional group Y is a thiol, a carboxyl group, an activated carboxyl group, a disulfide, an activated disulfide, an alkylating agent, an alkene, an alkyne, an aldehyde, a ketone an azide or a group $Y_p$ which is a protected derivative of the aforementioned group Y or a protected amine.

24. The method according to claim 22, which further comprises the steps of:
    viii, providing a second derivatizing agent comprising a functional group (Z) capable of reacting with Y; and ix. reacting the functional groups Z and Y, thereby covalently attaching the second derivatizing agent to the sugar via a tether and the first derivatizing agent.

25. The method according to claim 24, wherein the second derivatizing agent is a drug, an imaging agent, a peptide, a polypeptide, a protein, an enzyme, a nucleic acid, a spectroscopically detectable compound, a mass spectrometry TAG or a first binding partner capable of specific interaction with a second binding partner.

26. The method according to claim 22, which further comprises the steps of:
   viii. providing a particle which is a microbial organism, a micelle, a phage, a viral or a nanoparticle, wherein the particle comprises a functional group (Z) capable of reacting with Y; and
   ix. reacting the functional groups Z and Y, thereby covalently attaching the particle to the sugar via the tether and the agent.

27. The method according to claim 1, which furthermore comprises the steps of
   viii. contacting the sugar with a detection agent capable of associating with said sugar; and
   ix. detecting the detection agent.

28. The method according to claim 27, wherein said detection agent comprises aryl boronate or heteroarylboronate.

29. The method according to claim 27, wherein the detection agent is a polypeptide.

30. The method according to claim 29, wherein said polypeptide is a lectin, a selectin, a toxin, a receptor, an antibody or an enzyme.

31. The method according to claim 1, wherein the capture group comprises the structure M-$NH_2$, wherein M is a heteroatom.

32. The method according to claim 1, wherein the linker is a non-cleavable linker which is an optionally substituted alkyl, an optionally substituted aryl, an optionally substituted ether or an optionally substituted amide.

33. The method according to claim 1, wherein the linker is a cleavable linker.

34. The method according to claim 33, wherein the cleavable linker is cleavable by reaction with acid, base, nucleophiles, electrophiles, oxidation, reduction, free radicals, light, heat or enzymes.

35. The method according to claim 33, which furthermore comprises the step of cleaving said cleavable linker thereby releasing the sugar, wherein this step may be performed subsequent to step v, vi, vii, viii or ix.

36. The method according to claim 1, wherein the linker is attached to said solid support via a spacer.

37. The method according to claim 36, wherein the spacer is in the range of 0 to 1000 atoms long and optionally branched.

38. The method according to claim 1, wherein the solid support is a polymer, a solid, an insoluble particle or a surface.

39. The method according to claim 1, wherein the solid support is a sensor.

40. The method according to claim 1, which furthermore comprises the step of contacting the sugar with one or more glycosidases, thereby generating a new reducing sugar, provided that the first sugar is a substrate for said glycosidase(s).

41. The method according to claim 40, which furthermore comprises the step of immobilizing newly generated reducing sugars on a solid support.

42. The method according to claim 1, which furthermore comprises the step of contacting the sugar with at least one enzyme which is a glycosyltransferase, a sulfatase, a phosphorylase, a sulfotransferase, a phosphotransferase, a glycosynthase or a transglycosidase, thereby converting said sugar into a new structure.

43. The method according to claim 40, comprising detecting newly generated sugars or structures.

44. The method according to claim 1, wherein the reducing agent is a borane or borohydride comprising a BH bond or a silane comprising a SiH bond.

45. The method according to claim 1, which comprises simultaneous incubation of the sample comprising the reducing sugar, the solid support and the reducing agent.

46. The method according to claim 1, wherein the capture group consists of the structure M-$NH_2$, wherein M is a heteroatom.

* * * * *